(12) United States Patent
Fulton et al.

(10) Patent No.: US 7,803,531 B2
(45) Date of Patent: Sep. 28, 2010

(54) METHOD OF INDUCING APOPTOSIS BY REDUCING THE LEVEL OF THIAMIN

(75) Inventors: Chandler Fulton, Weston, MA (US); Elaine Y. Lai, Weston, MA (US)

(73) Assignee: Brandeis University, Waltham, MA (US)

( * ) Notice: Subject to any disclaimer, the term of this patent is extended or adjusted under 35 U.S.C. 154(b) by 959 days.

(21) Appl. No.: 10/342,119

(22) Filed: Jan. 13, 2003

(65) Prior Publication Data

US 2004/0013658 A1  Jan. 22, 2004

Related U.S. Application Data

(63) Continuation of application No. 09/113,596, filed on Jul. 10, 1998, now Pat. No. 6,506,550.

(60) Provisional application No. 60/087,526, filed on Jun. 1, 1998, provisional application No. 60/052,377, filed on Jul. 11, 1997.

(51) Int. Cl.
| | |
|---|---|
| C12Q 1/68 | (2006.01) |
| A01N 43/04 | (2006.01) |
| A01N 63/00 | (2006.01) |
| A01N 25/00 | (2006.01) |
| C12N 9/00 | (2006.01) |
| C12N 5/00 | (2006.01) |
| C07H 21/04 | (2006.01) |
| C12N 1/20 | (2006.01) |
| C12N 15/00 | (2006.01) |
| C12Q 1/00 | (2006.01) |

(52) U.S. Cl. .............. 435/6; 435/4; 435/252.3; 435/320.1; 435/325; 435/183; 514/44; 514/789; 424/93.1; 536/23.2

(58) Field of Classification Search .......... 435/183, 435/325, 193, 252.2, 320.1, 4, 15, 350, 6, 435/252.3, 189, 93.1; 530/350; 514/789, 514/44; 424/93.1; 536/23.2
See application file for complete search history.

(56) References Cited

U.S. PATENT DOCUMENTS

| | | | |
|---|---|---|---|
| 3,691,016 A | 9/1972 | Patel | |
| 3,969,287 A | 7/1976 | Jaworek et al. | 260/8 |
| 4,195,128 A | 3/1980 | Hildebrand et al. | 435/178 |
| 4,229,537 A | 10/1980 | Hodgins et al. | 435/177 |
| 4,247,642 A | 1/1981 | Hirohara et al. | 435/178 |
| 4,330,440 A | 5/1982 | Ayers et al. | 525/54.31 |
| 5,264,618 A | 11/1993 | Felgner et al. | 560/224 |
| 5,496,731 A * | 3/1996 | Xu et al. | 435/320.1 |
| 5,547,932 A | 8/1996 | Curiel et al. | 435/65 |
| 5,595,873 A | 1/1997 | Joyce | 435/6 |
| 5,616,459 A | 4/1997 | Kramer et al. | 435/5 |
| 5,631,146 A | 5/1997 | Szostak et al. | 435/91.1 |
| 5,646,008 A * | 7/1997 | Thompson et al. | 435/69.1 |

FOREIGN PATENT DOCUMENTS

| | | |
|---|---|---|
| WO | 93/09236 | 5/1993 |
| WO | WO 93/09236 | 5/1993 |
| WO | 93/23569 | 11/1993 |
| WO | WO 93/23569 | 11/1993 |
| WO | 96/01314 | 1/1996 |
| WO | WO 96/01314 | 1/1996 |
| WO | 96/21470 | 7/1996 |
| WO | WO 96/21470 | 7/1996 |
| WO | 96/40958 | 12/1996 |
| WO | WO 96/40958 | 12/1996 |

OTHER PUBLICATIONS

Costello et al. Mechanistic studies on thiaminase I. Overexpression and identification of the active site nucleophile. J Biol Chem. Feb. 16, 1996;271(7):3445-52.*

Butterworth. Effects of thiamine deficiency on brain metabolism: implications for the pathogenesis of the Wernicke-Korsakoff syndromeAlcohol and alcoholism (Oxford, Oxfordshire), (1989) vol. 24, No. 4, pp. 271-279.*

Branden et al. Introduction to Protein Structure, Garland Publishing Inc., New York, p. 247, 1991.*

Abdel-Nabi et al., "Monoclonal antibodies and radioimmunoconjugates in the diagnosis and treatment of prostate cancer," *Semin. Urol.* 10:45-54 (1992).

Abe et al., "A simple method for the detection of two types of thiaminase-producing colonies," *FEMS Microbiol. Lett.* 34:129-133 (1986).

Abe et al., "Molecular studies on thiaminase I," *Biochem. Biophys. Acta* 909:213-221 (1987).

Adelman et al., "In vitro deletional mutagenesis for bacterial production of the 20,000-dalton form of human pituitary growth hormone," DNA 2:183-193 (1983).

(Continued)

*Primary Examiner*—Yong D Pak
(74) *Attorney, Agent, or Firm*—Foley & Lardner LLP

(57) ABSTRACT

The disclosure describes methods for inducing apoptosis of a selected group of vertebrate cells in vivo by reducing the level of thiamin in the cells. Included are methods for inducing apoptosis of cancer cells. Also described are compounds and compositions for use in methods of thiamin depletion and treating diseases such as cancer, and methods for identifying thiamin-depleting agents and for preparing pharmaceutical compositions.

22 Claims, 3 Drawing Sheets

OTHER PUBLICATIONS

Aghi et al., "Synergistic anticancer effects of ganciclovir/thymidine kinase and 5-fluorocytosine deaminase gene therapies," *J Natl. Cancer Inst.* 90:370-380 (1988).

Agren, "On the purification of the thiamin-inactivating fish factor," *Acta Physiol. Scand.* 9:306-312 (1945).

Albert et al., "Vitamin $B_{12}$ synthesis by human small intestinal bacteria," *Nature* 283:781-782 (1980).

Alberts et al., "Intraperitoneal cisplatin plus intravenous cyclophosphamide versus intravenous cisplatin plus intravenous cyclophosphamide for stage III ovarian cancer," New Engl. J. Med. 335:1950-1955 (1996).

Alexander et al., "Alcohol encephalopathy in man and fish-diet disease in foxes and fishes," *Trans. Am. Neurol. Assoc.* 67:119-122 (1941).

Alfonso et al., *Remington: The science and practice of pharmacy*, 19$^{th}$ Ed. Easton PA: Mack Publishing Co. vol. 1 & 2(1995) (Table of Contents Only).

Alston et al., "Enzymatic conversion of the antibiotic metronidazole to an analog of thiamine," *Arch. Biochem. Biophys.* 257:357-362 (1987).

Anderson, "Human gene therapy," *Nature* 392(Suppl.):25-30 (1998).

Arap et al., "Cancer treatment by targeted drug delivery to tumor vasculature in a mouse model," *Science* 279:377-380 (1998).

Arteaga et al., "Tissue-targeted antisense c-fos retroviral vector inhibits established breast cancer xenografts in nude mice," *Cancer Res.* 56:1098-1103 (1996).

Backstrom et al., "Biosynthesis of thiamin I: The function of the thiE gene product," *J.Am. Chem. Soc.* 117:2351-2352 (1995).

Bagshawe, "Antibody-directed enzyme prodrug therapy: a review," *Drug Dev. Res.* 34:220-230 (1995).

Bagshawe, "Antibody-directed enzymes revive anti-cancer prodrug concept," *Br. J. Cancer* 56:531-532 (1987).

Bander, "Current status of monoclonal antibodies for imaging and therapy of prostate cancer," *Semin. Oncol.* 21:607-612 (1994).

Barry et al., "Toward cell-targeting gene therapy vectors: Selection of cell-binding peptides from random peptide-presenting phage libraries," *Nature Med.* 2:299-305 (1996).

Bartel et al., "Isolation of new ribozymes from a large pool of random sequences," *Science* 261:1411-1418 (1993).

Baselga et al., "Phase II study of weekly intravenous recombinant humanized anti-p185$^{HER2}$ monoclonal antibody in patients with HER2/neu-overexpressing matastatic breast cancer," [see comments] *J. Clin. Oncol.* 14:737-744 (1996).

Basu et al., "The thiamine status of patients with cancer as determined by the red cell transketolase activity," *Int. J. Vitam. Nutr. Res.* 44:53-58 (1974).

Beaudry et al., "Directed evolution of an RNA enzyme," *Science* 257:635-641 (1992).

Begent et al., "Clinical evidence of efficient tumor targeting based on single-chain Fv antibody selected from a combinatorial library," *Nature Med.* 2:979-984 (1996).

Benet et al., "Pharmacokinetics: The dynamics of drug absorption, distribution, and elimination," *Gilman's The Pharmacological Basis of Therapeutics*, Ninth Ed. (ed. Hardman and Limbird) McGraw-Hill: New York pp. 3-27. (1996).

Benhar et al., "Cloning, expression and characterization of the Fv fragments of the anticarbohydrate monoclonal antibodies B1 and B5 as single-chain immunotoxins," *Protein Eng.* 7:1509-1515 (1994).

Bernsen et al., "The effect of the anti-angiogenic agent TNP-470 on tumor growth and vascularity in low passaged xenografts of human gliomas in nude mice," *J. Neuro-Oncol.* 38:51-57 (1998).

Berzal Herranz et al., "Essential nucleotide sequences and secondary structure elements of the hairpin ribozyme," *EMBO J.* 12:2567-2574 (1993).

Bigner et al., "Phase I studies of treatment of malignant gliomas and neoplastic meningitis with $^{131}$I-radiolabeled monoclonal antibodies anti-tenascin 81C6 and anti-chondroitin proteoglycan sulfate Me1-14F (ab')$_2$—a preliminary report," *J. Neuro-Oncol.* 24:109-122 (1995).

Bird et al., "Single-chain antigen-binding proteins," *Science* 242:423-426 (1988).

Blakey et al., "Antibody-directed enzyme prodrug therapy (ADEPT) for treatment of major solid tumour disease," *Biochem. Soc. Trans.* 23:1047-1050 (1995).

Blank et al., "A novel anti-breast epithelial mucin MAb (BrE-3). Characterization and experimental biodistribution and immunotherapy," *Cancer* 5:38-44 (1992).

Boehm et al., "Antiangiogenic therapy of experimental cancer does not induce acquired drug resistance," *Nature* 390:404-407 (1997).

Boleti et al., "Therapeutic monoclonals," *Biochem. Soc. Trans.* 23:1044-1047 (1995).

Borgstrom et al., "Complete inhibition of angiogenesis and growth of microtumors by anti-vascular endothelial growth factor neutralizing antibody: Novel concepts of angiostatic therapy from intravital videomicroscopy," *Cancer Res.* 56:4032-4039 (1996).

Borgstrom et al., "Neutralizing anti-vascular endothelial growth factor antibody completely inhibits angiogenesis and growth of human prostate carcinoma micro tumors in vivo," *Prostate* 35:1-10 (1998).

Boros et al., "Oxythiamine and dehydroepiandrosterone inhibit the nonoxidative synthesis of ribose and tumor cell proliferation," *Cancer Res.* 57:4242-4248 (1997).

Boros et al., "Thiamine supplentation to cancer patients: A double edged sword," *Anticancer Res.* 18:595-602 (1998).

Breaker et al., "Inventing and improving ribozyme function: Rational design versus iterative selection methods," *TIBTECH* 12:268-275 (1994).

Breaker, "Are engineered proteins getting competition from RNA?" *Curr. Op. Biotech* 7:442-448 (1996).

Breaker, "DNA enzymes," *Nature Biotech* 15:427-431 (1997).

Brinkmann et al., "B3(Fv)-PE38KDEL, a single-chain immunotoxin that causes complete regression of a human carcinoma in mice," *Proc. Natl. Acad. Sci. USA* 88:8616-8620 (1991).

Brooks et al., "Disruption of angiogenesis by PEX, a noncatalytic metalloproteinase fragment with integrin binding activity," *Cell* 92:391-400 (1998).

Brooks et al., "Integrin $\alpha v \beta 3$ antagonists promote further tumor regression by inducing apoptosis of angiogenic blood vessels," *Cell* 79:1157-1164 (1994).

Brown, "Hunt for viable vectors leads to jobs for gene therapy researchers," *The Scientist* 10:1,7 (1996).

Cai et al., "A melanoma-specific $V_H$ antibody cloned from a fusion phage library of a vaccinated melanoma patient," *Proc. Natl. Acad. Sci. USA* 93:6280-6285 (1996).

Campbell et al., "Molecular mediators of angiogenesis in bladder cancer," *Cancer Res.* 58:1298-1304(1998).

Campbell et al., *RNA* 1:598 (1995).

Cao et al., "Expression of angiostatin cDNA in a murine fibrosarcoma suppresses primary tumor growth and produces long-term dormancy of metastases," *J. Clin. Invest.* 101:1055-1063 (1998).

Capecchi, "High efficiency transformation by direct microinjection of DNA into cultured mammalian cells," *Cell* 22:479-488 (1980).

Chambers et al., "Antimicrobial agents: General considerations," *Goodman and Gilman's The Pharmacological Basis of Therapeutics*, Ninth Ed. (ed. Hardman and Limbird) McGraw-Hill: New York pp. 1029-1056 (1996).

Chaudhary et al., "A recombinant immunotoxin consisting of two antibody variable domains fused to Pseudomonas exotoxin," *Nature* 339:394-397 (1989).

Chen et al., "Gene therapy for brain tumors: Regression of experimental gliomas by adenovirus-mediated gene transfer in vivo," *Proc. Natl. Acad. Sci. USA* 91:3054-3057 (1994).

Chen et al., "High-efficiency transformation of mammalian cells by plasmid DNA," *Mol. Cell. Biol.* 7:2745-2752 (1987).

Chowdhury et al., "Long-term improvement of hypercholestolemia after ex vivo gene therapy in LDLR-deficient rabbits," *Science* 254:1802-1805 (1991).

Christensson et al., "Enzymatic activity of prostate-specific antigen and its reactions with extracellular serine proteinase inhibitors," *Eur. J. Biochem.* 194:755-763 (1990).

Chu et al., "Electroporation for the efficient transfection of mammalian cells with DNA," *Nucleic Acids Res.* 15:1311-1326 (1987).

Chu, "Cellular responses to cisplatin. The roles of DNA-binding proteins and DNA repair," *J. Biol. Chem.* 269:787-790 (1994).

Chu, "Prostate-specific antigen in screening of prostate cancer," *J. Clin. Lab. Anal.* 8:323-326.
Cohen et al., "Apoptosis and programmed cell death in immunity," *Annu. Rev. Immunol.* 10:267-293 (1992).
Cohen et al, "Bacterial adhesion to and penetration of intestinal mucus in vitro," *Methods Enzymol.* 253:309-314 (1995).
Cohen, "Apoptosis," *Immunol. Today* 14:126-130 (1993).
Cooper et al., "The role of thiamine in nerve conduction," *Thiamine Deficiency* pp. 112-121 (1967).
Costello et al., "Mechanistic studies on thiaminase I. Overexpression and identification of the active site nucleophile," *J. Biol. Chem* 271:3445-3452 (1996).
Cowgill, The physiology of vitamin $B_1$. The Vitamins (ed. American Medical Association) American Medical Association: Chicago pp. 159-178 (1939).
Creighton, *Proteins: Structure and Molecular Properties*, W.H. Freeman & Co. San Francisco, pp. 79-86 (1983).
Cristiano et al., "Hepatic gene therapy: Adenovirus enhancement of receptor-mediated gene delivery and expression in primary hepatocytes," *Proc. Natl. Acad. Sci. USA* 90:2122-2126 (1993).
Curiel DT et al., "Gene transfer to respiratory epithelial cells via the receptor-mediated endocytosis pathway," *Am J. Respir. Cell Mol. Biol.* 6:247-252 (1992).
Curiel et al., "Adenovirus enhancement of transferrin-polylysine-mediated gene delivery," *Proc. Natl. Acad. Sci. USA* 88:8850-8854 (1991).
Dachs et al., "Targeting gene expression to hypoxic tumor cells," *Nature Medicine* 3(5):515-520 (1997).
Dean-Nystrom, "Identification of intestinal receptors for enterotoxigenic *Escherichia coli*," *Methods Enzymol.* 253:315-325 (1995).
Deb et al., "Treatment of hormone-refractory prostate cancer with $^{90}$Y-CYT-356 monoclonal antibody," *Clin. Cancer Res.* 2:1289-1297 (1996).
Denis et al., "Matrix metalloproteinase inhibitors: Present achievements and future prospects," *Invest. New Drugs* 15:175-185 (1997).
Denmeade et al., "Role of programmed (apoptotic) cell death during the progression and therapy for prostate cancer," *Prostate* 28:251-265 (1996).
Deolalker et al., "Thiaminase from fresh-water, brackish-water and salt-water fish," *Nature* 173:489-490 (1954).
Deutsch et al., "Distribution of a vitamin $B_1$ destructive enzyme in fish," *Proc. Soc. Exptl. Biol. Med.* 53:63-65 (1943).
Deutsch et al., "Mechanism of vitamin B1 destruction by a factor in raw smelt," *Proc. Soc. Exptl. Biol. Med.* 51:119-122 (1942).
Deutscher M.P. (ed.), "Guide to protein purification," *Methods Enzymol.* vol. 182 (1990) (Table of Contents Only).
DeVita et al., *Cancer: Principles and practice of oncology*, 5$^{th}$ Ed., Philadelphia: Lippincott-Raven (1997) (Table of Contents Only).
Dixon et al., "Immunologic unresponsiveness induced by protein antigens," *J. Exp. Med.* 101:245-257 (1955).
Donehower et al., "Mice deficient for p53 are developmentally normal but susceptible to spontaneous tumors," *Nature* 356:215-221 (1992).
Douthit et al., "Thiaminase I of *Bacillus thiaminolyticus*," *Arch. Biochem. Biophys.* 113:331-337 (1966).
Dunnebacke et al., "Cytopathogenic material from amoebae of the genus Naegleria," *Microbiology* (ed. Schlessinger, D.) American Society for Microbiology pp. 583-585 (1977).
Dunnebacke et al., "Infectious agent from a free-living soil amoeba, Naegleria gruberi," *Science* 174:516-518 (1971).
Dunnebacke et al., "Morphological response of cultured cells to Naegleria amoeba cytopathogenic material," *J. Cell Sci.* 75:1-16 (1985).
Dunnebacke et al., "NACM, a cytopathogen from Naegleria ameba: Purification, production of monoclonal antibody, and immunoreactive material in NACM-treated vertebrate cell cultures," *J. Cell Sci.* 93:391-401 (1989).
Dunnebacke et al., "The nature of a cytopathogenic material present in amebae of the genus Naegleria," *Amer. J. Trop. Med. Hyg.* 26:412-421 (1977).
Earl et al., "Mystery of the poisoned expedition," *Nature* 368:683-684 (1994).

Eastman, "Activation of programmed cell death by anticancer agents: Cisplatin as a model system," *Cancer Cells* 2:275-280 (1990).
Eck et al., "Gene-based therapy," *Goodman and Gilman's The Pharmacological Basis of Therapeutics*, Ninth Ed. (ed. Hardman and Limbird) McGraw-Hill: New York pp. 77-101 (1996).
Eckhardt et al., "A phase I clinical and pharmacokinetic study of the angiogenesis inhibitor, tecogalan sodium," *Ann. Oncol.* 7:491-496 (1966).
Eda et al., "The suppression of postoperative liver metastasis caused by the continuous intraportal infusion of angiogenesis inhibitor FR-118487 in a rabbit colon cancer model," *Surg. Today* 28:273-278 (1998).
Edwin, "Determination of thiaminase activity using thiazole-labeled thiamine," *Methods Enzymol.* 62:113-117 (1979).
Eisenstein et al., "Immunotherapy of a plasmacytoma with attenuated salmonella," *Med. Oncol.* 12:103-108 (1995) (Abstract).
Ellis et al., "Mechanisms and functions of cell death," *Annu. Rev. Cell Biol.* 7:663-698 (1991).
Ensminger et al., "Regional cancer chemotherapy," *Cancer Treat. Rep.* 68:101-115 (1984).
Evans et al., "The mechanism of anti-Aneurin activity of bracken (*Pteris aquilina*)," *Biochem. J.* 46:xxxviii-xxxix (1950).
Evans, "Thiaminases and their effects on animals," *Vitamins and Hormones* 33:467-504 (1975).
Felgner et al., "Cationic liposome-mediated transfection," *Nature* 337:387-388 (1989).
Felgner et al., "Lipofection: A highly efficient, lipid mediated DNA-transfection procedure," *Proc. Natl. Acad. Sci. USA* 84:7413-7417 (1987).
Ferrari et al., "An in vivo model of somatic cell gene therapy for human severe combined immunodeficiency," *Science* 251:1363-1366 (1991).
Field et al., "A study of the blood constituents of carp and trout," *J. Biol. Chem.* 148:261-269 (1943).
Fingl et al., "Ch. 1: General Principles," *The Pharmacological Basis of Therapeutics* pp. 1-46 (1975).
Fisher, "Apoptosis in cancer therapy: Crossing the threshold," *Cell* 78:539-542 (1994).
Fleuren et al., "Tumor heterogeneity and immunotherapy of cancer," *Immunol. Rev.* 145:91-122 (1995).
Folkman, "Angiogenic therapy," *Cancer: Principles and practice of Oncology*, 5$^{th}$ Ed. (ed. Devita et al.) Lippincott-Raven: Philadelphia pp. 3075-3085 (1997).
Fox et al., "Anaerobic bacteria as a delivery system for cancer gene therapy: in vitro activitation of 5-fluorocytosine by genetically engineered clostridia," *Gene Therapy* 3:173-178 (1996).
Fox, "Oxford BioMedica builds its business on development of retroviral vectors," *Genetic Engineering News* p. 27 (1997).
Freeman et al., "In situ use of suicide genes for cancer therapy," *Semin Oncol.* 23:31-45 (1996).
Freeman et al., "The 'bystander effect': Tumor regression when a fraction of the tumor mass is genetically modified," *Cancer Res.* 53:5274-5283 (1993).
Friedrich, "6. Thiamin, vitamin $B_1$, Aneurin," *Vitamins* Walter de Gruyter:Berlin pp. 339-401 (1988).
Fruton et al., "The B Vitamins," *General Biochemistry*, 2$^{nd}$ Ed. John Wiley and Sons: New York pp. 980-984 (1958).
Fujimiya, "Studies on thiaminase in human feces III: Frequency of the disease with thiaminase,." *Vitamins* 3:270 (1951) (Abstract).
Fujita et al., "Studies on thiaminase I: Activation of thiamine breakdown by organic bases," *J. Biol. Chem.* 196:289-295 (1952).
Fujita et al., "Studies on thiaminase IV: Synthesis of thiamine," *J. Biol. Chem.* 196:313-320 (1952).
Fujita, "Thiaminase," *Adv. Enzymol.* 15:389-421 (1954).
Fujita, "Thiaminase," *Methods Enzymol.* 2:622-628 (1955).
Fulton, "Amebo-flagellates as research partners: The laboratory biology of Naegleria and Tetramitus," *Meth. Cell Physiol.* 4:341-476 (1970).
Fulton, "Cell differentiation in Naegleria gruberies," *Annu. Rev. Microbiol.* 31:597-629 (1977).
Fulton, "Naegleria: A research partner for cell and developmental biology," *J. Euk. Microbiol.* 40:520-532 (1993).

Galardy et al., "Inhibition of angiogenesis by the matrix metalloprotease inhibitor N-[2R-2-(hydroxamidocarbonymethyl)-4-methylpentanoyl)]-L-tryptophan methylamide," *Cancer Res.* 54:4715-4718 (1994).

Georgiannos et al., "Micronutrients in gastrointestinal cancer," *Br. J. Cancer* 68:1195-1198 (1993).

Gerschenson et al., "Apoptosis: a different type of cell death," *FASEB J.* 6:2450-2455 (1992).

Gittes, "Carcinoma of the prostate," *New Engl. J. Med.* 324:236-245 (1991).

Glinsky et al., "Inhibition of colony formation in agarose of metastatic human breast carcinoma and melanoma cells by synthetic glycoamine analogs," *Clin. Exp. Metastasis* 14:253-267 (1996).

Graeber et al., "Hypoxia-mediated selection of cells with diminished apoptotic potential in solid tumors," *Nature* 379:88-91 (1996).

Green et al., "A deficiency disease of foxes produced by feeding fish B1 avitaminosis analogous to Wernicke's disease of man," *J. Nutr.* 21:243-256 (1941).

Green et al., "The inactivation of vitamin $B_1$ in diets containing whole fish," *J. Nutrition* 23:165-174 (1942).

Gref et al., "Biodegradable long-circulating polymeric nanospheres," *Science* 263:1600-1603 (1994).

Gregoriadis, "Engineering liposomes for drug delivery: progress and problems," *Trends Biotech* 13:527-537 (1995).

Gutman et al., "Failure of thalidomide to inhibit tumor growth and angiogenesis in vivo," *Anticancer Res.* 16:3673-3677 (1996).

Haake, "Thiamine-dependent enzymes," *Enzyme Mechanisms* (ed. Page et al.) Royal Society of Chemistry pp. 390-403 (1987).

Hamada, "Studies on dispositions of carriers of *Bacillus thiaminolyticus Matsukawa et Misawa* in the intestinal canal, I. On so-called thiaminosis-patients and carriers of *B. thiaminolyticus Matsukawa et Misawa*," *Vitamins* 6:951-956 (1953) (Abstract).

Hamada, "Studies on dispositions of carriers of *Bacillus thiaminolyticus Matsukawa et Misawa* in the intestinal canal, III. On the oral administration of *B. thiaminolyticus Matsukawa et Misawa* on various animals," *Vitamins* 7:65 (1954) (Abstract).

Hamada, "Studies on dispositions of carrier of *Bacillus thiaminolyticus Matsukawa et Misawa*," *J. Vitamins* 2:72-77 (1956).

Han et al., "Ligand-directed retroviral targeting of human breast cancer cells," *Proc. Natl. Acad. Sci. USA* 92:9747-9751 (1995).

Hannun, "Apoptosis and the dilemma of cancer chemotherapy," *Blood* 89:1845-1853 (1997).

Harris et al., "Thiamine," *The Vitamins: Chemistry, Physiology, Pathology* (ed. Sebrell et al.) Academic Press: New York pp. 403-480 (1954).

Harris, "Thiaminase," *The Enzymes: Chemistry and Mechanism of Action*, (ed. Sumner et al.) Academic Press: New York pp. 1186-1206 (1951).

Hartley et al., "Anti-angiogenic treatment with linomide as adjuvant to surgical castration in experimental prostate cancer," *J. Urol.* 158:902-907 (1997).

Hartmann et al., "The molecular epidemiology of P53 gene mutations in human breast cancer," *Trends. Genet.* 13:27-33 (1997).

Henderson et al., "Human tumor antigens are ready to fly," *Adv. Immunol.* 62:217-256 (1996).

Heppner et al., "The liquifaction (oncolysis) of malignant gliomas by a nonpathogenic Clostridium," *Acta Neurochir.* 42:123-125 (1978).

Herlyn et al., "Colorectal carcinoma-specific antigen: detection by means of monoclonal antibodies," *Proc. Natl. Acad. Sci. USA* 76:1438-1442 (1979).

Hershfield et al., "Treatment of adenosine deaminase deficiency with polyethylene glycol-modified adenosine deaminase," *New Engl. J. Med.* 316:589-596 (1987).

Hickman et al., "Apoptosis and cancer chemotherapy," *Phil. Trans. R. Soc. B*. 345:319-325 (1994).

Hickman, "Apoptosis induced by anticancer drugs," *Cancer Metast. Rev.* 11:121-139 (1992).

Hockel et al., "Association between tumor hypoxia and malignant progression in advanced cancer of the uterine cervix," *Cancer Res.* 56:4509-4515 (1996).

Holzmayer et al., "Isolation of dominant negative mutants and inhibitory antisense RNA sequence by expression selection of random DNA fragments," *Nucleic Acids Research* 20(4):711-717 (1992).

Horikawa et al., "Studies on thiaminase in human feces. VIII. Experimental thiaminosis in human body by means of oral administration of *Bacillus thiaminolyticus*," *Vitamins* 4:119 (1951) (Abstract).

Horoszewicz et al., "Monoclonal antibodies to a new antigenic marker in epithelial prostatic cells and serum of prostatic cancer patients," *Anticancer Res.* 7:927-936 (1987).

Huang et al., "Tumor infarction in mice by antibody-directed targeting of tissue factor to tumor vasculature," *Science* 275:547-550 (1997).

Huston et al., "Medical applications of single-chain antibodies," *Int. Rev. Immunol.* 10:195-217 (1993) (Abstract).

Hutter et al., "Inhibition of thiaminase I from *Bacillus thiaminolyticus*: Evidence supporting a covalent 1,6-dihydropyrimidinyl-enzyme intermediate," *Biochem* 26:1969-1973 (1987).

Ikehata, "The purification of thiaminase II," *J. Gen. Appl. Microbiol.* 6:30-39 (1960).

Inouye et al., "Etiology and pathology of beriberi." *Review of Japanese Literature on Beriberi and Thiamine* (ed. Shimazono et al.) Igaku Shoin, Ltd.: Tokyo pp. 1-28 (1965).

Irie et al., "Regression of cutaneous metastatic melanoma by intralesional injection with human monoclonal antibody to ganglioside GD2," *Proc. Natl. Acad. Sci. USA* 83:8694-8698 (1986).

Ishizaka et al., "Isolation of active ribozymes from an RNA pool of random sequences using an anchored substrate RNA," *BBRC* 214:403-409 (1995).

Jaffee et al., "High efficiency gene transfer into primary human tumor explants without cell selection," *Cancer Res.* 53:2221-2226 (1993).

Jones et al., "Replacing the complementarity-determining regions in a human antibody with those from a mouse," *Nature* 321:522-525 (1986).

Joyce, "Amplification, mutation and selection of catalytic RNA," *Gene* 82:83-87 (1989).

Joyce, "Directed molecular evolution," *Scientific American* 267:90-97 (1992).

Kairemo, "Radioimmunotherapy of solid cancers: A review," *Acta Oncol.* 35:343-355 (1996).

Kaneda et al., "The improved efficient method for introducing macromolecules into cells using HVJ (Sendai Virus) liposomes with gangliosides," *Expt. Cell Res.* 173:56-69 (1987).

Kaneda et al., "Increased expression of DNA conintroduced with nuclear protein in adult rat liver," *Science* 243:375-378 (1989).

Kenten, "The partial purification and properties of a thiaminase from bracken (*Pteridium aquilinum* (L) Kuhn)" *Biochem J.* 67:25-33 (1957).

Kimura et al., "Occurrence of thiaminase II in *Saccharomyces cerevisiae*," *Experientia* 43:888-890 (1987).

Kimura, "Thiamine decomposing bacteria," *Review of Japanese Literature on Beriberi and Thiamine* (ed. Shimazono et al.) Igaku Shoin, Ltd.:Tokyo pp. 255-274 (1965).

King et al., "Preparation of protein conjugates via intermolecular disulfide bond formation," *Biochem* 17:1499-1505 (1978).

Kobayashi, "Thiaminase from Clostridium sporogenes I. Purification of thiaminase I," *Vitamins* 49:45-51 (1975) (Abstract).

Kobayashi, "Thiaminase from Clostridium sporogenes II. Properties of the purified thiaminase I," *Vitamins* 49:111-119 (1975) (Abstract).

Kobayashi, "Thiaminase from Clostridium sporogenes III. Thiamine synthesis by the purified thiaminase I," *Vitamins* 49:185-194 (1975) (Abstract).

Korsmeyer, "Regulators of cell death," *Trends Genet.* 11:101-105 (1995).

Krampitz et al., "The manner of inactivation of thiamine by fish tissue," *J. Biol. Chem.* 152:9-17 (1944).

Kudelka et al., "Complete remission of metastatic cervical cancer with the angiogenesis inhibitor TNP-470," *N. Engl. J. Med.* 338:991-992 (1998).

Kumar et al., "Artificial evolution and natural ribozymes," *FASEB J.* 9:1183-1195 (1995).

Kyprianou et al., "Programmed cell death as a new target for prostatic cancer therapy," *Prostate Cancer: Cell and molecular mechanisms in diagnosis and treatment* (Cancer Surveys, vol. 11) (ed. Isaacs) Cold Spring Harbor Laboratory Press: Cold Spring Harbor, New York pp. 265-277 (1991).

Lai et al., "An infective agent from Naegleria amebae induces delayed cell death in mammalian cells," *J. Cell Biol.* 111:494a (abstr.) (1990).

Lamm et al., "A randomized trial of intravesical doxorubicin and immunotherapy with bacille Calmette-Guerin for transitional cell carcinoma of the bladder," *New Engl. J. Med.* 325:1205-1209 (1991).

Langer, "Drug delivery and targeting," *Nature* 392(Supp.):5-10 (1998).

Lee et al., "Prostate-specific antigen promoter driven gene therapy targeting DNA polymerase-alpha and topoisomerase II alpha in prostate cancer," *Anticancer Res.* 16:1805-1812 (1996).

Lee et al., "Treatment of intracranial human glioma xenografts with $^{131}$I-labeled anti-tenascin monoclonal antibody 81C6," *Cancer Res.* 48:2904-2910 (1988).

Levesque et al., "Prostate specific antigen expression by various tumors," *J. Clin. Lab. Anal.* 9:123-128 (1995) (Abstract).

Levy et al., "Centrin is a conserved protein that forms diverse associations with centrioles and MTOCs in Naegleria and other organisms," *Cell Motil. Cytoskeleton* 33:298-323 (1996).

Lieber et al., "Selection of efficient cleavage sites in target RNAs by using a ribozyme expression library," *Mol. Cell Biol.* 15:540-551 (1995).

Lienhard, "Kinetic evidence for a (4-amino-2-methyl-5-pyrimidinyl)methyl-enzyme intermediate in the thiaminase I reaction," *Biochem* 9:3011-3020 (1970).

Lilja et al., "Prostate-specific antigen in human serum occurs predominantly in complex with α1-antichymotrypsin," *Clin. Chem.* 37:1618-1625 (1991).

Liu et al., "Monoclonal antibodies to the extracellular domain of prostate-specific membrane antigen also react with tumor vascular endothelium," *Cancer Res.* 57:3629-3634 (1997).

Long et al., "Kinetic characterization of intramolecular and intermolecular hammerhead RNAs with stem II deletions," *Proc. Natl. Acad. Sci. USA* 91:6977-6981 (1994).

Lowe et al., "p53-dependent apoptosis modulates the cytotoxicity of anticancer agents," *Cell* 74:957-967 (1993).

Lu et al., "Antisense DNA delivery in vivo: liver targeting by receptor-mediated uptake," *J. Nucl. Med.* 35:269-275 (1994).

Marcus et al., "Water-soluble vitamins: The vitamin B complex and ascorbic acid," *Goodman and Gilman's The Pharmacological Basis of Therapeutics*, Ninth Ed. (ed. Hardman et al.) McGraw-Hill:New York pp. 1555-1572 (1996).

Martin et al., "Apoptosis and cancer: The failure of controls on cell death and cell survival," *Crit. Rev. Oncol. Hematol.* 18:137-153 (1995).

Marucci et al., "Effect of xanthine analog on human hepatocellular carcinoma cells (Alexander) in culture and in xenografts in SCID mice," *Hepatology* 26:1195-1202 (1997).

Maisonpierre et al., "Angiopoieten-2, a natural antagonist for Tie2 that disrupts in vivo angiogenesis," *Science* 277:55-60 (1997).

Matsudaira, "Limited N-terminal sequence analysis," *Methods Enzymol.* 182:602-613 (1990).

Matsukawa et al., "Studies on the thiamine deficiency due to bacterial thiaminase," *J. Vitaminol.* 1:53-55 (1955).

Matsushima et al., "Apoptosis is restricted to the thalamus in thiamine-deficient rats," Neuropharmacology and Neurotoxicology 8:867-870 (1997).

Matthews et al., "Substrate phage: Selection of protease substrates by monovalent phage display," *Science* 260:1113-1117 (1993).

McCafferty et al., "Phage antibodies: Filamentous phage displaying antibody variable domains," *Nature* 348:552-554 (1990).

McCleary et al., "The purification and properties of a thiaminase I enzyme from nardoo (Marsilea drummondii)," *Phytochemistry* 16:207-213 (1977).

Melkonyan et al., "SARPs: A family of secreted apoptosis-related proteins," *Proc. Natl. Acad. Sci. USA* 94:13636-13641 (1997).

Melnick et al., "Physiological availability of the vitamins," *J. Nutrition* 30:81-88 (1945).

Melton et al., "Antibody-enzyme conjugates for cancer therapy," *J. Natl. Cancer Inst.* 88:153-165 (1996).

Menge, "Purification of proteins from cell culture supernatant solutions," *Methods Enzymol.* 228:617-626 (1994).

Mickelsen, "Intestinal synthesis of vitamins in the nonruminant," *Vitamins and Hormones* 14:1-95 (1956).

Miller et al., "Gene transfer by retrovirus vectors occurs only in cells that are actively replicating at the time of infection," *Mol. Cell. Biol.* 10:4239-4242 (1990).

Miller et al., "A new approach to chemotherapy based on molecular biology and nucleic acid chemistry: Matagen (masking tape for gene expression)," *Anti-cancer Drug Des.* 2:117-128 (1987).

Miller, "Human gene therapy comes of age" *Nature* 357:455-460 (1992).

Minchinton et al., "The effect of thalidomide on experimental tumors and metastases," *Anticancer Drugs* 7:339-343 (1996).

Minton et al., "Chemotherapeutic tumour targeting using clostridial spores," *FEMS Microbiol. Rev.* 17:357-364 (1995).

Minton et al., "Host: Vector systems for gene cloning in Clostridium," *Microbiol. Sci.* 5:310-315 (1988).

Minz, "Sur la liberation de la vitamin B1 par le tronc isole du nerf pneumogastrique soumis a l'excitation electrique," *Compt. Rend. Soc. Biol.* 127:1251-1253 (1938).

Moradpour et al., "Specific targeting of human hepatocellular carcinoma cells by immunoliposomes in vitro," *Hepatology* 22:1527-1537 (1995).

Mose et al., "Oncolysis by clostridia I. Activity of Clostridium butyricum (M-55) and other non-pathogenic clostridia against the Ehrlich carcinoma," *Cancer Res.* 24:212-216 (1959).

Mulligan, "The basic science of gene therapy," *Science* 260:926-931 (1993).

Munck et al., "Pharmacokinetic and pharmacodynamic advantages of pirarubicin over adriamycin after intraarterial hepatic administration in the rabbit VX2 tumor model," *Cancer Res.* 53:1550-1554 (1993).

Murata, "Actions of two types of thiaminase on thiamin and its analogues," Ann. N. Y. Acad. Sci. 378:146-155 (1982).

Murata, "Thiaminase," *Review of Japanese Literature on Beriberi and Thiamine* (ed. Shimazono et al.) Igaku Shoin, Ltd: Tokyo pp. 220-254 (1965).

Nakamaye et al., "AUA-cleaving hammerhead ribozymes: Attempted selection for improved cleavage," *Biochemistry* 33:1271-1277 (1994).

Nauts, "Bacteria and cancer-antagonisms and benefits," *Cancer Surv.* 8:713-723 (1989).

Nseyo et al., "Therapy of superficial bladder cancer," *Semin. Oncol.* 23:598-604 (1996).

O'Reilly et al., "Angiostatin induces and sustains dormancy of human primary tumors in mice," *Nature Med.* 2:689-692 (1996).

Oparin et al., "Antitumor effect of hydroxythiamine in mice with Ehrlich ascites carcinoma (In Russian)," *Eksp. Onkol.* 14:74-77 (1992).

Orgel, "Selection in vitro," *Proc. R. Soc.* London 8205:435-442 (1979).

Ostrovsky et al., "Activity of thiaminase I and its fragments after administration of the enzymes to the animal organism," *Biol. Zentralbl.* 107:17-20 (1988).

Ostrovsky et al., "Specific activity of thiamine and oxythiamine immobilized on modified cellulose," (In Russian) *Vopr. Pitan.* 1987:47-50 (1987).

Ostrovsky et al., Effect of oxythiamin on the growth of Ehrlich's ascites tumor in white mice, (In Russian) *Dokl. Akad. Nauk BSSR* 29:655-657 (1985) (Abstract).

Ostrovsky, "Benefits from thiamine deficiency: Prospects for medicine," *F. Physiological and Pathological Aspects* pp. 382-389, (1991).

Ostrovsky, "Impermeability of the blood-brain barrier to hydroxythiamine," *Vopr. Med. Khim.* 11:95-97 (1965).

Parker et al., "Cancer statistics," *CA Cancer J. Clin.* 47:5-27 (1997).

Parsonnet, "Gastrointestinal microbiology," *Encyclopedia of Microbiology* Academic Press, Inc.: San Diego (ed. Lederberg) pp. 245-258 (1992).

Parsons et al., "Phase I/II trial of batimastat, a matrix metalloproteinase inhibitor, in patients with malignant ascites," *Eur. J. Surg. Oncol.* 23:526-531 (1997).

Parsons, "An anti-thiamine effect produced in human subjects by bracken ferns," *J. Amer. Dietetic Assoc.* 31:790 (1953).

Pasqualini et al., "Organ targeting in vivo using phage display peptide libraries," *Nature* 380:364-366 (1996).

Pawelek et al., "Tumor-targeted Salmonella as a novel anticancer vector," *Cancer Res.* 57:4537-4544 (1997).

Perales et al., "Gene transfer in vivo: sustained expression and regulation of genes introduced into the liver by receptor-targeted uptake," *Proc. Natl. Acad. Sci. USA* 91:4086-4090 (1994).

Peters, *Biochemical Lesions and Lethal Synthesis* Macmillan: New York 321 (1963).

Piccoli et al., "Chimeric anti-angiogenenin antibody cAb 26-2F inhibits the formation of human breast cancer xenografts in athymic mice," *Proc. Natl. Acad. Sci. USA* 95:4579-4583 (1998).

Platt, "Thiamine deficiency in human beriberi and in Wernicke's encephalopathy," *Thiamine Deficiency* (ed. Wolstenholme et al.) Little Brown: Boston pp. 135-143 (1967).

Pluda, "Tumor-associated angiogenesis: Mechanisms, clinical implications, and therapeutic strategies," *Semin. Oncol.* 24:203-218 (1997).

Pratt et al., *Principles of Drug Action: The basis of pharmacology*, 3rd Ed. Churchill Livingstone: New York (1990).

Presta et al., "Humanization of an anti-vascular endothelial growth factor monoclonal antibody for the therapy of solid tumors and other disorders," *Cancer Res.* 57:4593-4599 (1997).

Puzach et al., "Antivitamin activity of thiaminase from freshwater bicuspid moluscs after parental administration of the enzyme to albino mice," (In Russian) *Vopr. Med. Khim.* 22:769-773 (1976) (Abstract).

Puzach, "Approaches to assessing dynamics of permeability and duratioin of thiaminase I action, administered parenterally to animals," (In Russian) *Vopr. Med. Khim.* 41:43-44 (1995) (Abstract).

Puzach, "The presence of antithiamine factor- thiaminase- in organs of random-bred albino rats and mice," (In Russian) *Vopr. Med. Khim.* 37:82-84 (1991) (Abstract).

Raff, "Social controls on cell survival and cell death," *Nature* 356:397-399 (1992).

Rasmussen et al., "Matrix metalloproteinase inhibition as a novel anticancer strategy: A review with special focus on batimastat and marimastat," *Pharmacol. Ther.* 75:69-75 (1997).

Reddy et al., "Thiaminase system in fresh water mussel (*Lamellidens marginalis*)," *Enzymologia* 12:238-245 (1948).

Reed, "Bcl-2 and the regulation of programmed cell death," *J. Cell Biol.* 124:1-6 (1994).

Reisfeld et al., "Human tumor antigens," *Adv. Immunol.* 40:323-377 (1987).

Retta et al., "Antibody-directed enzyme prodrug therapy (ADAPT)-Evidence for a bystander effect in vitro," *Intern. J. Oncology* 9:557-570 (1996) (Abstract).

Ridder et al., "A COS-cell-based system for rapid production and quantification of scFv:IgCk antibody fragments," *Gene* 166:273-276 (1995).

Riethmuller et al., "Randomized trial of monoclonal antibody for adjuvant therapy of resected Dukes' C colorectal carcinoma," *Lancet* 343:1177-1183 (1994).

Rogers, "General discussion of antithiamin compounds and thiamin antagonists," *Ann N.Y. Acad. Sci.* 378:157-160 (1982).

Rogers, "Thiamine antagonists," *Methods Enzymol.* 18A:245-258 (1970).

Ron et al., "Controlled release of polypeptides from polyanhydrides," *Proc. Natl. Acad. Sci. USA* 90:4176-4180 (1993).

Rubin et al., "Correlation between the anticellular and DNA fragmenting activities of tumor necrosis factor," *Cancer Res.* 48:6006-6010 (1988).

Saltzman et al., "Antitumor mechanisms of attenuated Salmonella typhimurium containing the gene for human interleukin-2: a novel antitumor agent?" *J. Pediatr. Surg.* 32:301-306 (1997).

Sambrook et al., *Molecular Cloning: A Laboratory Manual*, 2nd Ed. Cold Spring Harbor Laboratory Press: Cold Spring Harbor, NY (1989) (Table of contents).

Santos et al., "Rodent pharmacokinetic and anti-tumor efficacy studies with a series of synthetic inhibitors of matrix metalloproteinases," *Clin. Exp. Metastasis* 15:499-508 (1997).

Scherf et al., "Cytotoxic and antitumor activity of a recombinant tumor necrosis factor-B1 (Fv) fusion protein on Le$^Y$ antigen-expressing human cancer cells," *Clin. Cancer Res.* 2:1523-1531 (1996).

Schrier et al., "High dose $^{90}$Y Mx-diethylenetriaminepentaacetic acid (DTPA)-BrE-3 and autologous hematopoietic stem cell support (AHSCS) for the treatment of advanced breast cancer: A phase I trial," *Cancer Res.* 55:5921s-5924s (1995).

Schwartz, "Immunological tolerance," *Fundamental Immunology*, 3rd Ed. (ed. Paul) Raven Press: New York pp. 677-731 (1993).

Sealock et al., "Thiamine inactivation by the fresh-fish or Chastek-paralysis factor," *J. Am. Chem. Soc.* 65:935-940 (1943).

Sears et al., "Phase II clinical trial of murine monoclonal antibody cytotoxic for gastrointestinal adenocarcinoma," *Cancer Res.* 45:5910-5913 (1985).

Seear et al., "Thiamine, riboflavin, and pyridoxine deficiencies in a population of critically ill children," *J. Pediatr.* 121:533-538 (1992).

Sentman et al., "bcl-2 inhibits multiple forms of apoptosis but not negative selection in thymocytes," *Cell* 67:879-888 (1991).

Sharkey et al., "Evaluation of a complementarity-determining region-grafted (humanized) anti-carcinoembryonic antigen monoclonal antibody in preclinical and clinical studies," *Cancer Res.* 55:5935s-5945s (1995).

Sherris, "Normal microbial flora," *Medical Microbiology: An Introduction to Infectious Diseases* Elsevier: New York pp. 50-58 (1984).

Sim et al., "A recombinant human angiostatin protein inhibits experimental primary and metastatic cancer," *Cancer Res.* 57:1329-1334 (1997).

Sinicrope et al., "Increased apoptosis accompanies neoplastic development in the human colorectum," *Clin. Cancer Res.* 2:1999-2006 (1996).

Sivolapenko et al., "Breast cancer imaging with radiolabelled peptide from complementarity-determining region of antitumor antibody," *Lancet* 346:1662-1666 (1995).

Skobe et al., "Halting angiogenesis suppresses carcinoma cell invasion," *Nature Med.* 3:1222-1227 (1997).

Smith et al., "Development of thiamine deficiency in the cat on a diet of raw fish," *Proc. Soc. Exp. Biol. Med.* 56:1-3 (1944).

Smith et al., "Libraries of peptides and proteins displayed on filamentous phage," *Methods Enzymol.* 217:228-257 (1993).

Smith et al., "Rapid identification of highly active and selective substrates for stromelysin and matrilysin using bacteriophage peptide display libraries," *J. Biol. Chem* 270:6440-6449 (1995).

Spitzer et al., "Inactivitation of vitamin $B_1$ by raw fish," *Proc. Soc. Exp. Biol. Med.* 48:376-379 (1941).

Steller, "Mechanisms and genes of cellular suicide," *Science* 267:1445-1449 (1995).

Steyn-Parve, "The mode of action of some thiamine analogues with antivitamin activity," *Thiamine Deficiency* (ed. Wolstenholme et al.) pp. 27-43 Little Brown: Boston (1967).

Szostak, *Redesigning the Molecules of Life* Ed. S. A. Brenner, pp. 87-113, Springer-Verlag Germany (1988).

Szostak, "In vitro genetics," *TIBS* 17:89-93 (1993).

Thomas et al., Inactivation of thiamine by bracken (*Pteris aquilina*) *J. Soc. Chem. Ind.* (Lond.) 68:6-9 (1949).

Thompson, "Apoptosis in the pathogenesis and treatment of disease," *Science* 267:1456-1462 (1995).

Thorpe et al., "Antibody-directed targeting of the vasculature of solid tumors," *Breast Cancer Res. Treat.* 36:237-251 (1995) (Abstract).

Trebukhina et al., "Effect of thiamine and its antimetabolite oxythiamine on the proliferative activity of carcinosarcoma Walker 256 cells," (In Russian) *Eksp. Onkol.* 9:60-63 (1987) (Abstract).

Trebukhina et al., "Level of thiamine diphosphate in the liver of tumor-bearing animals kept on a diet including an excessive amount of vitamin $B_1$," (In Russian) *Vopr. Pitan.* pp. 63-65 (1986) (Abstract).

Trebukhina et al., "Thiamine metabolism in the liver of mice with Ehrlich ascites carcinoma," *Neoplasma* 29:257-268(1982).

Trebukhina, "Transketolase activity and the TDP effect in tissues of animals with experimental tumors," (In Russian) *Vopr. Med. Khim.* 29:85-90 (1983) (Abstract).

Trojan et al., "Treatment and prevention of rat gliobastoma by immunogenic C6 cells expressing antisense insulin-like growth factor I RNA," *Science* 259:94-97 (1993).

Uray et al., "Dual Mechanisms of nucleophilic substitution of thiamin analogs: Estimating the special kinetic effect of sulfite ion," *Bioorg Chem*. 21:294-308 (1993).

Vaish et al., "Isolation of hammerhead ribozymes with altered core sequences by in vitro selection," *Biochemistry* 36:6495-6501 (1997).

Vaux et al., "Bcl-2 prevents death of factor-deprived cells by fails to prevent apoptosis in targets of cell-mediated killing," *Int. Immunol*. 4:821-824 (1992).

Vedder, "The pathology of beriberi," *The Vitamins* (ed. Association, A.M.) American Medical Association: Chicago pp. 179-191 (1939).

Vieweg et al., "Efficient gene transfer with adeno-associated virus-based plasmids complexed to cationic liposomes for gene therapy of human prostate cancer," *Cancer Res*. 55:2366-2372 (1995).

Vimokesant et al., "Effect of tea consumption on thiamine status in man," *Nutr. Rep. Int*. 9:371-374 (1974) (Abstract).

Vitetta et al., "Immunotoxins: Magic bullets or misguided missles?" *Trends Pharmacol. Sci*. 14:148-154 (1993).

Von Muralt, "Thiamine and peripheral neurophysiology," *Vitamins and Hormones* 5:93-118 (1947).

Waldmann, "Monoclonal antibodies in diagnosis and therapy," *Science* 252:1657-1662 (1991).

Wamil et al., "Soluble E-selectin in cancer patients as a marker of the therapeutic efficacy of CM101 a tumor-inhibiting anti-neovascularization agent, evaluated in phase I clinical trial," *J. Cancer Res. Clin. Oncol*. 123:173-179 (1997).

Waring, "DNA fragmentation induced in macrophages by gliotoxin does not require protein synthesis and is preceded by raised inositol triphosphate levels," *J. Biol. Chem*. 265:14476-14480 (1980).

Watanabe et al., "Studies on the nutritional value of the fern, IV. The effect of the ingestion of bracken on man," *Kokumin Eisei* 21:137 (1955) (Abstract).

Watson et al., "Ch. 28. Working toward human gene therapy," *Recombinant DNA*, 2nd Ed. Scientific American Books: New York pp. 567-581 (1992).

Watt et al., "Human prostate-specific antigen: Structural and functional similarity with serine proteases," *Proc. Natl. Acad. Sci. USA* 83:3166-3170 (1986).

Weiner et al., "Oral tolerance: Immunologic mechanisms and treatment of animal and human organ-specific autoimmune diseases by oral admininstration of autoantigens," *Annu. Rev. Immunol*. 12:809-837 (1994).

Wenckebach, St. Cyres lecture on heart and circulation in tropical avitaminosis (beri-beri) *Lancet* 2:265-268 (1928).

Wentworth et al., "Toward antibody-directed "abzyme" prodrug therapy, ADAPT: Carbamate prodrug activation by a catalytic antibody and its in vitro application to human tumor cell killing," *Proc. Natl. Acad. Sci. USA* 93:799-803 (1996).

Werthle et al., "Local administration of 7β-hydroxycholestery1-3-oleate inhibits growth of experimental rat C6 glioblastoma," *Cancer Res*. 54:998-1003 (1994).

Weswig et al., "Antithiamine activity of plant materials," *J. Biol. Chem*. 165:737-738 (1946).

White, "Death-defying acts: a meeting review on apoptosis," *Genes Dev*. 7:2277-2284 (1993).

Williams et al., "Studies on crystalline vitamin $B_1$. III. Cleavage of vitamin with sulfite," *J. Am. Chem. Soc*. 57:536-537 (1935).

Williams et al., "Ch. XXII. Thiamin requirement in relation to special circumstances," *Vitamin $B_1$ (Thiamine) and its use in medicine* Macmillan: New York pp. 280-299 (1938).

Williams, *Toward the conquest of Beriberi* Harvard University Press: Cambridge (1961) (Table of Contents Only).

Wilson et al., "In vitro evolution of a self-alkylating ribozyme," *Nature* 374:777-782 (1995).

Wilson et al., "Ex vivo gene therapy of familial hypercholesterolemia," *Hum. Gene Ther*. 3:179-222 (1992) (Abstract).

Winter et al., "Humanized antibodies," *Trends Pharm. Sci*. 14:139-143 (1993).

Winter et al., "Making antibodies by phage display technology," *Annu. Rev. Immunol*. 12:433-455 (1994).

Wittliff et al., "The extracellular thiaminase I of *Bacillus thiaminolyticus*. I. Purification and physiochemical properties," *Biochem* 7:736-744 (1968).

Wittliff et al., "Thiaminase I," *Methods Enzymol*. 18:229-234 (1970).

Wittliff et al., "Thiaminase II " *Methods Enzymol*. 18:234-238 (1970).

Wolff et at., "Direct gene transfer into mouse muscle in vivo," *Science* 247:1465-1468 (1990).

Woolley et al., "Demonstration by the aid of pyrithiamins of a new action of thiamine," *Bull. Soc. Chim. Biol*. 36:1207-1212 (1954).

Woolley et al., "Production of thiamine deficiency disease by the feeding of a pyridine analogue of thiamine," *J. Biol. Chem*. 149:285-289 (1943).

Woolley, An enzymatic study of the mode of action of pyrithiamine (neopyrithiamine) *J. Biol. Chem*. 191:43-54 (1951).

Woolley, "Biosynthesis and energy transport by enzymatic reduction of onium salts," *Nature* 171:323-328 (1953).

Woolley, "Destruction of thiamin by a substance in certain fish," *J. Biol. Chem*. 141:997-998 (1941).

Woolley, "Enzymatic synthesis of folic acid by the action of carp thiaminase," *J. Am. Chem. Soc*. 73:1898 (1951).

Wu et al., "Receptor-mediated gene delivery in vivo," *J. Biol. Chem* 266:14338-14342 (1991).

Wu et al., "Receptor-mediated in vitro gene transformation by a soluble DNA carrier system," *J. Biol. Chem*. 262:4429-4432 (1987).

Wyatt et al., "Factors affecting a cyanogen bromide-based assay of thiamin," *Clin. Chem*. 35:2173-2178 (1989).

Wyllie et al., "Cell death: The significance of apoptosis," *Intern. Rev. Cytol*. 68:251-306 (1980).

Wyllie, "The biology of cell death in tumours," *Anticancer Res*. 5:131-136 (1985).

Xu et al., "Gene therapy with P53 and a fragment of thrombospondin I inhibits human breast cancer in vivo," *Mol. Genet. Metab*. 63:103-109 (1998) (Abstract).

Yang et al., "In vivo and in vitro gene transfer to mammalian somatic cells by particle bombardment," *Proc. Natl. Acad. Sci*. 87:9568-9572 (1990).

Yoneda et al., "Expression of angiogenesis-related genes and progression of human ovarian carcinomas in nude mice," *J. Natl. Cancer Inst*. 90:447-454 (1998).

Yu et al., "Prostate-specific antigen is a new favorable prognostic indicator for women with breast cancer," *Cancer Res*. 55:2104-2110 (1995).

Yudkin, "Thiaminase, the Chastek-paralysis factor," *Physiol. Rev*. 29:389-402 (1949).

Zhang et al., "Excitotoxic cytopthology, progression and reversibility of thiamine deficiency-induced diencephalic lesions," *J. Neuropathol. Exp. Neurol*. 54:255-267 (1995).

Zhu et al., "Systemic gene expression after intravenous DNA delivery into adult mice," *Science* 261:209-211 (1993).

Zhuang et al., "Apoptin, a protein derived from chicken anemia virus, induces p53-independent apoptosis in human osteosarcoma cells," *Cancer Res*. 55:486-489 (1995).

Ziche et al., "Linomide blocks angiogenesis by breast carcinoma vascular endothelial growth factor transfectants," *Br. J. Cancer* 77:1123-1129 (1998).

Zimatkina et al., "Antitumor activity of hydroxythiamine and methotrexate immobilized on monocarboxycellulose," *Pol. J. Pharmacol*. 48:163-169 (1996).

Zimatkina et al., "Comparative evaluation of the action of oxythiamine and its derivatives on animals with Erhlich's ascitic cancer," (In Russian) *Eksp. Onkol*. 8:68-70 (1986) (Abstract).

Agren, G., "On the Purification of the Thiamin-Inactivating Fish Factor," *Thiamin-Inactivating Fish Factor*, Dept. of Medical Chemistry; pp. 307-312 (1945).

Altschul, et al., "Gapped BLAST and PSI-BLAST: a new generation of protein database search programs," *Nucleic Acids Research*, 25(17):3389-3402 (1997).

Barettino, et al., "Improved method for PCR-mediated site-directed mutagenesis," *Nucleic Acids Research*, 22(3):541-542 (1994).

Berges, et al., "Implication of Cell Kinetic Changes during the Progression of Human Prostatic Cancer[1]," *Clinical Cancer Research*, 1:473-480 (1995).

Bettendorff et al., "Mechanism of thiamine transport in neuroblastoma cells." J.Biol. Chem., 269(20):14379-14385, (1994).

Bos & Kozik, "Some Molecular and Enzymatic Properties of a Homogeneous Preparation of Thiaminase I Purified from Carp Liver," *Journal of Protein Chemistry, 19*(2):75-84 (2000).

Budavari et al., Merck Index, 11th edition, New Jersey, p. 1464, (1989).

Chait & Kent, "Weighing Naked Proteins: Practical, High-Accuracy Mass Measurement of Peptides and Proteins," *Science, 257*:1885-1893 (1992).

"Clostridium." Encyclopedia Britannica 2003 Encyclopedia Britannica Online. Jan. 30, 2003 http://www.search.eb.com/eb/article?eu=24827.

Dang, et al., "Combination bacteriolytic therapy for the treatment of experimental tumors," *PNAS, 98*(26):15155-15160 (2001).

Dempster, et al., "Rapid DNA Extraction from Ferns for PCR-Based Analyses," *BioTechniques, 27*(1):66-68 (1999).

Huang & Miller, "A Time-Efficient, Linear-Space Local Similarity Algorithm," *Advances in Applied Mathematics, 12*:337-357 (1991).

Kimura et al., "Separation and determination of thiamine-binding proteins in rats by high-performance liquid chromatography." J. Chrom., 211: 290-294, 1981.

Kowit & Fulton, "Purification and Properties of Flagellar Outer Doublet Tubulin from *Naegleria gruberi* and a Radioimmune Assay for Tubulin," *The Journal of Biological Chemistry, 249*(11):3638-3646 (1974).

Lai, et al., "The β-Tubulin Gene Family Expressed during Cell Differentiation in *Naegleria gruberi*," *The Journal of Cell Biology, 106*:2035-2046 (1988).

Low, et al., "Lipid A mutant *Salmonella* with suppressed virulence and TNFβ induction retain tumor-targeting in vivo," *Nature Biotechnology, 17*:37-41 (1999).

Moese & Moese, Oncolysis by Clostridia. I. Activity of *Clostridium butyricum* (m-55) and other Nonpathogenic Clostridia against the Ehrlich Carcinona, Cancer Research, 24:212-216 (1964).

Nishimune, et al., "Thiamin Is Decomposed Due to *Anaphe* spp. Entomophagy in Seasonal Ataxia Patients in Nigeria[1]," *J. Nutr., 130*(6):1625-1628, (2000).

Palu et al., In pursuit of new developments for gene therapy of human diseases, Journal of Biotechnology, 68:1-13, 1999.

Pearson & Lipman, "Improved tools for biological sequence comparison," *Proc. Natl. Acad. Sci. USA, 85*:2444-2448 (1988).

Rood, et al., The Clostridia: Molecular Biology and Pathogenesis, Title and Table of Contents, Academic Press, San Diego, 1997.

Romano et al., Latest developments in gene transfer technology: Achievements, perspectives and controversies over therapeutic applications, Stem Cells, 18:19-39, 2000.

"Saimonella." Encyclopedia Britannica 2003 Encyclopedia Britannica Online. Jan. 30, 2003 <http://www.search.eb.com/eb/article?eu=6793>.

Salamov, et al., "Combining sensitive database searches with multiple intermediates to detect distant homologues," *Protein Engineering, 12*(2):95-100 (1999).

Southern, E.M., "Detection of Specific Sequences Among DNA Fragments Separated by Gel Electrophoresis," *J. Mol. Biol., 98*:503-517 (1975).

Umekita, et al., "Human prostate tumor growth in athymic mice: Inhibition by androgens and stimulation by finasteride," *Proc. Natl. Acad. Sci. USA, 93*:11802-11807 (1996).

Wiemann & Starnes, "Coley's Toxins, Tumor Necrosis Factor and Cancer Research: A Historical Perspective," *Pharmac. Ther., 64*:529-564 (1994).

Wu, et al., "Mechanistic Studies on Thiaminase I: Identification of the Product of Thimain Degradation in the Absence of the Nucleophilic Cosubstrate," *Bioorganic Chemistry, 8*:45-48 (2000).

Yang et al., "Antithiamin activity of polyphenolic antioxidants." J. Food Sci., 49:489-492, 1984.

Abdel-Nabi, et al., "Monoclonal Antibodies and Radioimmunoconjugates in the Diagnosis and Treatment of Prostate Cancer," *Semin. Urol.* 10:45-54 (1992).

Abe, et al., "A Simple Method For The Detection of Two Types of Thiaminase-Producing Colonies," *FEMS Microbial. Lett.*, "A Simple Method for the Detection of Two Types of Thiaminase-Producing Colonies," *FEMS Microbiol. Lett.*, 34:129-133 (1986).

\* cited by examiner

METHOD OF INDUCING APOPTOSIS BY REDUCING THE LEVEL OF THIAMIN

RELATED APPLICATIONS

This application is a continuation of Perlman et al., U.S. application Ser. No. 09/113,596, filed Jul. 10, 1998, now U.S. Pat. No. 6,506,550, which claims the benefit of Perlman et al., Provisional Application 60/087,526, filed Jun. 1, 1998, and of Perlman et al., Provisional Application 60/052,377, filed Jul. 11, 1997, all of which are incorporated herein by reference in their entireties.

BACKGROUND OF THE INVENTION

The invention is related to the field of treatment of cancer, other neoplastic disorders, and other conditions in vertebrates in which killing a specific group of cells is useful.

Most if not all cells of metazoan animals carry the machinery to commit suicide in a regular manner in response to suitable stimulus. This process is called programmed cell death, cell suicide, or apoptosis. Apoptosis is being extensively studied in mammals and other vertebrates, as well as in the worm *Caenorhabditis elegans* and the fly *Drosophila melanogaster* (reviews: Ellis et al., 1991; Steller, 1995). In vertebrate cells the process of apoptosis, which was previously termed "shrinkage necrosis," involves a regular sequence of events, including membrane blebbing, cell shrinkage, pycnosis of nuclei with margination of chromatin, and usually cleavage of DNA into nucleosome-sized fragments (Wyllie et al., 1980).

Apoptosis is an essential part of embryonic development and of the maintenance of an adult animal. In mammals, for example, during development apoptosis plays a major role in the development of the nervous system (more than 50% of the neural cells that arise during embryogenesis undergo apoptosis), in the elimination of lymphocytes that produce antibodies which recognize self, in "carving" features such as the digits of the hand, and so forth. Throughout life, orderly apoptosis is used to eliminate damaged or unwanted cells without inducing an inflammatory reaction. Blood cells, cells of the immune system, and cells of most if not all tissues normally are eliminated by the apoptotic mechanism.

Failures of apoptosis produce or contribute to severe diseases, including autoimmune diseases and some cancers. It has been argued that one of the major causes of the development and progression of many cancers is a reduction of the occurrence of apoptosis (Wyllie, 1985; Fisher, 1994; Hickman et al., 1994; Martin and Green, 1995; Thompson, 1995).

A wide variety of signals induce apoptosis in suitable target cells (Gerschenson and Rothello, 1992; Thompson, 1995). Radiation and many valuable chemotherapeutic agents, such as cisplatin and other platinum compounds, induce apoptosis (e.g., Eastman, 1990; Hickman, 1992; Chu, 1994a). These agents affect many cell types. Specialized cell types are dependent on specific growth factors (e.g., nerve growth factor for certain neuronal cells, interleukin-2 for certain lymphocytes) and undergo apoptosis if the required factors are unavailable. Other cell types have receptors for specific agents that can induce apoptosis in these cell types (e.g., glucocorticoid for thymocytes, tumor necrosis factor in suitable target cells) (e.g., Rubin et al., 1988).

The mechanism of apoptosis is just beginning to be understood. Some have suggested that all cells are poised to die, and that they are kept alive by constant "survival signals" that keep the suicide machinery inactive (Raff, 1992). It is clear that many if not all vertebrate cells contain preformed machinery for apoptosis, since there are many examples of cells that undergo apoptosis even without synthesis of new proteins (Waring, 1990). There also are cases in which protein synthesis is required (reviewed by Cohen, 1993).

Several elements that appear to be part of the apoptotic machinery have been identified and are receiving much attention. Two that should be mentioned are bcl-2 and its family members and p53. Exactly how these are related to the apoptotic machinery is still being defined.

Expression of oncogene bcl-2 in cells markedly delays or blocks induction of apoptosis by many agents, including some that are valuable in chemotherapy of tumors, such as cisplatin (Reed, 1994; Korsmeyer, 1995; Thompson, 1995). There are a few cases in which induction of apoptosis is unaffected by expression of bcl-2 (e.g., Sentman et al., 1991; Vaux et al., 1992). High-level expression of bcl-2 is common in tumors, including breast carcinomas, small cell lung cancer, androgen-independent prostate cancer, and neuroblastoma (Hickman et al., 1994). In some cases expression of bcl-2 is correlated with a poor prognosis for therapy (Reed, 1994).

Functional tumor suppressor gene product p53 is required for induction of cell death by irradiation and many chemotherapeutic agents (Lowe et al., 1993), as well as by oxygen deficiency at the center of solid tumors (Graeber et al., 1996). On the other hand, the normal development of transgenic animals nullizygous for the p53 gene indicates that p53 is not required for the extensive apoptosis that occurs during development (Donehower et al., 1992). Other cases of p53-independent apoptosis have been described (White, 1993; Zhuang et al., 1995). Many established lines of cells in culture have lost p53 function. In tumors in vivo, loss of p53 function is common, and this loss is correlated with tumor aggressiveness and indicates a poor prognosis for treatment by standard protocols of chemotherapy and radiation (Fisher, 1994; Hartmann et al., 1997).

As an example, the roles of p53 loss and bcl-2 expression in the development and progression of colon carcinomas have been described and analyzed (Hickman et al., 1994; Sinicrope et al., 1996).

SUMMARY

The present invention is based on our discovery that apoptotic cell death can be induced in diverse cell types by creating a deficiency in the natural vitamin, thiamin. The invention provides a method for inducing death in selected cells in vivo by using localized delivery of thiamin-depleting compounds to reduce the thiamin in these cells below a critical level. This method, localized apoptosis induced by depletion of thiamin (LAIDT), is applicable to therapy of cancer and to elimination of other targetable cells. Furthermore, the method allows rapid and convenient reversal of the effects of the deficiency at any time such reversal is desired, simply by the administration of replacement thiamin.

This method allows the selective killing of a group of cells, for example a tumor mass, by localizing the deficiency of thiamin to the desired cell group. As described below, both the thiamin depletion and the targeting can be accomplished in a variety of different ways. Typically however, the method involves the delivery of a thiamin-depleting agent or a nucleic acid sequence encoding a thiamin-depleting agent to the desired cell group. The creation of the thiamin deficiency, which results from the delivery of the thiamin-depleting agent, leads to programmed cell death, or apoptosis. This method is broadly applicable to use with cells of vertebrate organisms, which cannot produce their own thiamin and so rely on exogenously provided, i.e., dietary, thiamin to provide the cellular requirements. In particular, the method can be utilized in vivo in a vertebrate organism, for example a human.

This invention utilizes a novel paradigm for cancer therapy, in addition to those currently commonly used or tested (e.g., radiation, chemotherapy, immunotherapy, gene therapy, anti-angiongenesis therapy). In this paradigm, selective starvation of cancer cells for a particular required nutrient whose absence induces apoptosis, in this description the essential vitamin thiamin, leads to death of the cancer cells.

Thus in a first aspect, the invention provides a method for inducing apoptosis of a selected group of vertebrate cells in vivo by sufficiently reducing the level of thiamin in cells of the group. For example, the cells may be neoplastic cells, e.g., cancer cells.

The term "apoptosis" refers to the process of programmed cell death, with its accompanying cellular morphological changes and loss of cell viability. This does not mean however that all methods of inducing apoptosis or the mechanisms of cell death associated with different induction methods are the same.

In the context of this method, the term "inducing" means a direct or indirect causal relationship. Thus, the presence and/or maintenance of a particular condition causes or leads to the induced result.

The term "vertebrate organism", as is commonly understood, refers to an animal which has a spinal column, such as birds and mammals, and specifically includes humans.

The term "group of vertebrate cells" refers to a subset of the cells of a vertebrate organism, and thus includes cells of a human. Such a subset may, for example, be a particular tissue or localized portion of a tissue, an organ or portion of an organ, or a solid tumor. The term may also refer to cells of a particular type, for example, dispersed tumor cells. The term "selected" indicates that the group of cells in which apoptosis was to be induced was chosen prior to reduction of the level of thiamin.

The term "in vivo" indicates that the thiamin depletion portion of the method is carried out on cells within a living organism. However, some steps or portions of steps of the described methods may be performed outside the organism. An example could be the preparation of compositions containing thiamin-depleting agents.

The phrase "reducing the level of thiamin" means that the average concentration of thiamin in a group of cells is reduced. "Reducing the level of thiamin" further means that the average cellular concentration of thiamin in the affected group of cells is made lower than it would have been without the initiation of the method of this invention, with conditions otherwise being the same.

The term "sufficiently" indicates that the thiamin is reduced to a level at least low enough to result in the induction of apoptosis. Thus, the term indicates a functional requirement for the level of reduction. In general, this sufficient reduction can be determined empirically by standard methodology.

In general, the reduced-level of thiamin for a group of cells should be maintained throughout a latent period for apoptosis of the group of cells to occur. Therefore in preferred embodiments, the reduced level of thiamin is maintained for as long as is necessary to obtain a therapeutic effect, generally by achieving death of the target cells. As indicated by in vitro results, this is likely to be at least about six days, and probably longer before treated cells, preferably all treated cells, in a population are killed. Therefore, in preferred embodiments, a reduced level of thiamin is maintained for about 3-100 days, more preferably about 3-60 days, and still more preferably about 3-45 days. However, in some applications sufficient reduction of the level of thiamin will be achieved within other, preferably shorter times, so in other preferred embodiments, a reduced level of thiamin is maintained for about 4-30 days, more preferably about 4-20 days, 6-20 days, 1045 days, or 10-30 days.

For the methods of this invention, a "therapeutic effect" refers to an effect on a treated organism in which at least a portion of the targeted cells are killed. For the treatment of a disease or condition, a therapeutic effect preferably also results in at least a temporary alleviation of at least one symptom or reduces the severity of the disease or condition. Thus, therapeutic effects can include both temporary or transient effects and permanent effects, which can include a cure.

In some circumstances, it will be easier to maintain a sufficiently low level of thiamin in the selected group of cells if the cells of the organism as a whole are partially depleted of thiamin. In this way, the additional localized thiamin depletion that is needed is lessened. Thus in preferred embodiments, the method also involves partially depleting the organism of thiamin, preferably by providing a thiamin restricted diet to the organism. In this way the amount of available thiamin is reduced.

The term "thiamin restricted diet" means that the total dietary thiamin intake of the organism is sufficiently reduced over a period of time so that the total cellular thiamin content of the organism is reduced below the level which would be present with a normal dietary intake of thiamin.

In this context, "available thiamin" refers to thiamin which is in a form and location such that it can be taken up by a cell or group of cells and utilized within the cell or cells.

In preferred embodiments, the level of thiamin in the selected group of cells is reduced by administering at least one thiamin-depleting agent.

A "thiamin-depleting agent" is a compound which inactivates or inhibits the cellular utilization of thiamin under physiological conditions. Such an inactivation can result from various mechanisms, including, for example, cleavage, chemical modification, and sequestering of thiamin molecules. Inactivation can also occur either extracellularly or intracellularly. Inhibiting the cellular utilization of thiamin can also take place through various mechanisms, including, for example, inhibition of uptake, competitive binding, inhibition of an enzyme which has thiamin as a substrate or co-enzyme, and inhibition of an enzyme which is necessary for the cellular utilization of thiamin, but which does not directly have thiamin as a substrate or co-enzyme.

The thiamin-depleting agent of this invention can be of various types including polypeptides, peptides, chemically modified peptides or polypeptides, and various classes of peptidomimetic and other synthetic compounds, including, e.g., engineered ribozymes. In some embodiments, the agent is a chemical analogue of thiamin. Also in some embodiments, the agent is a small molecule.

The term "small molecule" indicates that the molecule has a molecular weight of less than about 5,000 Daltons, preferably less than about 3,000 Daltons, more preferably less than about 2,000 Daltons, still more preferably less than about 1,000 Daltons, and most preferably less than about 600 Daltons.

A variety of different types of thiamin-depleting agents can be utilized, thus in preferred embodiments the thiamin-depleting agent is a thiamin-cleaving compound, such as a thiaminase or thiaminase derivative, or a thiamin binding compound, or a thiamin antagonist such as a thiamin antimetabolite.

In reference to thiamin-depleting agents, a "synthetic compound" is a compound which has a chemical structure different from a naturally occurring compound such as thiamin, thiaminase or a naturally-occurring thiamin-binding compound or other naturally occurring protein or polypeptide having thiamin-depleting activity. In the case of synthetic polypeptide agents, they may be prepared by expression from a nucleic acid sequence, but the sequence of the synthetic polypeptide differs from the sequence of a naturally occurring thiamin-depleting agent. Such a synthetic agent may include, for example, the catalytically active portion of a naturally occurring thiaminase. It may also include a compound prepared, at least in part, by chemical synthesis methods, such as a peptidomimetic compound. A "fully synthetic" compound is a synthetic compound which is prepared, at least in part, by chemical synthetic methods rather than synthesis by expression from a nucleic acid sequence encoding a thiamin-depleting agent. In the case of fully synthetic polypeptide agents, the fully synthetic compound does not include an amino acid sequence which has an identical amino acid sequence as a portion at least 10 amino acids in length of a naturally occurring thiamin-depleting agent which would retain the thiamin-depleting activity, such as a catalytically active portion of a naturally occurring thiaminase. Thus, synthetic compounds include synthetic thiaminases.

Also in preferred embodiments, a polypeptide thiamin-depleting agent can be expressed from a recombinant gene or nucleic acid sequence, in which case both the nucleic acid sequence and the encoded thiamin-depleting agent can be regarded as a thiamin-depleting agent. This includes for example, expression of a thiaminase or other thiamin-depleting agent from such a nucleic acid sequence in a vertebrate organism. Preferably, for such gene therapy, the sequence encoding the thiamin-depleting agent is on a vector, preferably an expression vector, and most preferably a eukaryotic expression vector. The vector can, for example, be a retroviral vector or a plasmid vector In preferred embodiments, the methods involving nucleic acid sequences also utilize other components which are preferably associated with the nucleic acid sequence, for example, those described below for methods for delivering a nucleic acid sequence encoding a thiamin-depleting agent to vertebrate cells. In addition, the nucleic acid sequence can be provided in a composition which includes a protective component, for example, a liposome or a biodegradable nanoparticle.

In connection with delivery of thiamin-depleting agents or nucleic acid sequences encoding thiamin-depleting agents, the term "protective component" refers to a compound or preferably a physical structure which protects the agent or nucleic acid from degradation or inactivation in vivo in a vertebrate animal. Examples include liposomes, lipid/nucleic acid complexes, biodegradeable nanoparticles or nanospheres, and nucleic acid binding compounds which coat or surround nucleic acid molecules such as DNA.

In connection with nucleic acid sequences, use of the term "recombinant" indicates that the sequence has been transferred into or recombined into a different nucleic acid molecule. Thus, for example, a sequence encoding a thiaminase can be transferred into the nucleic acid molecule of an expression vector such as a plasmid, and is then a recombinant sequence.

A "vector" refers to a structure consisting of or including a nucleic acid molecule which is suitable for transferring genetic material into a cell. Typically a selected nucleic acid sequence is inserted into the nucleic acid molecule of the vector. Examples include plasmid and viral vectors.

An "expression vector" is a vector constructed and adapted to allow expression of an inserted nucleic acid coding sequence in a cell. Thus, the vector includes nucleic acid sequences which allow initiation of transcription in an appropriate location with respect to the coding sequence. Expression vectors can be adapted for expression in prokaryotic or eukaryotic cells, thus, a "eukaryotic expression vector" is constructed to allow expression of a coding sequence in a eukaryotic cell.

The term "thiamin-cleaving compound" refers to a compound which is able to interact with the thiamin molecule in solution under approximately physiological conditions and cause cleavage of the thiamin molecule into at least two discrete portions. The thiamin-cleaving compound can, for example, interact with the thiamin molecule in an enzymatic interaction or can directly react with the thiamin.

Thiaminases, as found in scattered groups of organisms, are a useful natural starting point to obtain thiamin-cleaving compounds to use to induce apoptosis by reducing the level of thiamin in the environment of selected cells. In addition to the naturally occurring thiaminases, a variety of modifications and derivatives can be constructed which can have advantageous properties for use as therapeutic compounds. In general such changes are directed to making a compound which is more stable in vivo and/or which is more readily administered. A useful approach for making such changes is to trim down a naturally occurring thiaminase to identify a functional core or reduced length sequence which retains thiamin-cleaving activity in order to minimize the probability or rate of destruction of the molecule in the body of a treated animal. Such size reduction can also reduce the antigenic potential of the molecule and can aid in penetration of the molecule into in vivo sites, such as the interior of a solid tumor. Alternatively or in addition, amino acid substitutions or chemical modifications can be incorporated, which can reduce the rate of in vivo destruction. Thus, the methods of the present invention encompass the use of naturally occurring thiaminases, modified thiaminases, and thiaminase derivatives.

The natural thiaminases can also be used to design synthetic or artificial thiamin-cleaving compounds, which can be regarded as synthetic or artificial thiaminases. Based on comparison of a variety of thiaminases and the structural requirements for thiamin-cleaving function, such as structural studies of the active sites, synthetic thiaminases can be constructed. For example, peptides of small, or minimal size, can be constructed having thiamin-cleaving activity using this approach. Preferably such peptides will have less than about 200 amino acid residues, more preferably less than about 100, still more preferably less than about 75, and most preferably less than about 50 or even 20 amino acid residues. Such peptides can be prepared by chemical synthesis or by expression from nucleic acid sequences encoding the amino acid sequence. Chemical modifications of one or more amino acids can also be incorporated.

The term "synthetic thiaminase" refers to a thiamin-cleaving compound which preferably is structurally based on the catalytic site of a natural or reduced size thiaminase, but which has a different chemical structure than the natural active site. Thus, the synthetic thiaminase can have a different amino acid sequence, or can include non-natural amino acids, or can include non-amino acid structures, or can have a completely non-amino acid structure. Alternatively, a synthetic thiaminase may have a structure unrelated to the catalytic site of a natural thiaminase, but the molecule has a thiamin-cleaving activity. A "synthetic thiamin-binding compound" is similarly related to naturally occurring or reduced sized polypeptide thiamin-binding compounds.

The structural and functional analysis can also be used to construct artificial thiaminases, which incorporate non-natural amino acids and/or other chemical structures, but which also specifically cleave thiamin. Such compounds can be termed peptidomimetics, as they mimic the function and structure of a peptide or polypeptide. While such compounds can be obtained in many different ways, one useful approach is to use a combinatorial approach to synthesize libraries of potential thiamin-cleaving compounds based on the active sites of thiaminases. These libraries can then be tested for activity against thiamin and for the ability to induce apoptosis. The incorporation into the molecule of elements which are not natural amino acids allows particular properties of the compound to be enhanced. Such properties can include in vivo stability against degradation (chemical or physical), improved penetration of cells or tissues, and decreased antigenicity.

A similar approach is also applicable to other naturally occurring polypeptide thiamin-depleting agents, for example, to naturally occurring polypeptide thiamin-binding compounds. As with the thiaminases, the naturally occurring thiamin-binding compounds can be trimmed down to identify reduced or minimal size thiamin-binding portions, which can be further modified with the incorporation of non-natural amino acids or other chemical modifications. Also as above, identification of the structure of the binding region allows the design and construction of synthetic peptides or peptidomimetic compounds based on that structure.

As used herein, the term "thiaminase" refers to a polypeptide molecule which is a naturally occurring thiamin-cleaving enzyme, or which is a modification of such an enzyme. Examples of naturally occurring thiaminases are described below in the Detailed Description. A modified thiaminase is based on a naturally occurring thiaminase but contains one or more modifications to the amino acid sequence of the polypeptide. Such changes can include the addition or deletion of one or more amino acids, the substitution of one or more amino acids with other amino acids or combinations of such changes, and chemical modification of one or more amino acid residues. Changes of these types can, for example, be used to provide one or more functional advantages over a corresponding natural thiaminase, including, for example, increased stability to enzymatic or chemical degradation, decreased antigenicity, and improved penetration of the modified thiaminase among target cells.

For amino acid additions, in preferred embodiments the addition is a terminal addition providing an amino acid sequence which has a functionality different from a thiaminase, for example, a cell targeting function. For deletions, the resulting modified thiaminase retains the thiamin-cleaving activity of the natural thiaminase. In some embodiments, a modified thiaminase having a deletion preferably contains the majority of the amino acid sequence of the corresponding naturally occurring thiaminase, for example, the deletion may be less than 40%, 30%, 20%, 10%, 5%, or 2% of the naturally occurring thiaminase. Combinations of amino acid additions and deletions may also be present in the same modified thiaminase. For amino acid substitutions, the substitution does not destroy the thiamin-cleaving activity of the modified thiaminase, preferably the modified thiaminase has substantially the activity of the corresponding natural thiaminase. Such substitutions preferably are present in only a small number of sites in the modified thiaminase, for example, in less than 10%, 5%, or 1% of the sites of the naturally occurring thiaminase. In addition to the above changes, a thiaminase may also be modified by chemical modification of one or a few amino acid residues of the molecule. Preferably, but not necessarily, such modification occurs at less than 10%, 5%, or 1% of the amino acid residues. In all of the cases, the thiaminase or modified thiaminase has a thiamin-cleaving activity.

A "thiaminase derivative" refers to a compound which is a polypeptide which includes a sequence of amino acids similar to at least a portion of a natural thiaminase and which retains thiamin-cleaving activity, but which has one or more modifications from the natural thiaminase. One type of derivative corresponds to a portion of a natural thiaminase. This means that the derivative is based on the amino acid sequence of one or more linear parts of the natural thiaminase but less than the full molecule, and retains thiamin cleaving activity. Thus, the derivative may be a linear fragment of the thiaminase or a combination of more than one linear fragments joined together. The derivative may, for example, include at least 20%, 40%, 60% or more of the amino acid sequence of the corresponding naturally occurring thiaminase. In thiaminase derivatives, the amino acid sequence can also be modified, such as by the substitution, deletion, or insertion of one or a few amino acids or combinations of these. Derivatives can also have other modifications. For example, non-natural amino acids can be utilized and side chain modification of natural amino acids can be performed as understood by those skilled in the art. Such modifications can, for example, result in greater resistance to protease cleavage. In certain derivatives, combinations of the above changes may be utilized.

A "thiamin-binding compound" refers to a compound which preferentially forms a stable association with thiamin in approximately physiological conditions. The association is sufficiently stable to effectively sequester thiamin. For compounds to be used in the methods of this invention for inducing apoptosis, the association effectively prevents a cell from utilizing the sequestered thiamin. As with the description of thiaminase above, the term "thiamin-binding compound" includes modifications of the naturally occurring molecule.

The term "thiamin-binding compound derivative" refers to a compound which is related to a naturally occurring thiamin-binding compound in the manner indicated for thiaminases and thiaminase derivatives above.

"Thiamin antagonist" refers to a compound which has an activity in a cell antagonistic to the cellular utilization of thiamin without altering or sequestering thiamin. Thus, the anti-thiamin activity of the compound is not primarily due to a thiamin-cleaving or thiamin-binding activity. An example of such a compound is a "thiamin analogue" or "thiamin antimetabolite". Such an analogue has sufficient structural similarity to thiamin to compete for binding with thiamin and thereby inhibit the cellular uptake or utilization of thiamin. In most cases the activity of an analogue will be due to the binding competition, however, such an analogue may also alter a cellular molecule necessary for the cellular uptake or utilization of thiamin.

In many applications, it is beneficial for the thiamin-depleting agent to act preferentially or exclusively on the selected group of cells. Such preferential activity or selectivity can be provided by targeting the agent to the selected group of cells. Preferably the selected group of cells are cells of a tumor or vascular epithelial cells, or tumor vascular epithelial cells. Targeting can be accomplished by a number of different approaches, which include both molecular targeting approaches and physical targeting approaches and combinations of these. Therefore, in preferred embodiments, such targeting is provided. Such targeting can be provided by a variety of different mechanisms, including but not limited to localized administration of the agent, localized activation of the agent, localized expression of a nucleic acid sequence encoding the agent, and localized binding of the agent or an associated targeting molecule. A number of examples are described in the Detailed Description below.

In the context of the present methods, "localized" means that the action occurs to a greater degree in or at restricted locations, preferably to a much greater degree, rather than at other locations throughout the body of an organism. This does not mean that the action occurs at only a single location. Generally the locations are selected as having a particular property or properties, e.g., locations surrounding the site or administration of a compound, or the locations of cells which have particular surface protein.

In connection with two molecules, the term "associated" refers to a direct or indirect physical interaction such that the two molecules remain in proximity to each other or to a complex including the two molecules to a greater extent or for a longer time than non-associated molecules. Preferably the association is due to interactions such as binding, of any type, or encapsulation.

As indicated, targeting can be provided by a "targeting molecule" or "targeting compound". Such a molecule can, in certain embodiments, be free of covalent bonding with other molecules, or can be covalently linked with a thiamin-depleting agent or another component of a composition for delivery of a thiamin-depleting agent or nucleic acid encoding a thiamin-depleting agent to a cell. Thus, a "targeting molecule" or "targeting compound" is a molecule which has structural characteristics which cause the molecule to preferentially locate to a limited in vivo location or type of location. Preferably and most commonly, the preferential locating is due to specific or preferential binding of the targeting molecule to a particular molecule in the organism which is exclusively or at least predominantly found in association with a particular group of cells. However, other distributions or interactions can also be used, such as tight binding to a widely distributed cellular molecule following localized administration, thus preventing diffusion or transport of the thiamin-depleting molecule to other locations.

The targeting can, for example, be provided by an antibody, antibody fragment, or a derivative of an antibody which recognizes an appropriate cellular antigen on the target cells. The targeting can also be provided by a cellular receptor ligand. A "cellular receptor ligand" refers to a molecule or a portion of a molecule which is recognized and bound by a cellular receptor, preferably a receptor accessible on the cell surface. Such receptors are generally proteins which are able to specifically or at least preferentially bind particular molecules or ligands. Commonly, the binding of a natural ligand is linked with a further biological response or effect. Additional targeting molecules can be obtained using phage-display or combinatorial libraries to identify peptides or peptidomimetics or other molecules which specifically or preferentially bind to particular tissues or cells. An example is the identification of peptides which preferentially bind to epithelial markers, such as tumor endothelial cell markers or tissue specific capillary cell markers.

Such targeting molecules can be used in a variety of different ways, including, for example, direct attachment or association of the targeting molecule with the thiamin-depleting compound, and attachment or association of the targeting molecule with a complex which includes a thiamin-depleting compound. Examples of such complexes include complexes using protective components such as liposomes, nanospheres or nanoparticles which are preferably biodegradable, or biocompatible gels. Such complexes can be used for delivery of many different types of compounds. In an example particularly useful for delivery of nucleic acid sequences, nucleic acid binding compounds, e.g., polylysine, spermine, or other DNA condensing compounds, can be attached to a targeting molecule and allowed to bind to the nucleic acid.

The targeting can also be provided by localized administration, meaning that the thiamin-depleting agent is introduced into the organism in a specific location which results in exposure of the targeted cells to the thiamin-depleting agent. Preferably, the location of introduction is among or around the targeted cells. An example of such localized administration is direct injection, for example, injection into and/or around a tumor. Localized administration can be utilized either alone or in conjunction with other targeting technique or techniques to enhance the localization effects. As another example, direct localized administration can be provided by inhalation or instillation of the thiamin-depleting compound agent into the lungs.

The targeting can also be provided by intravenous injection of compositions having particular selections of cationic lipids upstream of a capillary bed. An example of such a cationic lipid is the cationic lipid known as DOTMA. In using such cationic lipids, it is often beneficial to utilize a neutral co-lipid, for example, cholesterol or DOPE.

"Cationic lipid" refers to a compound having a lipid structure as understood by those skilled in the art, which has a net positive charge in aqueous solution at physiological pH. A "neutral lipid" or "neutral co-lipid" is a lipid compound which is uncharged or very nearly uncharged in aqueous solution at physiological pH.

In another example, the targeting by localized administration can also be accomplished by intra-arterial infusion into an artery supplying a localized tumor. Generally this will utilize a surgically implanted catheter and an infusion pump.

Yet another example of targeting is the use of a thiamin-depleting agent where the agent is inactive until activated in a localized manner or the agent activates an agent which thus becomes toxic to cells. An example of such activation is a localized prodrug activation, in which an inactive prodrug is locally converted to an active drug form. Such prodrugs can be of various types, and the localized activation can, correspondingly, be accomplished in various ways. For example, as described in the Detailed Description, such prodrug activation can be accomplished using prostate specific antigen (PSA) in an example of localized activation of a thiamin-depleting agent, e.g., a thiaminase. Another example uses antibody directed enzyme prodrug therapy, in which an enzyme is attached to a targeting antibody (i.e., a targeted enzyme). The attached enzyme then activates an administered prodrug locally at the targeted cells. The prodrug is only toxic in its activated form, and thus kills cells in situ. The prodrug can be a thiamin antimetabolite, e.g., a thiamin analogue. For example, a tissue-targeted thiaminase can cleave a thiamin analogue prodrug to produce a toxic compound that kills cells. Other types of targeting molecules could also be used in this manner.

Yet another exemplary targeting method utilizes the hypoxic or anaerobic interior of solid tumors as a targeted environment. One approach uses a gene expression control element which is inducible under hypoxic conditions to control the expression of a nucleotide sequence encoding a thiamin-depleting agent, e.g., a thiaminase or derivative. Some elements of this type have been termed "hypoxic responsive elements" or "HRE", for example elements which are binding sites for the transcriptional complex, hypoxia inducible factor-1 (HIF-1). A coding sequence controlled by a hypoxia-inducible element will be expressed at a significantly higher level, e.g., preferably at least 2-fold and more preferably at least 5-fold higher in a hypoxic tissue environment than in normally oxygenated tissue. The nucleic acid encoding the thiamin-depleting agent can be delivered in a variety of different ways, but typically will be on a vector, such as a viral, e.g., retroviral, or plasmid vector. The vector can be located to the hypoxic interior of solid tumors using a number of different methods as known to those skilled in the art. Examples include direct injection into a tumor, localization using antibodies, antibody fragments, targeting proteins, peptides, or ligands which preferentially bind to proteins primarily present on tumor cells, intravenous injection upstream of a tumor, or any method which will allow the vector to penetrate into the tumor. A second approach uses anaerobic bacteria, such as Clostridium spp., to target a thiamin-depleting agent to the interior of solid tumors. The bacteria can, for example, be modified to secrete a thiamin-depleting agent, such as a thiaminase, or can express a prodrug activating enzyme, e.g., prodrug cleaving, which will activate an inactive prodrug of a thiamin-depleting compound.

The terms "hypoxic" and "anaerobic" refers to a lower oxygen tension or concentration which is lower than in most similar environments. Thus, a tissue, e.g., the interior of a tumor, is hypoxic if the concentration of dissolved oxygen is significantly lower than in most normal tissues of the same organism or similar organisms. Generally a hypoxic tissue region will have an oxygen partial pressure of less than about 20 mmHg, preferably less than about 10 mmHg, and most preferably less than about 5 or 3 mmHg. In contrast, normal tissue will generally have an oxygen partial pressure of greater than 20 mmHg, typically in the range of about 24-66 mmHg.

Non-pathogenic bacteria can also be used to deliver a thiamin-depleting compound such as a thiaminase by colonizing a particular part of the body (i.e., localized colonization) with an appropriate bacterium expressing the compound. For example, particular bacteria are known which colonize different parts of the intestines, the vagina and the bladder. Other parts of the body can be protected, as needed, through measured administration of thiamin.

In connection with the various targeting techniques, those skilled in the art will recognize that such targeting can be utilized for both the administration of thiamin-depleting agents and for the administration of nucleic acid sequences encoding thiamin-depleting agents.

In a preferred embodiment, the invention provides a method of inducing apoptosis of a selected group of vertebrate cells in vivo by reducing the level of thiamin in the cells sufficiently to induce apoptosis by administering a plurality of thiamin-depleting agents to the organism. The plurality of thiamin-depleting agents may belong to a single class, such as thiaminases, or may be a combination of agents drawn from different classes or combinations of these possibilities. Thus, in preferred embodiments at least one of the thiamin-depleting agents is a thiamin-cleaving compound, such as a thiaminase or thiaminase derivative, a thiamin binding compound, or a thiamin antagonist or antimetabolite. In certain embodiments at least one of the agents is a thiamin-cleaving compound, e.g., a thiaminase, and at least one is a thiamin-binding compound; the thiamin-cleaving compound can be provided or act extracellularly and the thiamin-binding compound can be provided or act intracellularly. Similarly, in certain embodiments at least one of the agents is a thiamin-cleaving compound, e.g., a thiaminase, and at least one is a thiamin antagonist; the thiamin-cleaving compound may be provided or act extracellularly and the thiamin antagonist can be provided or act intracellularly. In a similar manner as discussed above, peptide or polypeptide agents can be encoded on a vector and are expressed from a recombinant gene in the organism. Likewise, in preferred embodiments, the plurality of thiamin-depleting agents includes a plurality of thiamin-cleaving agents, such as a plurality of thiaminases, a plurality of thiamin-binding compounds, or a plurality of thiamin anti-metabolites. In preferred embodiments, a plurality of thiamin-depleting agents can be administered sequentially or can be administered concurrently. Likewise, a plurality of agents can be administered in two or more sets, in which the members of a set are administered concurrently and the individual sets are administered sequentially. Each set contains one or more thiamin-depleting agents.

Embodiments of the method using a plurality of thiamin-depleting agents include a variety of specific choices, such as those described herein in other embodiments of this aspect for particular thiamin-depleting agents, methods and agents for localizing, targeting compounds, compounds which enhance bioavailability of an agent, compounds which enhance recombinant gene delivery and/or expression, and other selections.

In cases in which the organism reacts immunologically to a thiamin-depleting agent, sequential administration of a plurality of thiamin-depleting agents can be used to avoid excessive immune response which could interfere with the thiamin depletion. In this case, a shift is made to an immunologically unrelated agent before the development of a strong immune response to the prior agent. Thus, the shift is timed to reduce the immune response to any of the plurality of agents.

In preferred embodiments, the method uses at least one peptide or polypeptide thiamin-depleting agent. As indicated above, this can lead to an immune response to that agent. Therefore, in preferred embodiments, the method also includes administering an inactive analogue of the polypeptide, e.g., a thiaminase or thiaminase derivative, thereby inducing immunologic tolerance to the inactive and corresponding active peptides polypeptides. Preferably, the inactive analogue is not targeted to the selected group of cells.

An "inactive analogue" refers to a compound which does not have appreciable activity of a particular type, which is structurally similar to a corresponding compound which possesses a significant level of the particular activity. For use for inducing tolerance, an inactive analogue preferably has the same major epitopes as a corresponding active compound, and preferably has only minimal changes necessary to cause a loss of the activity.

As used herein, the term "tolerance" refers to immunologic tolerance, and thus indicates a reduced responsiveness of an organism's immune system to a particular antigen. Generally immunologic tolerance involves the antigen-specific inactivation or deletion of particular B- or T-lymphocytes. As understood by those skilled in the art, such tolerance can develop in several different ways with variations in the underlying biological processes. For example, it is understood that the mode of antigen exposure is frequently an important factor in the development of tolerance.

In other preferred embodiments, the method of inducing apoptosis provides a method for treating a neoplastic disorder in a vertebrate organism. In this method the selected group of cells are cells of the neoplastic disorder. In preferred embodiments, the neoplastic disorder is a cancer and the vertebrate organism is a human. Also in preferred embodiments, cells of the cancer form a solid tumor. Other preferred embodiments of the method for treating a neoplastic disorder are as described above or otherwise described herein, including embodiments in which a plurality of thiamin-depleting agents is used.

The term "neoplastic disorder" refers to a condition in a complex organism, such a vertebrate, in which there is an abnormal mass of tissue, including dispersed cells, the growth of which exceeds and is uncoordinated with that of the normal tissues. Thus, the term includes neoplastic growths or tumors. Neoplastic disorders particularly include "cancer" or malignant tumors. A large number of different cancers are known to those skilled in the art, the cells of which can be induced to undergo apoptosis.

A "solid tumor" refers to a localized mass of cancer cells which form a macroscopic group of cells and which is physically distinct from the surrounding tissue. The term includes both encapsulated and nonencapsulated tumors. Thus, the boundary between the tumor mass and normal tissue is not necessarily a discrete boundary.

The method of treating a neoplastic disorder by reducing the level of thiamin in the cells of the neoplastic disorder can also be used in conjunction with other anti-neoplastic treatments. Thus, in preferred embodiments, the invention provides a method of treating a neoplastic disorder which involves reducing the level of thiamin in cells of a neoplastic disorder in order to induce apoptosis and also administering a second anti-neoplastic treatment to the organism. The second anti-neoplastic treatment can be of a variety of types, such as those commonly currently utilized, e.g., radiation and treatment with cytotoxic agents, which preferentially kill growing cells. Also in a preferred embodiment, the second anti-neoplastic treatment induces apoptosis of growing cells.

In preferred embodiments the order and timing of the thiamin depletion and the second antineoplastic treatment include a number of different regimes, for example concurrent administration of the two treatments, thiamin depletion first followed by the second antineoplastic treatment, and administration of the second antineoplastic treatment first followed by the thiamin-depleting treatment. Other preferred embodiments are as described above for localized thiamin depletion.

Similarly, in a related aspect the invention provides a method of killing a selected group of vertebrate cells in vivo by reducing the level of thiamin in the targeted cells in localized thiamin deficiency induced apoptosis (LAIDT) and, in conjunction, administering to the animal containing those cells an accessory treatment which enhances the effectiveness of the thiamin reduction. A variety of different accessory methods can be used to enhance the effectiveness of the thiamin deficiency induced apoptosis. In methods involving the use of an accessory treatment, the thiamin deficiency induced apoptosis is targeted to the selected cells, for example, by targeting methods as described herein. In addition, the accessory treatment may also be targeted unless otherwise indicated. Again, a variety of different targeting methods may be used as appropriate for the type of composition to be delivered. Such methods include, for example, the targeting methods described herein in connection with creation of a localized thiamin deficiency. However, persons familiar with the delivery of the therapeutic compositions will recognize that a variety of other methods may also be used and will readily understand the selection of appropriate methods.

In a preferred embodiment, the accessory treatment involves the elevation of a carbohydrate, preferably glucose, in the selected cells. While the carbohydrate level elevation may be localized or targeted to the selected cells, generally such localization is not necessary. Such a carbohydrate level elevation can be accomplished readily, for example, using an intravenous solution containing a particular carbohydrate, e.g., glucose. Alternatively, a dietary supplement containing the desired carbohydrate can be provided.

In other preferred embodiments, the accessory treatment involves inhibiting the formation or the function of tumor vasculature or inhibiting the ability of tumors to invade surrounding tissue. Thus, such accessory methods can be, for example, antiangiogenesis methods, methods which induce inflammation in tumor neovasculature, or methods which inhibit the modification of intracellular matrix material in tumor formation. A large number of angiogenesis inhibitors are known, including those specifically mentioned in the detailed description below and active analogs and derivatives of those compounds. As indicated, examples of such inhibitors include small molecules, antibodies, other polypeptides, and nucleic acid molecules. In particular, such nucleic acid molecules include ribozymes and other catalytic nucleic acid molecules such as those obtained by in vitro combinatorial selection techniques as well as other selection and evolution methods. In general, such nucleic acid inhibitors and antibody inhibitors are targeted to a gene product which is needed for tumor angiogenesis.

In this context, the phrase "needed for tumor angiogenesis" means that elimination of the activity, including elimination of expression, of the gene product at least slows the process of tumor angiogenesis and preferably stops tumor angiogenesis. Preferably, activity of the gene product does not need to be completely eliminated but merely reduced in order to inhibit tumor angiogenesis.

With respect to the present invention, the term "catalytic nucleic acid molecule" refers to a molecule which contains a plurality of nucleotides and/or nucleotide analogs and which can act to catalyze a reaction on another molecule, usually another nucleic acid molecule. Preferably a majority of the catalytic nucleic acid molecule is composed of nucleotides or nucleotide analogs. In most cases the molecule catalyzes a cleavage reaction. The term includes "ribozymes". This term refers to catalytic nucleic acid molecules which are based on the structure of naturally-occurring self-cleaving RNA sequences, and which retain the general structural motif of the natural sequence. As indicated below, ribozymes and other catalytic nucleic acid molecules can contain a variety of substitutions of ribonucleotides with deoxyribonucleotides, nucleotide analogs, and non-nucleotidic linkers or terminal moieties so long as catalytic activity is retained.

Also as indicated in preferred embodiments, the accessory treatment involves inhibiting the expansion of a tumor in a surrounding tissue. In a particular embodiment the accessory method involves inhibiting the action of matrix modifying enzymes, for example, matrix metalloproteinases (MMPs).

In yet another preferred embodiment, as indicated, the method involves inhibiting the function of tumor neovasculature. This can be accomplished, for example, by inducing inflammation in the tumor vasculature, thereby inhibiting the transport of nutrients to and waste products from the tumor cells. It is expected that this results in one or more of: slowing tumor growth, inducing quiescence of actively growing tumor cells, and killing tumor cells. Any such effects will result in enhancing the effectiveness of localized thiamin deficiency induced apoptosis.

The terms "tumor vasculature" or "tumor neovasculature" refer to the blood vessels which develop to provide a blood supply to a tumor, as distinguished from vasculature which primarily functions to supply normal tissue.

In other embodiments, a method involves modulating the level of activity of an apoptosis related protein. As described below, such apoptosis related proteins include both apoptosis suppressing proteins and apoptosis enhancing proteins. Thus, such modulation can be accomplished, for example, by increasing the level of activity of one or more apoptosis enhancing proteins and/or by decreasing the level of activity of one or more apoptosis suppressing proteins. The up regulation can be accomplished, for example, by administration of a compound which either increases the production of such an apoptosis enhancing protein or which increases the sensitivity of cells to the presence of such a protein. Included in the methods for increasing the production of an apoptosis enhancing protein are gene therapy methods providing expression of a recombinant coding sequence encoding the protein or a biologically active fragment or derivative of the protein. On the other hand, inhibition of apoptosis suppressing proteins can utilize a variety of different types of inhibitors, including, for example, small molecules, antibodies, and nucleic acid inhibitors, including ribozymes and other catalytic nucleic acid molecules and antisense and triple helix inhibitors. Preferably, the apoptosis related protein is a secreted protein such as those which have been identified in the literature as secreted apoptosis related proteins (SARPs).

The term "apoptosis related protein" refers to a polypeptide which is involved in the process of apoptosis or a polypeptide whose presence or absence affects the sensitivity of cells to signals leading to apoptosis. In preferred embodiments, the apoptosis related protein is a receptor, a receptor component, or a receptor ligand.

In yet another preferred embodiment, the accessory treatment involves the administration of a prodrug. Preferably, activation of the prodrug is targeted to the selected group of cells. Generally, such prodrugs are activated by chemical modification or cleavage of the prodrug molecule yielding an active molecule. As understood, a variety of different activator enzyme prodrug combinations can be utilized. In particular, a thiamin cleaving compound, for example, a thiaminase or thiaminase derivative, can be used to cleave a prodrug where the cleavage results in the production of a molecule toxic to surrounding cells. In most cases, such a molecule would have structural similarities to thiamin.

In another preferred embodiment, the accessory treatment involves the administration of a second apoptosis inducing treatment. Preferably, but not necessarily, the apoptosis induction pathway for the second method involves at least a portion of the pathway involved in thiamin deficiency induced apoptosis. Such a second apoptosis inducing method can, for example, involve the administration of a compound which induces apoptosis.

In yet other embodiments, as indicated above, the accessory method can involve the creation of a generalized thiamin deficiency. Alternatively, particularly in connection with actively growing cancer cells, the generalized thiamin deficiency can be utilized alone to induce apoptosis of the rapidly growing cells of a tumor which should be more sensitive to the thiamin deficiency. It is expected that such actively growing cells would deplete the intracellular thiamin more rapidly than normal cells, and would therefore enter apoptosis sooner. After apoptosis of at least some of the actively growing cells, had occurred, thiamin can then be administered to prevent death of normal cells. Such generalized thiamin deficiency can also be used in conjunction with other treatment methods, for example, other methods as described herein for use as accessory methods in conjunction with localized thiamin deficiency.

Also, as indicated above, the accessory treatment includes the administration of a second antineoplastic treatment, for example, the administration of an antineoplastic agent. Such antineoplastic agents include, for example, conventional antineoplastic, e.g., anticancer agents that also include other methods for the inhibition and/or killing of neoplastic cells.

In another aspect, the invention features the use of a thiamin-depleting agent in the preparation of a medicament effective for the treatment of a disease or disorder in a vertebrate, such as a mammal, in which the elimination of a group of cells provides a therapeutic benefit. Such diseases or conditions include, for example, neoplastic disorders, particularly including cancers. In preferred embodiments, the medicament contains other components as described herein for pharmaceutical compositions and for compositions in the methods of inducing apoptosis, treating cancer, killing a selected group of cells, and compositions in other aspects described herein.

A "therapeutic benefit" refers to a reduction in the number of cells of the condition being treated, or an improvement in at least one symptom, or an improvement in the condition. An improvement in condition can include a cure.

As indicated above, certain thiamin-depleting agents can be delivered by the delivery of a nucleic acid sequence encoding the agent, such as a thiaminase or a thiaminase derivative, and expressing the agent from that nucleic acid sequence. Therefore, in another aspect, the invention provides a method for delivering a nucleic acid sequence encoding a thiaminase or derivative thereof to vertebrate cells in vivo by delivering a vector which includes a nucleic acid sequence encoding the thiaminase or thiaminase derivative to the cells.

As recognized by those skilled in the art, it is often advantageous for delivery of nucleic acid coding sequences to vertebrate cells in vivo to prepare the nucleic acid in a composition, complex, or formulation which can be selected to have a variety of different components, depending on the particular application. For example, the nucleic acid or vector bearing the coding sequence can be prepared associated with a cationic lipid. Examples of such cationic lipids include, for example, DOTMA, DOTAP, DDAB, DOSBA, CTAB, DC-chol, and DMRIE. In these formulations it can also be advantageous to incorporate an additional lipid, generally an essentially neutral co-lipid, such as DOPE or cholesterol. These compounds are known to those skilled in the art, and are identified, for example, in Felgner et al., *Cationic Lipids for Intracellular Delivery of Biologically Active Molecules*, U.S. Pat. No. 5,264,618, issued Nov. 23, 1993, and in Gao and Huang, 1995, *Gene Therapy* 2:710-722. The structures of a variety of useful lipids are shown in the Gao and Huang reference. DOPE is the abbreviation for dioleoylphosphatidylethanolamine. DOSPA is 2,3-dioleoyloxy-N-(2(sperminecarboxyamido)-ethyl)-N,N-dimethyl-1-propanaminium trifloroacetate. DC-chol is 3-β(N-(N',N'-dimethylaminoethane) carbamoyl) cholesterol. DOTMA is N-(2,3-dioleoyloxy) propyl)-N,N,N-trimethylammonium chloride. DOTAP is 1,2-dioleoyloxy-3-(trimethyl ammonia) propane. The above references are hereby incorporated by reference in their entireties, and show both appropriate lipid compounds and methods of using those lipids for delivery of biologically active molecules including polypeptides and nucleic acid sequences.

A further example of the use of lipid DNA complexes is provided by Brigham, *Method of In Vivo Delivery of Functioning Foreign Genes*, International Application PCT/US90/05993 which is hereby incorporated by reference. The Brigham reference describes the use of DNA liposome preparations which produced transient expression in lung tissue of the sequence driven by a metalathianine promoter following intravenous injection. The results indicated that such lipid DNA formulations could be used to transfect cells surrounding the first capillary bed downstream from the point of injection.

In preferred embodiments, the DNA can also be associated with a DNA-binding compound, a cell-permeabilizing lytic agent, and a targeting compound, either individually or in combination. Examples of such components and the use of such complexes is described, for example, in Smith et al., *Nucleic Acid Transporters for Delivery of Nucleic Acids into a Cell*, International Application PCT/US96/05679, International Publication No. WO 96/40958 and in Curiel et al., *Composition for Introducing Nucleic Acid Complexes and to Higher Eucaryotic Cells*, U.S. Pat. No. 5,547,932, issued Aug. 20, 1996. These references are hereby incorporated by reference.

"DNA binding compounds" refer to compounds as understood by those skilled in the art which are able to form strong associations with DNA under approximately physiologic conditions. The interaction between the binding compound and the DNA can involve one or more of a variety of different physical interactions, including but not limited to charge-charge interactions, H-bonding interactions, van der Waals interactions, and hydrophobic interactions. Examples include polylysine and spermine among others. Preferably the binding compound binds significantly more tightly to dsDNA than to RNA. "DNA condensing compounds" are binding compounds which are able to collapse dsDNA so that the DNA molecule occupies a significantly smaller solution volume.

"Cell permeabilizing lytic agents" are compounds, e.g., certain peptide sequences, which enhance at least the local permeability of a cell to passage of other molecules across the cell membrane. Thus, a compound which is associated with or which is also present at a cell membrane with the agent is more likely to enter the cell than in the absence of the lytic agent. As described below, it is known that certain types of peptide sequences act as lytic agents and enhance the entry of associated compounds into a cell. Such associated compounds can be of various types, including, for example, DNA polynucleotides.

In addition to targeting compounds or ligands, targeting can also be provided in the case of nucleic acid sequence delivery by localized expression. Among other methods, such localized expression can be provided by using gene switch methods as described in the literature, including gene switches using an inducible promoter, such as one induced by a steroid. Thus, localized administration of the appropriate switching agent will result in induction of expression only, or at least primarily in the close vicinity of the administered inducing agent. A variety of such inducible promoters are known in the art and can be utilized for such gene switches.

Also in preferred embodiments, the DNA is associated with a compound which enhances the bioavailability of the DNA. The phrase "enhances the bioavailability" means that the compound increases the total availability of an associated molecule for participation in a particular response or action. Thus, for example, the enhancing compound can increase the time before degradation or the time at a location of an associated molecule. A number of such compounds have been described, for example, in Rolland et al., *Formulated Nucleic Acid Compositions and Methods of Administering the Same for Gene Therapy*, International Application PCT/US96/17038, International Publication WO 96/21470. Such compounds include, for example, polyvinyl pyrrolidone, polyvinyl alcohol, polyethylene glycol, propylene glycol, and chitosan. As indicated, such compounds can be utilized in the delivery of nucleic acid molecules, but can also be used in the delivery of other agents, such as the thiamin-depleting agents described herein.

As indicated above, targeting can-be provided by components such as antibodies and receptor ligands. The encoded thiamin-depleting agent can be any of a variety of polypeptide compounds, such as polypeptide thiamin-cleaving compounds, including thiaminases and thiaminase derivatives, and polypeptide thiamin-binding compounds or derivatives.

With the exception of the thiaminase of *Bacillus thiaminolyticus*, the majority of the naturally occurring thiaminases are encoded by nucleic acid sequences which have not previously been isolated. Therefore, the invention also provides a purified, enriched, or isolated nucleic acid sequence encoding a thiaminase or a derivative of a thiaminase which is from such another source or which differs from a full-length naturally occurring thiaminase from *Bacillus thiaminolyticus*. However, it should be clear that nucleic acid sequences encoding full-length *Bacillus thiaminolyticus* thiaminase can also be utilized for the present invention, directly or obtaining derivatives or other related thiamin-cleaving compounds.

In a preferred embodiment, the thiaminase is from a *Naegleria* species, such as *Naegleria gruberi*. In another preferred embodiment, the thiaminase is from a fern or other pteridophyte, such as the fern bracken (*Pteridium aquilinum*) or the fern nardoo (*Marsilea drummondii*). In still another, the thiaminase is from a fish, preferably of the family Cyprinidae, such as carp.

In the case of nucleic acid sequences encoding thiaminase derivatives, it is often advantageous for the encoded amino acid sequence to be shorter than a full length naturally occurring thiaminase. Therefore, in preferred embodiments, the nucleic acid sequence encodes a modified thiaminase or thiaminase derivative containing about 90% or less, 80% or less, 70% or less, 60% or less, 50% or less, or 40% or less or the amino acid sequence of the corresponding natural thiaminase. Thus, for example, the nucleic acid sequence can encode a derivative having about 400 or fewer, 200 or fewer, 100 or fewer, or 50 or fewer amino acids. Similarly, the nucleic acid sequence can encode a polypeptide thiamin-binding compound or derivative.

By "isolated" in reference to nucleic acid is meant a polymer of nucleotides conjugated to each other, including DNA or RNA that is isolated from a natural source or that is synthesized. The isolated or synthesized (e.g., cDNA) nucleic acids of the present invention are unique in the sense that they are not found in a pure or separated state in nature. Use of the term "isolated" indicates that a naturally occurring sequence has been removed from its normal cellular (i.e., chromosomal) environment. Thus, the sequence may be in a cell-free solution or placed in a different cellular environment. The term does not imply that the sequence is the only nucleotide sequence present, but that it is essentially free (about 90-95% pure at least) of non-nucleotide material naturally associated with it and thus is meant to be distinguished from isolated chromosomes.

By the use of the term "enriched" in reference to nucleic acid is meant that the specific DNA or RNA sequence constitutes a significantly higher fraction (2-5 fold greater, more preferably >100-fold) of the total DNA or RNA present in the cells or solution of interest than in normal or diseased cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased. The term "significant" here is used to indicate that the level of increase is useful to the person making such an increase, and generally means an increase relative to other nucleic acids of about at least 2 fold, more preferably at least 5- to 10-fold, more preferably at least 100- to 1000-fold, or even more. The term also does not imply that there is no DNA or RNA from other sources. The other source DNA may, for example, comprise DNA from a yeast or bacterial genome, or a cloning vector. This term distinguishes the sequence from naturally occurring enrichment events, such as viral infection, or tumor type growths, in which the level of one mRNA may be naturally increased relative to other species of mRNA. That is, the term is meant to cover only those situations in which a person has intervened to elevate the proportion of the desired nucleic acid.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level this level should be at least 2-5 fold greater, e.g., in terms of mg/ml, more preferably at least 100- or 1000-fold greater). Individual clones isolated from a cDNA library may be purified to electrophoretic homogeneity. The claimed DNA molecules obtained from these clones can be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^6$-fold purification of the native message. Thus, purification of at least three orders of magnitude, and more preferably four or five orders of magnitude is expressly contemplated. The term is also chosen to distinguish clones already in existence which may encode a thiaminase or portion of a thiaminase but which have not been isolated from other clones in a library of clones. Thus, the term covers clones encoding a thiaminase or portion of a thiaminase which are isolated from other non-thiaminase clones.

A polypeptide thiamin-depleting agent can be encoded by a full-length nucleic acid sequence or portion of the full-length nucleic acid sequence. In preferred embodiments the isolated nucleic acid comprises, consists essentially of, or consists of a nucleic acid sequence encoding a naturally-occurring thiaminase, a nucleic acid sequence that hybridizes to such a nucleic acid sequence, or a functional derivative of either. The nucleic acid may be isolated from a natural source by cDNA cloning, use of PCR primers, subtractive hybridization, or other means standard to the art; the natural source may be any organism which naturally produces a thiaminase, specifically including those described in the Detailed Description below, and the nucleic acid may be synthesized by the triester or other method or by using an automated DNA synthesizer.

The term "hybridize" refers to a method of interacting a nucleic acid sequence with a DNA or RNA molecule in solution or on a solid support, such as cellulose or nitrocellulose. If a nucleic acid sequence binds to the DNA or RNA molecule with high affinity, it is said to "hybridize" to the DNA or RNA molecule. The strength of the interaction between the probing sequence and its target can be assessed by varying the stringency of the hybridization conditions. Various low or high stringency hybridization conditions may be used depending upon the specificity and selectivity desired. Stringency is controlled by varying salt or denaturant concentrations. Examples of hybridization conditions are shown in the examples below. Those skilled in the art will recognize how such conditions can be varied to vary specificity and selectivity. Under highly stringent hybridization conditions only highly complementary nucleic acid sequences hybridize. Preferably, such conditions prevent hybridization of nucleic acids having one or two mismatches out of 20 contiguous nucleotides.

The invention also features recombinant nucleic acid encoding a thiamin-depleting agent, preferably in a vector effective to initiate transcription in a host cell. The vector may be in such a eukaryotic host cell or in vivo in cells of an organism. The recombinant nucleic acid can, for example, contain a transcriptional initiation region functional in a cell, a sequence complementary to an RNA sequence encoding a thiamin-depleting agent polypeptide and a transcriptional termination region functional in a cell. While recombinant nucleic acid encoding an unmodified thiaminase, for example in a eukaryotic expression vector, from *Bacillus thiaminolyticus* can be utilized in the methods of this invention, in certain embodiments the encoded thiamin-depleting agent is different from that enzyme, and in other embodiments is not a modification or derivative of that thiaminase.

Thus, in a related aspect the invention provides a eukaryotic expression vector which includes a nucleic acid sequence encoding a thiamin-depleting agent. The expression vector is constructed and adapted for expression in eukaryotic cells, preferably in human cells. Preferably the vector does not include an origin of replication functional in eukaryotic cells. While vectors based on viral sequences can be beneficially used, in preferred embodiments, the vector is a non-viral vector, meaning that the vector does not contain sufficient viral sequences to cause viral replication or capsid formation. In certain embodiments, the encoded thiamin-depleting agent differs from a full-length thiaminase from *Bacillus thiaminolyticus* and in other embodiments is not a modification or derivative or that thiaminase. Other preferred embodiments are as described above for the nucleic acids and nucleic acid delivery methods.

In another related aspect, the invention provides a vector which includes a recombinant nucleic acid sequence which encodes a polypeptide thiamin-depleting agent, such as a thiaminase or a thiaminase derivative or thiamin-binding compound or derivative which is different from a *Bacillus thiaminolyticus* thiaminase. In preferred embodiments, the vector is an expression vector which is constructed and adapted for expression in prokaryotic cells, for example, *E. coli*, though a variety of other bacteria can be used. In other embodiments the vector is a eukaryotic expression vector, which is constructed and adapted for expression in eukaryotic cells. Other preferred embodiments are as described for the vectors, nucleic acids and nucleic acid delivery methods above.

In accord with the vectors and methods for delivery of nucleic acid encoding a thiamin-depleting agent, the invention also provides a eukaryotic cell transfected with a eukaryotic expression vector containing a nucleic acid sequence encoding a thiamin-depleting agent. Preferably, the cell is a vertebrate cell in vivo in a vertebrate organism, such as a bird or a mammal, e.g., a human. The thiamin-depleting agent can be any peptide or polypeptide compound, such as those described in the above aspects.

In another related aspect, the invention provides a composition for delivery of a nucleic acid sequence encoding a thiaminase or a thiaminase derivative to vertebrate cells in vivo. The composition includes a nucleic acid sequence encoding the thiaminase or a thiaminase derivative. The composition preferably also includes a component associated with a nucleic acid sequence which enhances delivery of the nucleic acid into the cells. In preferred embodiments, the nucleic acid and other components of the composition are as described above in connection with methods involving delivery of a nucleic acid sequence.

Thiamin-depleting agents, such as thiaminases and thiamin-binding compounds obtained from natural sources will be useful as described for the methods of this invention, and for analysis for constructing derivatives and synthetic thiamin-cleaving and thiamin-binding compounds. Thus, another aspect of the invention features an isolated, enriched, or purified polypeptide thiamin-depleting agent which has not previously been obtained. In the case of an agent which has been enriched or partially purified, the invention provides a purified agent, so that the agent is separated from at least 95%, preferably from at least 98%, and still more preferably from at least 99% of the macromolecules from the environment in which the agent is naturally produced. The agent therefore differs from a *Bacillus thiaminolyticus* thiaminase or mutated form of that thiaminase involving substitution or deletion of less than 1%, 5%, or 10% of the amino acid sequence of that thiaminase. In preferred embodiments, the agent is a thiaminase or thiaminase derivative or other polypeptide thiamin-cleaving compound. Also in preferred embodiments the agent is a thiamin-binding compound or derivative.

By "polypeptide thiamin-depleting agent" it is meant an amino acid sequence which has antithiamin activity under conditions approximating human intracellular or extracellular conditions. In some cases the sequence is substantially similar to at least a portion of the amino acid sequence of a naturally occurring thiaminase or thiamin-binding compound. A sequence that is substantially similar will preferably have at least 90% identity (more preferably at least 95% and most preferably 99-100%) to the sequence or portion of the sequence of the naturally occurring thiaminase or thiamin-binding compound. In other embodiments, the amino acid sequence has at least one change, such as a chemical modification of an amino acid or incorporation of at least one non-natural amino acid.

By "identity" is meant a property of sequences that measures their similarity or relationship. Identity is measured by dividing the number of identical residues in the two sequences by the total number of residues and multiplying the product by 100. Thus, two copies of exactly the same sequence have 100% identity, but sequences that are less highly conserved and have deletions, additions, or replacements have a lower degree of identity. Those skilled in the art will recognize that several computer programs are available for determining sequence identity.

By "isolated" in reference to a polypeptide is meant a polymer of 6, 12, 18 or more amino acids conjugated to each other, including polypeptides that are isolated from a natural source or that-are synthesized. In this invention, the polypeptide will commonly have at least about 50, 100, 200, or 400 amino acids conjugated together. The isolated polypeptides of the present invention are unique in the sense that they are not found in a pure or separated state in nature. Use of the term "isolated" indicates that a naturally occurring sequence has been removed from its normal cellular environment. Thus, the sequence may be in a cell-free solution or placed in a different cellular environment. The term does not imply that the sequence is the only amino acid chain present, but that it is essentially free (about 90-95% pure at least) of material naturally associated with it.

By the use of the term "enriched" in reference to a polypeptide it is meant that the specific amino acid sequence constitutes a significantly higher fraction (2-to 5-fold greater) of the total of polypeptide present in the cells or solution of interest than in normal or diseased cells or in the cells from which the sequence was taken. This could be caused by a person by preferential reduction in the amount of other polypeptides present, or by a preferential increase in the amount of the specific amino acid sequence of interest, or by a combination of the two. However, it should be noted that "enriched" does not imply that there are no other amino acid sequences present, just that the relative amount of the sequence of interest has been significantly increased. The term significant here is used to indicate that the level of increase is useful to the person making such an increase, and generally means an increase relative to other polypeptides of about at least 2-fold, more preferably at least 5 to 10 fold or even more. The term also does not imply that there is no polypeptide from other sources. The other source polypeptide may, for example, comprise amino acid encoded by a yeast or bacterial genome, or a cloning vector. The term is meant to cover only those situations in which a person has intervened to elevate the proportion of the desired polypeptide.

It is also advantageous for some purposes that an amino acid sequence be in purified form. The term "purified" in reference to a polypeptide does not require absolute purity (such as a homogeneous preparation); instead, it represents an indication that the sequence is relatively purer than in the natural environment (compared to the natural level this level should be at least 2-5 fold greater, e.g., in terms of mg/ml). Purification of at least one order of magnitude, preferably two or three orders, and more preferably four or five orders of magnitude is expressly contemplated. The substance is preferably free of contamination at a functionally significant level, for example 90%, 95%, or 99% pure.

In another aspect the invention features an isolated, enriched, or purified polypeptide thiamin-depleting agent fragment, specifically including a thiaminase fragment. Preferably the polypeptide is a "recombinant polypeptide".

By "a polypeptide thiamin-depleting agent fragment" is meant an amino acid sequence that is less than a full-length sequence of a naturally occurring thiamin-depleting agent or equivalent length modification of such an agent, such as a shortened form of a thiaminase. Examples of such fragments include catalytically active fragments or mutant polypeptides, such as catalytically active thiaminase regions or mutants.

By a "polypeptide thiamin-depleting agent mutant" is meant a polypeptide which differs from the native sequence of the corresponding polypeptide thiamin-depleting agent in that one or more amino acids have been changed, added or deleted. Changes in amino acids may be conservative or non-conservative. By "conservative" it is meant the substitution of an amino acid for one with similar properties such as charge, hydrophobicity, structure, etc. Examples of polypeptides encompassed by this term include, but are not limited to, (1) chimeric proteins which comprise a portion of a thiamin-depleting agent polypeptide sequence fused to a non-thiamin-depleting agent polypeptide sequence, for example an antibody or antibody fragment polypeptide sequence, and (2) thiamin-depleting agent proteins having a point mutation or a deletion. A thiamin-depleting agent mutant will retain some useful function such as, for example, binding to thiamin, or thiamin-cleaving catalytic activity. Thiamin-depleting agent mutants specifically include thiaminase mutants.

The term "recombinant polypeptide thiamin-depleting agent" is meant to include a polypeptide produced by recombinant DNA techniques such that it is distinct from a naturally occurring polypeptide either in its location (e.g. present in a different cell or tissue than found in nature), purity or structure. Generally, such a recombinant polypeptide will be present in a cell in an amount different from that normally observed in nature. Of particular interest are recombinant thiaminases and recombinant thiaminase derivatives.

In accord with the above methods for inducing apoptosis and for treating neoplastic disorders, the invention also provides a pharmaceutical composition which includes at least one thiamin-depleting agent. Such a thiamin-depleting agent may be of any type, such as those pointed out above. Thus, in preferred embodiments, the thiamin-depleting agent is thiamin-cleaving compound such as a thiaminase or thiaminase derivative, a thiamin-binding compound or derivative, or a thiamin antagonist. Also, in preferred embodiments, the composition also includes a delivery targeting component. Such a component results in preferential delivery of the agent to a selected group of cells. Also in preferred embodiments, the composition includes a pharmaceutically acceptable carrier or excipient. Also in preferred embodiments, the composition includes a plurality of thiamin-depleting agents, and/or the composition includes an anti-neoplastic agent other than a thiamin-depleting agent. In these and other preferred embodiments, the thiamin-depleting agent, and other components of the pharmaceutical composition have characteristics as described above. Thus, preferred embodiments of such pharmaceutical compositions include compositions with components as described in other aspects herein or in the Detailed Description.

In a related aspect, the invention provides a method for making a pharmaceutical composition which includes a thiamin-depleting agent or a plurality of such agents. The method includes identifying a compound having thiamin-depleting activity, synthesizing the compound in an amount sufficient to produce a therapeutic effect by the induction of apoptosis of a selected group of cells, and preparing the compound in a pharmaceutically acceptable composition. Preferably the thiamin-depleting activity is thiamin-cleaving activity.

Similarly, the invention provides a method for making a pharmaceutical composition which includes a nucleic acid sequence encoding a thiamin-depleting agent. The method involves identifying a nucleic acid sequence encoding a peptide or polypeptide having thiamin-depleting activity, synthesizing the nucleic acid sequence in an amount sufficient to produce a therapeutic effect by the induction of apoptosis of a selected group of cells by expression from the nucleic acid sequence, and preparing the nucleic acid sequence in a pharmaceutically acceptable composition.

In preferred embodiments, the above aspects concerning methods of making, the composition includes components as described in other aspects for pharmaceutical compositions or compositions utilized in methods of inducing apoptosis, methods of killing cells, and methods of treating a disorder, or other methods of utilizing thiamin-depleting agents as described herein.

In this context, the term "synthesizing" refers to the artificial production of a molecule from one or more precursor molecules. Such production may involve chemical synthesis and/or may involve expression from a nucleic acid template. Such production may involve preparation of a molecule by combining two or more molecules, such nucleotides or amino acids, and/or may involve chemical modification of a single molecule, such as by the addition or removal of one or more substituent groups.

In view of the use of thiamin-depleting agents to induce apoptosis of vertebrate cells by reducing the level of thiamin, the invention also provides a method for identifying thiamin-depleting agents able to induce apoptosis of vertebrate cells. The method involves providing and contacting vertebrate cells with a compound having antithiamin activity. The induction of apoptosis of the cells indicates that the compound has the specified apoptosis inducing ability. Preferably, the cells are in contact with the anti-thiamin compound for a significant period. The appropriate time period can be selected based on the characteristics of the cells and the expected time needed to induce apoptosis of the cells by thiamin-depletion. In preferred embodiments the time period is within a factor of about two of the time previously observed for the induction of apoptosis using *Naegleria gruberi* thiaminase in vitro, preferably a period of about 3-30 days, more preferably about 3-20 days, still more preferably about 3-10 days. An appropriate time period also can relate to the type of antithiamin activity which it is desired to detect. Thus, a longer period may be useful for detection of thiamin-binding compounds than thiamin-cleaving compounds. Those skilled in the art will recognize that the test period can be adjusted based on empirical evaluation of results obtained.

In the context of this invention "antithiamin activity" refers to a chemical or biological reaction or interaction which reduces the ability of a cell to utilize thiamin provided in the cellular environment. Thus, such an activity includes, for example, a thiamin-cleaving activity such as that of thiaminases. It also includes thiamin-binding activity such as that of previously identified thiamin-binding compounds or other thiamin sequestering effect. It further includes thiamin antagonist activity which can, for example, include competitive binding of the antagonist to thiamin carriers or enzymes which utilize thiamin as a substrate. The antithiamin activity can also include the inactivation or inhibition of an enzyme or other biomolecule which is necessary for the cellular incorporation of thiamin.

In preferred embodiments, the compound having antithiamin activity is a thiamin-cleaving compound, such as a thiaminase or thiaminase derivative, a thiamin-binding compound or derivative, or a thiamin antagonist.

In view of the useful treatment methods involving thiamin-depleting agents, the invention also provides a method of screening for such agents. The method involves contacting thiamin in solution with a plurality of test compounds and determining whether any of the compounds have antithiamin activity, where the antithiamin activity is a thiamin-cleaving activity or a thiamin-binding activity. Preferably, the compounds being tested are small molecules or are compounds selected on a chemical structural basis to be likely to have the antithiamin activity.

In another related aspect, the invention provides a method of screening compounds having antithiamin activity by contacting cells which do not synthesize thiamin but which require the presence of thiamin with one or preferably more test compounds and determining whether the presence of the test compound inhibits the cellular uptake or utilization of thiamin by the cell. The inhibition of cellular uptake or utilization of thiamin is indicative that the test compound is a thiamin antagonist. In preferred embodiments, the inhibition of uptake or utilization of thiamin is provided by an antithiamin activity as described above, such as thiamin-cleaving activity, thiamin-binding activity, competitive inhibition, and inhibition of an enzyme required for thiamin utilization.

The invention also provides a method for screening synthetic compounds or derivatives of compounds to identify compounds having antithiamin activity. The method involves testing a plurality of compounds to determine whether the compounds have activity against thiamin in solution. In some embodiments in which derivatives of compounds having antithiamin activity are screened, the derivatives are not mutated forms of *Bacillus thiaminolyticus* thiaminase, or are not derivatives of that thiaminase. In preferred embodiments, the plurality of compounds are at least a portion of a compound library, such as a synthetic compound library or a combinatorial library, or derivatives of thiaminases or thiamin-binding compounds. Also in preferred embodiments, the antithiamin activity being determined is thiamin-cleaving activity or thiamin-binding activity.

The term "method of screening" refers to a method for evaluating a plurality of test compounds to determine whether one or more test compounds possess a particular functional property and may also determine the level of activity associated with that functional property, but is distinct from a method for merely evaluating the level of activity of a compound which is known to have a particular activity. The method of screening is suitable for and is used to evaluate a plurality, preferably a large number of test compounds, e.g., at least 10, more preferably at least 100 and still more preferably at least 1000 test compounds.

In an alternative to the use of thiamin depleting agents for the therapeutic induction of apoptosis, a treatment can be utilized which acts on at least one critical step or component in the cellular apoptosis pathway that is activated as a consequence of thiamin depletion. Thus, for example, the treatment can modulate, usually inhibit, a step in a crucial metabolic pathway, or the transmission of a signal through a signaling receptor. Preferably, the treatment involves the localized administration or activation of a compound, leading to apoptosis. The targeting or localization may be accomplished by a variety of means, including those described herein, selected as appropriate for the type of treatment or molecule to be administered.

In the context of the apoptosis induction pathway associated with thiamin deficiency, the term "critical" means that appropriate modulation of the step or activity of a component or reaction results in the induction of apoptosis. This does not require, though it is preferable, that the step be essential to all pathways in the induction of apoptosis. For example, alternate reactions to an inhibited reaction may also induce apoptosis, but even if there are multiple pathways to apoptosis, all that is needed is that one crucial step or activity be modulated such that apoptotic cell death is triggered.

Still further, this invention provides additional methods for inducing apoptosis of a selected group of cells by creating a localized deficiency of a nutritional factor different than thiamin. Deficiencies of a number of different nutritional factors in addition to thiamin induce apoptosis. It has, for example, been demonstrated that depletion of iron or glucose induces apoptosis of cells. Thus, depletion of such a nutritional factor in the targeted group of cells can be used as described herein for thiamin deficiencies. Such targeted nutritional deficiencies can be used in place of or in addition to a localized thiamin deficiency. In addition, deficiencies of certain other nutritional factors do not induce apoptosis, but do induce quiescence. An example of such a quiescence-inducing factor is isoleucine. Factors which induce quiescence are thus not useful for directly inducing apoptosis, but could be used in conjunction with a thiamin deficiency or other apoptosis-inducing nutritional factor deficiency (or even other apoptosis-inducing methods) in cases where the apoptosis induction only or predominantly takes place with quiescent cells rather than actively growing cells in order to increase the proportion of quiescent cells among the targeted cells.

In preferred embodiments, such methods include the targeting methods or agents or other composition components, or accessory methods as described in connection with the use of LAIDT above.

Other features and advantages of the invention will be apparent from the following description of the preferred embodiments and from the claims.

DETAILED DESCRIPTION OF THE PREFERRED EMBODIMENTS

Figure 1:
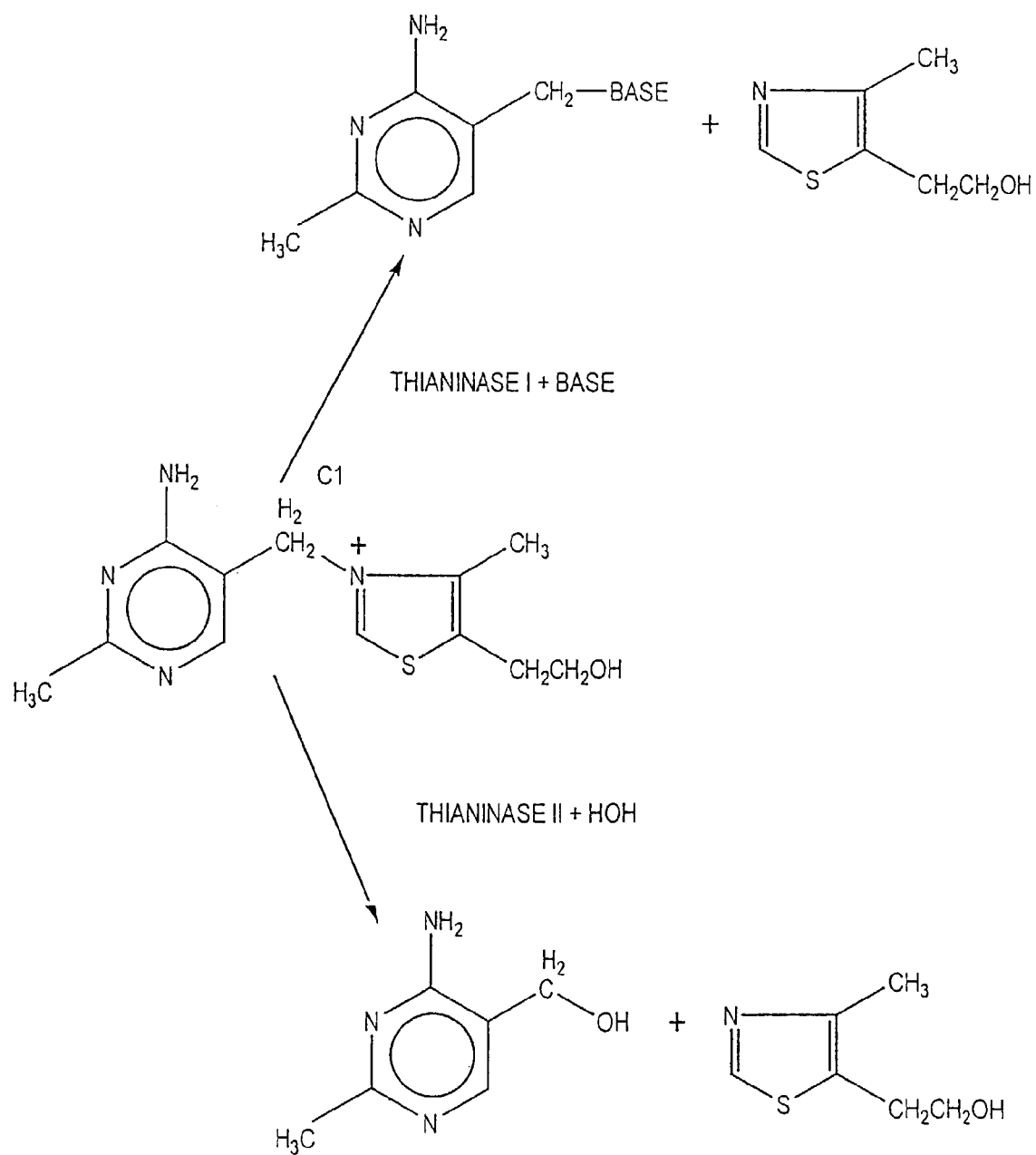
FIG. 1 is a diagram showing the cleavages of thiamin catalyzed by thiaminases I and II. Both thiaminases cleave the methylene bridge between the pyrimidine and thiazole moieties of thiamin, one by a base-exchange reaction and the other by hydrolytic cleavage.

I. Introduction
  A. Brief Description of the Invention.

The present invention brings together three disparate areas: a) the programmed death or apoptosis of vertebrate cells, b) an agent in the unicellular protist *Naegleria* that causes apoptosis, especially of growth-arrested cells, and c) thiamin deficiency.

Induction of apoptosis of selected cells in vivo provides a non-surgical means to eliminate unwanted cells. With the induction of apoptosis in specific cells, it is possible for an apoptosis-inducing agent to seek and eliminate cells that may be displaced from the original site (e.g., metastases) or inaccessible (e.g., in the brain).

A particularly useful application of targeted apoptosis is in treatment of cancer. Other uses could include, but are not limited to, eliminating specific unwanted cell types that are not essential. The present invention is illustrated primarily by the description of embodiments for cancer therapy, however, this invention is not limited to cancer therapy; approaches similar to those illustrated could be used to induce apoptosis in selected cells other than cancer cells. The focus on cancer therapy is for illustrative purposes and should not be considered to limit the invention to this use.

Thus, this invention introduces a therapy for killing unwanted cells, tissues, tumor masses or organs in vivo by inducing the selected cells to undergo apoptosis. Apoptosis is induced by reducing the level of thiamin in the target cells.

The thiamin deficiency may be created by a variety of methods, including the administration of any of the following "agents," which generally would be prepared as a pharmaceutical composition or nucleic acid delivery formulation:

(a) a thiamin-degrading or -cleaving agent, including thiaminase and derivatives thereof, (b) a thiamin-sequestering agent or derivative, (c) a thiamin antimetabolite, such as pyrithiamin or amprolium, or (d) a gene that encodes a polypeptide that acts as (a) or (b), either destroying or sequestering thiamin.

Agents (a) and (b) can be either polypeptides or synthetic smaller molecules. Agents (a) and (b) can act externally to the target cells, or internally. Agent (a) has the advantage of amplifying its effectiveness through destruction of multiple thiamin molecules. Agents (c) and (d) only act intracellularly or by blocking transport of thiamin into cells. Agent (d) can encode a thiamin-depleting agent that acts either intracellularly or is secreted into the environment surrounding the target cells. Any method that prevents thiamin from reaching the target cells rapidly creates a deficiency as the intracellular thiamin is used up.

The agents that reduce the level of thiamin may be directed to the target cells by any of several means, including but not limited to:

(1) they can be conjugated to antibodies that bind antigens enriched on the target cells or their surrounding matrix.

(2) they can be conjugated to ligands that bind to receptors enriched on the target cells.

(3) using either antibodies or ligands, they can be targeted to antigens or receptors on the endothelial cells of capillaries that bring thiamin to the target cells.

(4) they can be protected or carried in coatings, liposomes, or nanospheres, or other protective components. Such components, carriers or coating can, in turn, be directed to the targeted cells as in (1), (2), and (3).

(5) they can be targeted to hypoxic solid tumors by allowing these oxygen-deficient regions to be infected with a genetically engineered anaerobic bacterium such as *Clostridium* that will colonize the tumor and there release the agent, or by expressing the agent from a nucleic acid sequence inducible under hypoxic conditions.

(6) they can be targeted by having the agent activated by a specific enzyme normally associated with the target cells, e.g., by using the specific serine protease "prostate-specific antigen" associated with prostate carcinoma cells.

(7) they can be directly localized, either into a third space such as the peritoneum, cerebrospinal fluid, or bladder, or intraarterially by introducing the agent directly into an artery directed toward the target cells, or directly into a target tissue or tumor.

(8) they can be introduced using live bacteria as vectors into certain places in the body where bacteria can colonize as normal flora, especially the gastrointestinal tract, the vagina, or even the bladder. In each such place, a suitable genetically engineered bacterium can harmlessly colonize and release the agent into its surroundings. In the case of the intestine, the agent can be directly localized by oral doses of a suitable thiaminase instead of a thiaminase-secreting bacterium.

(9) they can be introduced into the lung tissue by pulmonary absorption.

Slight variations on these methods of targeting depend on whether the agent being delivered is a polypeptide, a peptidomimetic compound, a small molecule, a ribozyme, or an encoding DNA, but most of the targeting methods can be adapted to each of the various agents. Such adaptations are understood by those skilled in the art. In addition, other methods of targeting agents to selected cells or tissues are known to those skilled in the art and can be used in this invention.

As primary examples of target cells to be killed, the description focuses on cancer cells, for which therapies are urgently needed. Specific approaches are mentioned for many cancers, including lung, nerve-cell (gliomas), bladder, ovary, skin (melanomas), as well as all cancers that form hypoxic solid tumors. More specific approaches to thiamin-depletion therapies are described for prostate cancer, breast cancer, and colorectal cancer.

Therapies can be combined, so that several thiamin-depleting treatments could be directed toward a single cancer or other condition, or a thiamin-depleting therapy could be used in conjunction with one or more other therapies, e.g., with conventional chemotherapy or radiation treatment, or with antiangiogenesis methods. Several types of combination therapies are described below.

In addition to cancer therapy, the agents and targeting methods allow therapeutic elimination of other unwanted cells, including but not limited to:

1) sterilization by selective elimination of male or female gametes or gamete-producing cells, 2) elimination of specific glandular tissue, such as thymus, in cases of hypertrophy or disease, 3) elimination of undesirable antigen-bearing cells, such as cells that recognize a self-antigen and cause disease or, 4) elimination of cells infected by a particular virus or parasite.

Side effects of the administration of thiamin-depleting agents are expected to be minimal when compared with conventional anticancer treatments such as radiation and conventional chemotherapy. It may be possible to provide embodiments using a thiamin depletion approach which will kill 100% of the target cells with minimal untargeted damage to the patient.

These methods also provide additional advantageous characteristics not available in most existing modalities of cancer therapy, such as:

1) the invention effectively kills non-proliferating cells, so it is not restricted to actively growing cells. For many situations, such as androgen-independent prostate carcinoma, the ability to kill non-cycling cells is urgently needed.

2) it kills cells independently of the expression of the bcl-2 oncogene. Expression of bcl-2 makes cells resistant to induction of apoptosis by many other therapies.

3) it kills cells independently of the expression of the p53 tumor suppressor gene.

4) the agents, in forms (a) and (b), can act outside of cells, and thus can surround a cell mass, reducing the level of thiamin and leading to apoptosis of the surrounded cells. As a consequence, not every cell needs to be directly targeted to be killed.

Finally, the apoptosis-inducing agent has a simple antidote, thiamin, which can reverse the process at any time until morphological cell death. This antidote is always available in case untargeted cells are affected at an unacceptable level or an excessive overall thiamin deficiency is created in the patient.

This therapeutic approach is applicable in certain cases where no satisfactory therapies currently exist, such as for treatment of metastatic cancers of the breast, colon, and prostate.

B. Limitations of Current Methods of Inducing Apoptosis

Agents that are commonly used in vivo for chemotherapy, such as cisplatin, as well as radiation therapy of cancers, often work by inducing apoptosis. These agents generally have considerable toxicity to the whole animal, and it is often difficult or impossible to adjust treatments such that they will kill the tumor or metastases without severely weakening if not killing the animal or person being treated. Thus, the "therapeutic window" is often frustratingly narrow, especially as tumor cells become resistant to agents that induce apoptosis in normal cells. In addition, the standard treatments are difficult to localize; radiation treatments usually are localized simply by shielding, and drugs by injection into particular sites.

In addition, these treatments have other limitations including:

a) They affect primarily cells that are growing (including, e.g., rapidly growing tumor cells as well as stem cells), and have less or no effect on cells that are not actively traversing the cell cycle. Since many cells, even in malignant tumors, are not always actively cycling, this markedly limits the effectiveness of the treatment (Kyprianou et al., 1991).

b) Their effect is much diminished by oncogenes that often arise in cancer cells. For example, the effectiveness of most chemotherapeutic agents is compromised by the expression of bcl-2 or by the lack of functional p53, either or both of which commonly occur in cancer cells.

II. Thiamin

A. A Cytopathic Agent in the Protist *Naegleria*

In 1969, Schuster described a "virus-like particle" in strain $EG_S$ of the ameboflagellate, *Naegleria gruberi*, a unicellular eukaryote which has been used to study cell differentiation (e.g., Fulton and Dingle, 1967; Fulton, 1977; Fulton, 1993). This observation led to attempts to determine whether this *Naegleria* strain contained an agent which could infect vertebrate cells. It was found that freeze-thawed extracts of cells of strain $EG_S$ contained a filterable agent that caused vertebrate cells to undergo a response that mimicked a virus infection: the vertebrate cells grew, but then died and lysed (Dunnebacke and Schuster, 1971). The agent was shown to also occur in a strain of *Naegleria* that did not contain the virus-like particles. The infective agent was subsequently named "*Naegleria* ameba cytopathic material" or NACM.

We confirmed that extracts of *Naegleria* cause cytopathology in vertebrate cells in culture at a total extract protein concentration of $\leq 0.1$ μg per liter. We studied this cytopathology, and found that, in fact, the *Naegleria* agent induces programmed cell death, with all the morphological characteristics of classical apoptosis as well as degradation of DNA to nucleosome-sized fragments.

We have found that the phenomenon of apoptosis induced by the *Naegleria* agent has several unique features:

1) The agent has no effect on the growth of vertebrate cells in culture.

2) The agent is quite stable in the cell cultures, retaining about half its activity after a week at 37° C.

3) The cells undergo apoptosis when two conditions are met:

a) The cells are in the presence of the agent for a substantial time, which varies for different cell lines from a minimum of 4 days to a maximum of about 13 days. The time required is called the latent period.

b) The cells must reach stationary phase or be growth arrested (i.e., exit the cell cycle, or stop cycling).

4) The cells must be in the continual presence of the agent until near the time morphological features of apoptosis are evident.

5) When these conditions are met, every cell in the culture undergoes apoptosis within a time span of 12-48 hours depending on cell line.

6) Apoptosis may be averted by rinsing the cells to remove the agent as little as 2.5 hours before cell death is morphologically evident.

7) The cells use existing machinery for this apoptosis, since its occurrence is independent of RNA and protein synthesis.

These conditions have interesting consequences. For example, cells may be grown and subcultured in the presence of the *Naegleria* agent for as long as 100 days without undergoing apoptosis as long as the cells grow continuously and are never allowed to stop cycling. As soon as such a cell population exits the cell cycle, the cells die.

Our experiments indicate that the agent induces apoptosis in all of many vertebrate cell lines tested, ranging from primary cultures of chick embryo fibroblasts to diverse human cancer cell lines.

The following properties of apoptosis induced by the *Naegleria* agent offer unique therapeutic opportunities:

a) The *Naegleria* agent itself is not toxic to vertebrates or vertebrate cells.

b) The agent induces apoptosis independently of the expression of bcl-2 protein. Since this proto-oncogene, often expressed in cancer cells, functions to prevent apoptosis induced by many agents, agents that kill cells expressing bcl-2 are valuable in the attack on tumor cells.

c) The agent induces apoptosis in cells independently of their ability to express the p53 gene. This tumor-suppressor gene is often absent in tumors, and its absence indicates a poor prognosis for therapy. Ability to kill cells that lack the p53 protein is a considerable therapeutic advantage.

d) The agent kills non-cycling cells. Since many cells in solid tumors are non-cycling ("dormant"), they are not susceptible to most chemotherapeutic agents or radiation. The availability of an agent that can kill cells that are not actively proliferating is a powerful addition to the arsenal of agents for cancer therapy, the need for which has been stressed by others (Hickman et al., 1994; Denmeade et al., 1996).

e) In vitro, the agent kills $\approx 100\%$ of cells; it leaves $<10^{-6}$ survivors.

f) The *Naegleria* agent acts outside of cells, so it only has to be in the environment of the cells to have its effect. Gene therapy, endogenously induced gene expression, or introduction of the agent into cells are possible but not necessary for this agent to induce apoptosis.

Each of these features offers great advantages for therapeutic uses of the *Naegleria* agent.

B. Effects of Systemic Thiamin Deficiency

As indicated, our approach to inducing apoptosis of selected cells in vivo involves creating a localized thiamin deficiency (or otherwise activating this apoptotic pathway). Among several methods of achieving this, certain preferred embodiments are enzymes that destroy thiamin, called thiaminases. It is thus useful to understand aspects of thiamin deficiency and of thiaminases.

Requirements for thiamin (thiamine, vitamin $B_1$, aneurin) have been defined in diverse organisms, including prokaryotic and eukaryotic microorganisms and diverse multicellular animals (metazoa). Thiamin is often spelled thiamine, since it was originally thought to be an amine. The spelling, thiamin, used herein is recommended (see Friedrich, 1988, p. 343).

Thiamin appears to be essential in the diet of all higher animals. Requirements for thiamin have been demonstrated in diverse birds and mammals including humans (Cowgill, 1939; Wolstenholme, 1967). Such dietary requirements are absolute unless production of the vitamin by intestinal microorganisms is sufficient to meet the requirement of the animal host. Examples of synthesis of thiamin by intestinal bacteria have been demonstrated in several mammalian species, including rabbits (which obtain their thiamin by ingestion of their feces and digestion of thiamin-containing intestinal flora) (Mickelsen, 1956). In general, thiamin must be provided in food, and insufficient thiamin in food causes thiamin-deficiency diseases.

The human thiamin-deficiency disease, beriberi, has been known in Asia for centuries. In the nineteenth century and the first three decades of the twentieth century beriberi reached epidemic proportions, beginning as a consequence of the widespread consumption of polished rice and ending when the role of vitamin $B_1$ was elucidated. Since then beriberi has been a rare disease, although clinical thiamin deficiency is common in alcoholics (Wernicke's disease) and subclinical deficiency is found in several groups of people (Friedrich, 1988). While beriberi was being conquered, thiamin and thiamin deficiency were extensively studied (reviews: Harris et al., 1954; Williams, 1961; Shimazono and Katsura, 1965; Wolstenholme, 1967; Sable and Gubler, 1982; Friedrich, 1988). Since that time, there has been less interest.

In humans, thiamin deficiency leads to a loss of appetite (anorexia) and nausea, and subsequently neurological and cardiovascular symptoms develop (Platt, 1967). In some patients, the neural symptoms ("polyneuritis") prevail, and the patient becomes inactive and emaciated. In others, especially in patients who remain active, cardiovascular symptoms are more prominent, leading to heart enlargement and sudden failure. When thiamin is provided to such patients, even the cardiac hypertrophy melts away "as snow in the sun" (Wenckebach, 1928). Detailed histological descriptions of beriberi symptoms reveal "fatty degeneration . . . , congestive changes . . . , atrophy of [nerve] fibers . . . " and other changes (Inoue and Katsura, 1965).

As described, these degenerative changes in tissues are not suggestive of apoptosis, but it cannot be determined from these descriptions whether or not apoptosis was induced in the tissues, since evidence was not sought and apoptotic cells are removed from tissues rather quickly in vivo (Cohen et al., 1992). (For our use of thiamin deficiency to induce apoptosis, it does not matter whether or not beriberi symptoms involve apoptosis.) Even with a total absence of thiamin in the diet, it takes about twenty days before deficiency symptoms appear in humans, and then several weeks to the end stages of the disease (American Medical Association, 1939).

The symptoms in other mammals and in birds are superficially similar to those in humans, although each species shows its own characteristic response to thiamin deficiency, perhaps depending on where in the body a critical deficiency of thiamin first appears (Peters, 1963, p. 20). Birds were often used in studies of thiamin deficiency, since with a thiamin-free diet they develop polyneuritis in as little as ten days (Cowgill, 1939; Harris et al., 1954; Peters, 1963).

In a rat model of Wenicke's encephalopathy, the effects of thiamin administration at various neurological stages of pyrithiamin-induced thiamin deficiency were determined (Zhang et al., 1995, *J. Neuropathol. Exp. Neurol.* 54:255-267). It was shown that thiamin treatment was more effective when administered at earlier stages. Zhang et al. stated that the results "suggest that excitotoxic and possibly apoptotic mechanisms may mediate neuronal degeneration in the PTD rat model of Wenicke's encephalopathy and that multiple factors conducive to excitotoxicity may act in concert to produce this syndrome."

Thus, although thiamin deficiency has been associated with clinical diseases of man and other animals, including death of these animals, apparently thiamin deficiency has not previously been shown to be directly associated with induction of apoptosis.

Thiamin has several clearly defined, crucial roles as a cofactor ("cocarboxylase") in several enzymes of energy metabolism (Haake, 1987; Friedrich, 1988). The active intracellular derivative of thiamin, thiamin pyrophosphate (TPP) (sometimes called thiamin diphosphate), serves as the cofactor of several essential enzymes, including pyruvate decarboxylase, transketolase, α-ketoglutarate dehydrogenase, and others. All these TPP-dependent enzymes cleave and form bonds adjacent to carboxyl groups. Deficiencies in these enzymes cause severe metabolic consequences, ranging from a decline in energy production to acidosis caused by the accumulation of lactic acid.

Thiamin has also been implicated in special roles in the nervous system (Minz, 1938; von Muralt, 1947; Woolley and Merrifield, 1954; Cooper and Pincus, 1967), and another phosphorylated derivative, thiamin triphosphate, is abundant in nervous tissue (Friedrich, 1988).

Thiamin is not stored in the body; it is depleted, most likely as enzymes to which thiamin diphosphate is tightly bound as coenzyme decay. A human contains 25-30 mg of thiamin, mostly as TPP (Harris et al., 1954; Wilson, 1991). Thiamin in the body has a half-life of 9-18 days (Friedrich, 1988). As a consequence of turnover humans require a minimum of about 0.7-1.5 mg of thiamin per day. Any excess taken in the diet is eliminated in the urine.

Thiamin deficiency itself may have some selective effect on the growth of tumors, although the results to date allow alternative interpretations. Treatment of mice and rats bearing experimental tumors, especially Ehrlich's ascites cancer, with oxythiamin, hydroxythiamin, or various analogues of these antimetbolites, causes both a thiamin deficiency and reduced growth of the tumor (Ostrovsky et al., 1985: Zimatkina et al., 1986; Trebukhina et al., 1987; Ostrovsky, 1991; Zimatkina et al., 1996; Boros et al., 1997). For example, Trebukhina et al. (Trebukhina et al., 1987) found that oxythiamin decreased the growth of Walker's sarcoma in rats by 45%. Boros et al. (Boros et al., 1987) reported 90% inhibition of the growth of Ehrlich's ascites tumor cells in mice with no toxicity observed during three days of treatment (no further observations were reported). Such treatment might have promise for cancer therapy except that even though the thiamin analogues inhibit the growth of tumors (especially ascites tumors), because of their toxicity most of the analogues do not extend the life span of the animals with tumors. A group in Belarus has synthesized new analogues for many years, seeking analogues with different enzyme specificity and less toxicity. For example, thiamin analogue TA-10-2 caused a 72% reduction in the growth of ascites tumor, as compared to untreated tumor-bearing controls, but the life span of the animals was shortened to only 11 days as opposed to 18 days for the untreated tumor-bearing animals (Ostrovsky, 1991). Other analogues were more successful, for example, in the same experiments, TA-60-4 decreased the volume of the tumor 63% and increased the life span of the mice 1.7-fold. A recent study reported a compound that increased the life span of mice bearing ascites tumors 3.3-fold over untreated mice with tumors (Zimatkina et al, 1996). It is evident that this method of cancer therapy will become useful only if less toxic, more effective analogues can be developed. On the other hand, the targeted use of such analogues, to create LAIDT, as described for the present invention, should avoid the generalized toxicity.

It is uncertain whether oxythiamin and related analogues act on tumor growth via their known inhibition of enzyme that use thiamin as a coenzyme. In one study, hydroxythiamin was effective, but so was just the pyrimidine portion of the molecule, hydroxypyrimidine alone (Oparin and Zabrodskaya, 1992). This indicates an intact thiamin analogue is not necessary for the inhibition of tumor growth, suggesting that the inhibitory effect may be unrelated to the function of thiamin, yet other reports suggest a correlation between the effectiveness of thiamin analogues on tumor growth and their effect on thiamin-dependent enzymes (e.g., Zimatkina et al., 1996). In addition, thiamin deficiency caused by lack of dietary thiamin has not been reported to have a significant effect on the growth of tumors in experimental animals (e.g., Trebukhina et al., 1982; Trebukhina, 1983; Trebukhina et al., 1986). In humans, there are many reports of thiamin deficiency in people undergoing cancer therapy, either due to overall malnutrition (cachexia) or to intravenous feeding with inadequate thiamin supplementation (e.g., Basu et al., 1974; Seear et al., 1992; Geogiannos et al., 1993; and others cited in Boros et al., 1998). None of these reports have noted any effect of the thiamin deficiency on the progression of tumor growth by certain thiamin analogues. Thus, in view of the lack of antitumor effect of nutritional thiamin deficiency, the basis of the reported tumor inhibition by thiamin analogues is unclear.

C. Thiaminases and other Antithiamin Substances

Substances that selectively destroy or inactivate thiamin provide the ability to produce localized thiamin deficiencies in vivo. Several such substances have been identified, mostly as the result of studying thiamin deficiencies in animals and in people. Prominent among these "antithiamins" are thiaminases, enzymes that cleave the methylene bridge between the pyrimidine and thiazole moieties of thiamin. Thiaminases were much studied from the 1940s to the 1960s; the emphasis of studies on thiaminase in these decades is shown by years in which research on thiaminase was reviewed (Yudkin, 1949; Harris, 1951; Fujita, 1954; Murata, 1965; Evans, 1975; Murata, 1982). There have been only scattered studies of thiaminases in recent years, and, in view of our investigations and invention, much of what is known about these enzymes should be reinvestigated using modern techniques.

Thiaminases and other antithiamins have not been previously examined in relation to cancer therapy or to apoptosis.

Most organisms do not appear to have any thiaminase activity. None has been found in mammals or birds (e.g., Harris, 1951; Puzach, 1991). The few organisms that possess these enzymes are phylogenetically diverse, and nothing about the habits of these organisms has given any clue as to why they possess thiaminase.

Two types of thiaminases have been described, thiaminases I and II. FIG. 1 shows the cleavages catalyzed by thiaminases I and II (from Edwin, 1979). Both thiaminases cleave the methylene bridge between the pyrimidine and thiazole moieties of thiamin, one by a base-exchange reaction and the other by hydrolytic cleavage.

Thiaminase I (EC 2.5.1.2) cleaves thiamin by an exchange reaction with a nitrogen base or a sulfhydryl group; nucleophilic displacement of the methylene group of the pyrimidine part separates it from the thiazole part. When purified, this transferase class of thiaminases are active only in the presence of a suitable cosubstrate, such as an aromatic amine or a heterocyclic base (e.g., aniline, pyridine, proline, niacin) or sulfhydryl compound; suitable compounds are abundant in most tissues. This class of thiaminases have been found in some shellfish, some fresh-water fish, a few plants, especially ferns, and scattered bacteria (including *Bacillus thiaminolyticus* and *Clostridium sporogenes*). (We describe herein the presence of a thiaminase I as an intracellular enzyme in a single-celled eukaryotic protozoan, *Naegleria gruberi*.)

Thiaminase II (EC 3.5.99.2) causes simple hydrolysis of thiamin to pyrimidine and thiazole. These thiamin hydrolyases are found in a few bacteria, including *Bacillus aneurinolyticus*, and in some fungi (listed in Murata, 1965). Thiaminase II has been found at a low level in baker's yeast, *Saccharomyces cerevisiae* (Kimura and Iwashima, 1987).

The two classes of thiaminases can readily be distinguished by whether or not they are dependent on a cosubstrate. Before the requirement of thiaminase I for a cosubstrate was recognized, workers were often confused by unaccountable loss of enzyme activity upon purification and often ascribed antithiamin activity to the cosubstrate. In addition, the two classes of enzyme differ in their requirements within the structure of thiamin. For example, thiaminase I requires an amino group on the 4 position of the pyrimidine, and thiaminase II requires a side chain on the 5 position of the thiazole, but not vice versa (Murata, 1982).

1. Distribution and Pharmacology of Thiaminases

Organisms that have thiaminase have normal thiamin content in their tissues while alive, and it seems likely that within the living cells that produce them, the thiaminases are normally inactive as a catalyst of thiamin destruction. In contrast, multicellular thiaminase-producing organisms often have no detectable thiamin in their tissues hours after the death of the organism. Thiaminases of animals and plants become active upon death of the organism, or through homogenization or other release from the cells (Harris, 1951; Fujita, 1954; Murata, 1965; Friedrich, 1988). The bacterial thiaminases are predominantly extracellular; they are excreted into the medium.

Any toxicity of thiaminases to animals appears to be the result of the degradation of thiamin, and the symptoms have been promptly curable by the administration of thiamin so long as the antidote is provided soon enough. Thus thiaminases appear to exert no effect on animals other than through the degradation of thiamin.

2. Fish Thiaminases

Thiaminase was first discovered when it caused a thiamin deficiency. Foxes fed a wet mash of carp or carp entrails developed "Chastek paralysis." This disease could be cured by thiamin, and was shown to be a thiamin deficiency caused by a factor in the carp (Green et al., 1941). The factor was subsequently shown to be an enzyme that degraded thiamin, a thiaminase (Woolley, 1941; Krampitz and Woolley, 1944).

The thiaminase in entrails of carp and some other fish has also caused thiamin deficiencies in trout (a fish that lacks thiaminase), chickens, pigeons, rats, and cats (Alexander et al., 1941; Spitzer et al., 1941; Smith and Proutt, 1944; Harris, 1951). In all cases, cooked carp did not cause any deficiency, the deficiency could be prevented by providing a sufficient excess of thiamin in the diet, and animals showing deficiency recovered if given large doses of thiamin.

In foxes, and probably in all these cases, the thiamin deficiency appears to be caused primarily by destruction of thiamin in the wet mash by the fish thiaminase before the food is consumed, rather than action of the thiaminase in the gut after ingestion. In fact, raw carp fed to foxes as a separate meal was harmless—the thiaminase apparently has to act on the food before it is eaten to cause a deficiency (Green et al., 1942). There is no indication that fish thiaminase can survive passage through the digestive system.

Thiaminase in carp and other fish is found mainly in the viscera—intestines, kidney, spleen (Sealock et al., 1943; Fujita, 1954). Little is found is muscle, the part of fish normally eaten by humans, including those who consume raw fish. About half of the fresh-water fish tested contained thiaminase, including all members of the carp family Cyprinidae (Deutsch and Hasler, 1943). Thiaminase is generally not found in marine fish, but there may be exceptions (Deutsch and Hasler, 1943; Melnick et al., 1945; Deolalkar and Sohonie, 1954; Fujita, 1954).

Fish that possess thiaminase have normal levels of thiamin in their tissues and blood, but by the time they reach market the tissues are free of thiamin (Field et al., 1943; Murata, 1965).

Fish thiaminase cannot penetrate living yeast cells, with intact cell membranes, but it can destroy the thiamin of non-viable yeast (Deutsch and Ott, 1942).

Thiaminase has been partially purified from fish by Ågren (Ågren, 1945, described in Yudkin, 1949). This thiaminase remained stable in acetone powders for at least eight months at 4° C. (Sealock et al., 1943).

3. Shellfish Thiaminases

Thiaminase was found in some shellfish by Fujita in 1941 (see Fujita, 1954). The enzyme was discovered when some shellfish obtained at markets were found to be devoid of thiamin, and added thiamin was found to disappear. Thiaminase is found in some clams, but little if any is found in oysters (tabulated in Fujita, 1954). It is also found in lobsters and shrimp (Harris, 1951).

Eating raw clams caused destruction of thiamin in the gastrointestinal tract of animals and humans, including a reduction of the thiamin concentration in blood and urine (Melnick et al., 1945; Harris, 1951). Although raw shellfish are often consumed, there seem to be no reports of severe thiamin deficiencies in humans or animals induced by shellfish thiaminases.

The enzyme has been purified about 20-fold from clams (*Meretrix meretrix* in Japan and the quahog *Venus mercenaria* in the United States) (Fujita, 1955; Alston and Abeles, 1987) and from a fresh-water mussel (McCleary and Chick, 1977). Extracts of a fresh-water mussel could be stored at 4° C. for a week without loss of thiaminase activity (Reddy et al., 1948).

4. Fern Thiaminases

Fern thiaminases have been associated with production of severe thiamin deficiencies in animals. In particular, the fern bracken (*Pteridium aquilinum*) is a common, persistent weed in pasture lands in many parts of the world. When cattle include too much bracken in their forage it sometimes causes "fern poisoning," known since 1893 (references in Thomas and Walker, 1949). Bracken included in the diet also causes thiamin deficiency in experimental animals.

Bracken, air dried at room temperature and incorporated at 40% by weight into a ration otherwise sufficient in thiamin, induced thiamin deficiency in rats, which died within 30 days (Weswig et al., 1946; Thomas and Walker, 1949). Thiaminase-enriched extracts of bracken also produced thiamin deficiency (Evans et al., 1950). Rats already showing polyneuritis were given a large dose of thiamin (oral, 0.5 mg daily). While rats not given the vitamin died within several days, those given megadoses of thiamin "recovered with such remarkable promptness that gains of 22 to 49 gm for the 1st week were obtained" (Weswig et al., 1946). If the ration with bracken was supplemented with extra thiamin from the beginning, no vitamin deficiency developed.

The agent in bracken that causes thiamin deficiency is quite stable. It could be destroyed by autoclaving or boiling 10 min in water, but the dried fern could be heated at 105° C. for 18 h without loss of toxicity (Weswig et al., 1946).

Since dry bracken mixed with dry rations produces the deficiency, it is likely that the thiamin in the food is not destroyed before consumption, but rather that the bracken thiaminase produces a thiamin deficiency by action on the food in the digestive tract. The bracken enzyme apparently survives passage through the gastrointestinal tract of rats, as thiamin—digesting activity was found in the feces (Thomas and Walker, 1949). Some uncertainty exists about the ability of naked enzyme to survive the digestive tract, since some particles of the bracken powder may escape digestion (Evans, 1975, p. 495).

Bracken included in the diet also causes thiamin deficiency in other animals, including staggers in horses (cured by 50-100 mg thiamin per day) (Evans et al., 1950; Evans, 1975) and thiamin deficiencies in pigs and sheep (Evans, 1975). Japanese people often eat bracken, but only after soaking and boiling, which would destroy the thiaminase (Murata, 1965). When uncooked bracken was fed to human volunteers, at 15-24 g per day, it caused a depletion of thiamin (Parsons, 1953; Watanabe et al., 1955, cited in Fujita, 1954; Murata, 1965).

Bracken thiaminase has been partially purified from dried ferns (Kenten, 1957; McCleary and Chick, 1977). The enzyme was stable at −18° C. for at least 3-4 weeks (Kenten, 1957).

The Australian fern nardoo (*Marsilea drummondii*), whose clover-like fronds are often eaten by the Aborigines after appropriate preparation, has abundant thiaminase, up to 100-fold more than bracken (McCleary and Chick, 1977). Consumption of improperly prepared nardoo has caused thiamin deficiency and death in humans. In a dramatic example, three out of four members of a pioneering expedition across interior Australia in 1860-61 died of classical beriberi when they ran short of provisions and began to consume nardoo (Earl and McCleary, 1994).

The thiaminase I of nardoo has been partially purified and characterized (McCleary and Chick, 1977). The enzyme was quite stable; 50% was denatured at 60-65° C.

Several additional pteridophytes (ferns and their allies) that have been tested also have thiaminase (Fujita, 1954; Kenten, 1957; McCleary and Chick, 1977), including the horsetail *Equisetum arvense* (Evans et al., 1950). The thiaminases of bracken and nardoo, and apparently some of the others, are of the base-exchange type, thiaminase I. The thiaminase of one fern, *Dicranopteris glauca*, showed no activation by cosubstrate (aniline or other bases) and may be a thiaminase II (Fujita, 1954).

In general, other plants tested lacked thiaminase activity, with the notable exception of one angiosperm, the cockscomb *Celosia cristata*, which had a level of thiaminase I fourfold greater than bracken (Fujita, 1954). No pharmacological effects appear to have been associated with this plant, and its thiaminase has not been extensively studied.

5. Thiaminases in Bacteria and Fungi

If the intestinal flora has the right composition of microorganisms, it can provide some or all of the thiamin required by an organism (Mickelsen, 1956). A different microbial flora, in animals of the same species, can consume or destroy enough of the thiamin provided in the diet that a thiamin deficiency develops (Evans, 1975).

In ruminants a disease called cerebrocortical neurosis, cured by high doses of thiamin, is thought to be caused by thiaminase-secreting bacteria in the rumen (Friedrich, 1988).

In Japan, beginning in the late 1940s, thiaminase-producing bacteria were isolated from human feces (reviewed in Kimura, 1965). The first isolate was from a person suffering from a thiamin deficiency, and proved to be a new species, *Bacillus thiaminolyticus*, which produces thiaminase I. Fujimiya studied the frequency at which this bacterium was found in human feces, and found it in 2.9% of healthy individuals, 8.1% of beriberi patients, but also 6.9% of subjects with constipation and 10.8% of those with helminthiasis (Fujimiya, 1951, cited in Inoue and Katsura, 1965). In some individuals, thiaminases could be detected directly in an aqueous solution of feces; such people were said to have "thiaminase disease." Some of these people had beriberi or showed other symptoms of thiamin deficiency, such as a reduced level of blood thiamin. Other individuals showed no thiaminase activity but were "carriers" in that thiaminase-secreting bacteria could be isolated from their feces. These individuals were generally healthy, with normal thiamin levels. Matsukawa and Takato (cited in Kimura, 1965) found that thiaminase-secreting bacteria could be isolated from 100% of people with thiaminase disease. These and other studies in Japan suggested that a thiamin deficiency in humans was sometimes associated with thiaminase-producing bacteria in the intestine (reviewed by Fujita, 1954; Murata, 1965). However, Kimura believes this correlation is weak. In many cases thiaminase can be demonstrated in the feces of healthy individuals, and about 3-10% of individuals tested have thiaminase-producing bacteria without showing thiamin deficiency (Kimura, 1965). It remains uncertain how frequently thiaminase-producing intestinal bacterial are associated with subacute thiamin deficiencies in humans. Certainly the presence of thiaminase-secreting bacteria in the gastrointestinal tract is not, in itself, sufficient to consistently cause a thiamin deficiency.

Hens fed *B. thiaminolyticus* developed a thiamin deficiency and polyneuritis even though the diet contained an adequate amount of thiamin (Matsukawa et al., 1955). As soon as the orally introduced bacterium was detected in the feces, the thiamin level in the chickens decreased. Thiaminase activity could be detected from mid-ileum through the caecum. This result indicates that in chickens orally provided bacteria can colonize the intestine and cause a dramatic thiamin deficiency.

*B. thiaminolyticus* orally administered to animals was maintained easily in some, species, such as cats, but difficult to establish in others, including rabbits and goats (Hamada, 1954a). The bacterium fed to humans could be maintained in the intestine, at least short term. For example, among volunteers taking 4-8 mg of *B. thiaminolyticus* with their diet for 3-10 days, 7% developed "thiaminase disease," which became evident in 3-4 days and subsequently cured itself 9-13 days after discontinuance (Horikawa, 1951, cited in Fujita, 1954; see also Inoue and Katsura, 1965). Established *B. thiaminolyticus* could be eliminated from the gastrointestinal tract if the affected individuals were given lactic-acid bacteria or other treatments (Hamada, 1953; Hamada, 1954b; reviewed by Fujita, 1954; for a dissenting view see Kimura, 1965).

The most common isolate of a thiaminase-producing bacterium is *Bacillus thiaminolyticus*. This bacterium requires the pyrimidine and thiazole moieties of thiamin for growth, so its extracellular thiaminase (Douthit and Airth, 1966) presents no nutritional problem for the organism. The other studied aerobic species is *Bacillus aneurinolyticus*, which produces thiaminase II and releases it into the culture supernatant. A thiaminase-producing anaerobe, *Clostridium sporogenes*, has been isolated as well.

The thiaminases of each of these organisms have been purified from culture supernatants and characterized (early work reviewed by Murata, 1965). The thiaminase I of *B. thiaminolyticus* has been purified (Wittliff and Airth, 1968; Wittliff and Airth, 1970a). The enzyme can be stored at −20° C. for two years without loss of activity (Lienhard, 1970). This thiaminase I has been cloned in *Bacillus subtilis*, where the host makes and secretes mature enzyme, and also in *Escherichia coli*, where the enzyme accumulates in the periplasmic space, from which it can be isolated by osmotic shock (Abe et al., 1987). Recently the DNA encoding this enzyme has been sequenced, and shown to encode a 42 kilodalton protein. By site-directed mutagenesis, cysteine-113 of this thiaminase I has been identified as the active-site nucleophile (Costello et al., 1996). The thiaminase I of *C. sporogenes* has been purified and shows differences from the *B. thiaminolyticus* enzyme, including showing activation by $Ca^{2+}$ and inhibition by EDTA (Kobayashi, 1975a; Kobayashi, 1975b). The thiaminase II of *B. aneurinolyticus* also has been purified and characterized (Ikehata, 1960; Wittliff and Airth, 1970b).

We have found no direct reports of thiaminase deficiencies caused by thiaminase II of bacteria or fungi.

6. Comparison of Thiaminases of Different Organisms

A comparison of some properties of thiaminases is given in Table 1. The enzymes vary in the optimum temperature for activity, but are all quite thermostable (without comparative study using pure enzymes, the slight differences in thermostability cannot be considered significant). The *B. thiaminolyticus* thiaminase I is unaffected by 1 mM $CuSO_4$, which is inhibitory to the thiaminases found in the other organisms. Both of the listed bacterial enzymes are inhibited by iodoacetate, while the fish, clam, and bracken enzymes are not. Different cosubstrates have different effects. Aniline is an excellent stimulator of all the thiaminase I enzymes, but not thiaminase II. Pyridine and nicotinic acid are relatively better cosubstrates for fern and bacterial thiaminase I. The clam and fern thiaminases have molecular weights of 93-115 kilodaltons, about twice the bacterial thiaminase I. One possibility would be that the enzymes of the multicellular organisms represent dimers of a subunit near the size of the bacterial enzyme, although the purified bacterial enzyme has been shown to be a monomer (Costello et al., 1996).

TABLE 1

Selected properties of thiaminases

| Property | Thiaminase I | | | | II |
|---|---|---|---|---|---|
| Source of enzyme | Fish | Clam | Bracken | B.t. | B.a. |
| Optimum temperature (° C.) | 43 | 60 | 55 | 37 | 60 |
| Heat inactivation (min(° C.)) | 10(90) | 15(90) | 15(100) | 15(90) | 15(100) |
| Effect of $CuSO_4$ (1 mM) (% activity) | −47 | −30 | −86 | +4 | −98 |
| Sensitivity to iodoacetic acid | 0 | 0 | 0 | ++ | ++ |
| Percent activation by: | | | | | |
| aniline | 120 | 1500 | 690 | 700 | −30 |
| pyridine | 130 | 120 | 790 | 1100 | 0 |
| nicotinic acid | 0 | 0 | 640 | 270 | −3 |
| Molecular weight (kilodaltons) | n.d. | 110 | 93 | 42 | 100 |

Data from Fujita et al., 1952a; Murata, 1965; McCleary and Chick, 1977.
B.t., *Bacillus thiaminolyticus*;
B.a., *B. aneurinolyticus*;
n.d., not determined.

Clearly there are some marked differences among these thiaminases, in addition to the obvious differences between thiaminases I and II. As mentioned, the thiaminase I enzymes of two bacteria, *B. thiaminolyticus* and *C. sporogenes*, appear to be quite different. However, only the enzyme of *B. thiaminolyticus* has been sequenced.

We have purified the *Naegleria* death agent, monitoring its activity in inducing apoptosis of rat glioma C6 cells during purification. The apoptosis-inducing activity co-purifies with thiaminase. Most of the thiaminase activity has a molecular weight of about 41 kDa, but it is possible this is an enzymatically active cleavage product of a larger native enzyme. The ≈41 kDa enzyme is active as a base-substitution-dependent thiaminase, i.e., a thiaminase I, in a spectrophotometric assay (after Costell, et al., 1996). The enzyme activity also can be reconstituted after SDS-polyacrylamide gel electrophoresis, and visualized in a colorimetric gel assay (after Abe et al., 1987).

There have been reports of two thiaminases in some fish and clams, based on the occurrence of two pH optima in crude extracts (Reddy et al., 1948; Deolalkar and Sohonie, 1954; Fujita, 1954). However, in these experiments the extracts included the gastrointestinal tract of the animals, and a reasonable possibility is that the extracts-contained a mixture of an animal and a bacterial thiaminase.

D. Antithiamins other than Thiaminases

Low molecular weight anti-thiamin substances of an apparently nonenzymatic nature have been reported in plant materials, including tea (Vimokesant et al., 1974).

In addition, various thiamin-binding proteins have been reported in bacteria, yeast, plants, and hen's eggs (Friedrich, 1988). Most of these bind one molecule of thiamin per molecule of protein; some appear to be quite specific to thiamin. Some of these proteins appear to be involved in the uptake of thiamin by cells.

Several synthetic analogues of thiamin have been prepared that interfere with the utilization of thiamin. Such antimetabolites include pyrithiamin, an analogue of thiamin in which a pyridine has been substituted for the thiazole portion of thiamin. Pyrithiamin produces symptoms of thiamin deficiency in animals as well as in humans (Friedrich, 1988). In mice, pyrithiamin produces symptoms more severe than chronic thiamin deficiency (Woolley and White, 1943). Pyrithiamin has been shown to block the conversion of thiamin to TPP (Woolley, 1951a; Rogers, 1970). Oxythiamin and hydroxythiamin (substituted at C4 of the pyrimidine moiety) cause thiamin deficiency, but higher doses are required than with pyrithiamin and the apparent mode of action and effects on animals are different. (Steyn-Parvé, 1967). For example, oxythiamin and hydroxythiamin do not pass the blood-brain barrier; (e.g., Ostrovsky, 1965), whereas pyrithiamin does. Another analogue, amprolium, inhibits thiamin transport (Rogers, 1982). Many other analogues of thiamin have been prepared, and still others can readily be prepared. For example, thiamin, oxythiamin, and hydroxythiamin have been coupled to monocarboxylcellulose, and these derivatives remain effective as replacements for the vitamin and its antimetabolites (Ostrovsky et al, 1987; Zimatskina et al., 1996). This result indicates that targeting ligands can also be coupled to thiamin antimetabolites for use in creating localized thiamin deficiencies in the present invention.

III. Thiamin Depletion and Apoptosis

A. Thiamin deprivation induces apoptosis

Figure 2:
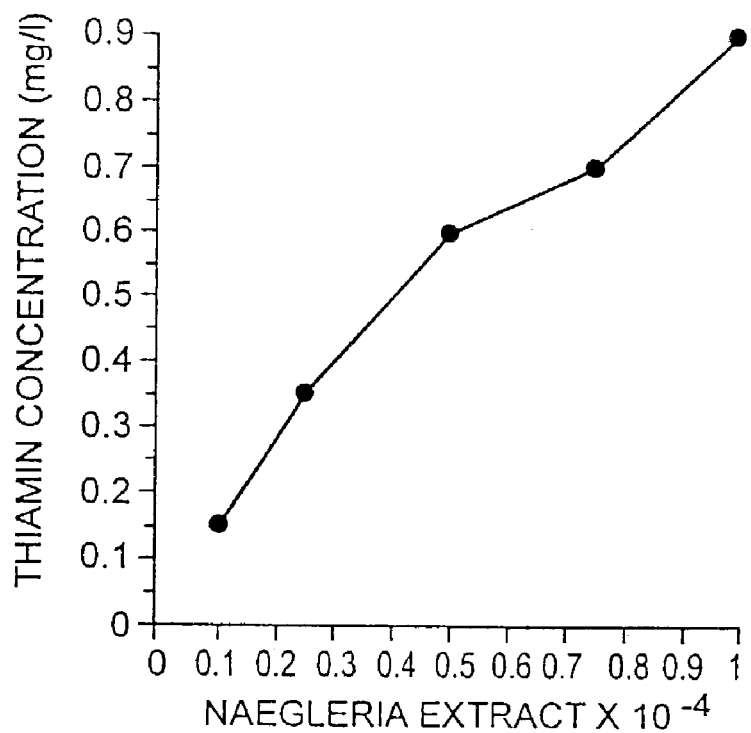
FIG. 2 is a graph showing the results of an experiment demonstrating that the amount of *Naegleria* agent (a thiaminase I) required to induce apoptosis was proportional to the concentration of thiamin in the medium. As the thiamin concentration was increased from 0.15 to 0.9 mg per liter, the amount of the *Naegleria* agent required to induce apoptosis increased from $10^{-5}$ to $10^{-4}$.

Our work has shown that the *Naegleria* agent that induces delayed apoptosis is a thiaminase, and that it induces apoptosis by depleting thiamin in the culture medium. This is shown by the following:

a) The ability of the *Naegleria* agent to induce apoptosis in cultured vertebrate cells is inversely proportional to the amount of thiamin in the culture medium. For example, the *Naegleria* agent at low concentrations readily induces apoptosis in medium 199 but not in medium RPMI 1640. Of the many differences between the two media, the crucial difference was traced to the level of thiamin: medium 199 contains 0.01 mg thiamin per liter while RPMI 1640 contains 1 mg thiamin per liter. Increasing the thiamin in Medium 199 was sufficient to abolish the ability of dilute *Naegleria* agent to induce apoptosis in that medium, and decreasing the thiamin in medium RPMI 1640 made the medium suitable for induction of apoptosis. In detailed experiments, the amount of *Naegleria* agent required to induce apoptosis was proportional to the concentration of thiamin in the medium. FIG. 2 shows an example of such an experiment. As the thiamin concentration was increased from 0.15 to 0.9 mg per liter, the amount of the *Naegleria* agent required to induce apoptosis increased from $10^{-5}$ to $10^{-4}$.

Figure 3:
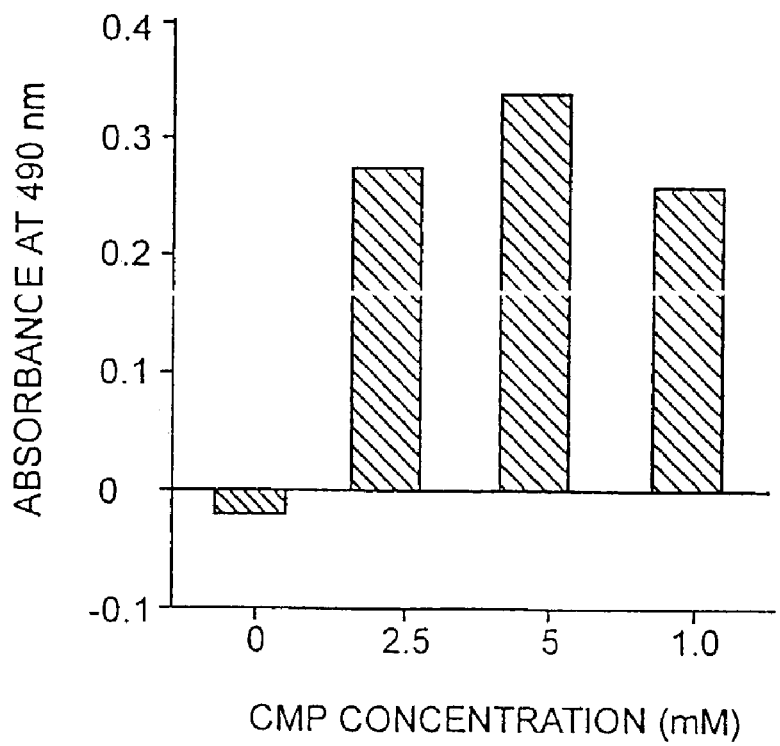
FIG. 3 is a bar graph depicting the results of an experiment to determine the effects of treatment of *Naegleria* agent with the specific thiaminase I inhibitor, 4-amino-6-chloro-2-methylpyrimidine (CMP). CMP is an effective inhibitor of thiaminase I that appears to act as an active-site directed, irreversible inhibitor. The graph shows that agent pretreated with CMP is unable to induce apoptosis, as illustrated by the determination of culture absorbance at 490 nm on day 6, after performing a colorimetric MTT assay for live vs. dead cells. Control cells have died but treatment of the *Naegleria* agent with 2.5-10 mM CMP prevented the induction of apoptosis.

Simple omission of thiamin from the culture medium does not induce apoptosis under our conditions, presumably because ample thiamin is provided by the 10% fetal calf serum and other components of the medium.

b) a relationship between the *Naegleria* agent, depletion of thiamin in the medium, and apoptosis is indicated by the following sample experiment. Medium 199 was prepared with a high concentration of thiamin, 60 mg per liter. This medium was incubated overnight at 37° C., either without any addition (control) or with the addition of an excess of *Naegleria* agent. At the end of incubation, the media were heated for 2 min at 100° C. (which destroys the ability of the *Naegleria* agent to induce apoptosis). The treated media were diluted with medium 199, to give expected thiamin concentrations from 0.5 to 2.0 mg per liter, and used to grow rat glioma C6 cells in the presence of freshly added *Naegleria* agent at a dilution of $10^{-5}$. As expected, all of the dilutions of the control medium, with excess thiamin at 0.5-2 mg per liter, prevented the induction of apoptosis by freshly added agent. In contrast, each dilution of the medium incubated overnight with *Naegleria* agent permitted induction of apoptosis by the *Naegleria* agent. The excess thiamin that prevented apoptosis had been destroyed by the *Naegleria* agent. The only straightforward explanation of such results is that during preincubation the *Naegleria* agent depleted the thiamin in the medium, and this depletion of thiamin permitted apoptosis.

c) In cultures nearing the end of the latent period in response to the *Naegleria* agent, within 12-24 hours of death, addition of excess thiamin reverses the process, and prevents apoptosis.

d) Partially purified *Naegleria* agent contains thiaminase I activity, and as the agent is purified the thiaminase activity is correlated with the ability of the agent to induce apoptosis. Proof that the *Naegleria* thiaminase I is the active agent, and the only one, in the *Naegleria* extract can be provided by cloning the *Naegleria* thiaminase gene, expressing it in bacteria, and showing that the expressed thiaminase induces delayed apoptosis as does the agent. These experiments are in progress. However, two other experiments provide unequivocal evidence that the agent is thiaminase.

e) A specific inhibitor of thiaminase I blocks the induction of apoptosis by the *Naegleria* agent. 4-Amino-6-chloro-2-methylpyrimidine (CMP) is an effective inhibitor of thiaminase I that appears to act as an active-site directed, irreversible inhibitor (Hutter and Slama, 1987). To avoid the toxicity of CMP to vertebrate cells, we pretreated the *Naegleria* agent with CMP. *Naegleria* extract was incubated with CMP, then diluted so its ability to induce apoptosis was tested with the remaining CMP at a low concentration. The control consisted of *Naegleria* extract incubated with the highest concentration of N,N-dimethylformamide, the solvent used to dissolve CMP. In the experiment shown in FIG. 3, the extract was incubated with CMP at concentrations of 2.5, 5, and 10 mM for 16 h at 25° C., diluted to a final extract concentration of $10^{-5}$, and assayed on rat glioma C6 cells. The control cells died at 4.75 days, as is usual for cells treated with the *Naegleria* agent. In contrast, the *Naegleria* agent treated with CMP at any concentration did not induce apoptosis; the cells were still healthy more than a week after the control cells died. The extent of apoptosis can be quantitated using a Promega Cell Titer AQueous Assay kit, where increased absorbance measures an increase in the proportion of living cells (that have mitochondrial dehydrogenase activity). FIG. 3 shows the results of an assay on day 6, showing that the control cells have died but that treatment of the *Naegleria* agent with 2.5-10 mM CMP prevented the induction of apoptosis. This active-site-directed inhibitor of thiaminase I inactivates the ability of the *Naegleria* agent to induce apoptosis.

f) If thiaminase I is the active agent, thiaminase from another organism should substitute to induce apoptosis. A culture of *E. coli* containing an expression plasmid which expresses the thiaminase I of *B. thiaminolyticus* was obtained (Costello et al., 1996). Extracts of the culture induced apoptosis in cultured vertebrate cells after they reach stationary phase, with the same latent period, the same dependency on growth arrest, and the same morphological pattern of apoptosis as induced by the *Naegleria* agent. Extracts of *E. coli* containing the same plasmid without the thiaminase gene did not induce apoptosis. In one experiment, for example, C6 cells treated with the *Naegleria* agent died after a latent period of 5.5 days, those treated with extracts containing bacterial thiaminase I died after 5.5 days, while cells that received no extract or the extract of plasmid-only bacteria did not die until day 16, when they died of starvation. As the *B. thiaminolyticus* thiaminase was purified, the apoptosis-inducing activity followed the enzyme activity.

Similar experiments have shown that partially purified thiaminase I of bracken (*Pteridium aquilinum*) has the same apoptosis-inducing activity as does the thiaminase I of *Naegleria*, and that the apoptosis-inducing activity of bracken purifies with the thiamin-cleaving activity.

Thus the induction of apoptosis by the *Naegleria* agent depends on active thiaminase, which can be replaced by the thiaminase of another organism, and which acts by reducing the amount of thiamin in the culture medium. It is not the thiaminase per se that induces apoptosis, but rather the thiamin deficiency caused by the action of the enzyme.

As thiaminase acts to induce apoptosis by producing a thiamin deficiency, thiamin antimetabolites are expected to also produce the same effect. Two thiamin analogues have been tested in vitro using rat glioma C6 cells. These two antimetabolites do not interfere with growth, but do induce apoptosis after the same latent period required for induction by the *Naegleria* agent (thiaminase). Amprolium, which inhibits thiamin uptake, is active at ≧0.6 mM, while pyrithiamin, which prevents conversion of thiamin to the active coenzyme thiamin diphosphate, is active at ≧10 μM. The similar time to apoptosis by thiaminase, amprolium, and pyrithiamin supports the conclusion that the latent period is the time required for the cells to use up their intracellular store of thiamin.

These experiments show that an appropriately targeted deficiency in vitamin $B_1$ becomes an effective means to induce apoptosis, and that this means has different properties, and offers different opportunities, than other apoptosis-inducing agents currently in use.

B. Creation of Thiamin Deficiency

The approach utilized in this invention is to induce apoptosis in selected target cells in vivo by creating a thiamin deficiency in these cells. This method utilizes a) a method of reducing the level of thiamin supplied to these cells and b) a method of targeting the cells. Various methods for accomplishing these steps can be utilized. Examples of these are described below.

1. Definition of Localized Thiamin Deficiency.

The term "localized thiamin deficiency" is used to mean the production of a thiamin deficiency in vivo that is localized in one or more or all of the following ways:

a) localized to a particular tissue or organ, i.e., in one part of the body, or b) localized to a particular cell type or tissue type, wherever they may be located in the body (e.g., metastases), or c) localized to more than one but a subset of all cell types, tissues or organs. Examples would be localization in more than one tissue (e.g., spleen and lymph) or in more than one cell type (e.g., androgen-dependent and androgen-independent prostate cancer cells).

Localization in this sense allows the induction of a thiamin deficiency in a selected subset of parts of a multicellular organism.

2. Methods of Inducing Thiamin Deficiency

The following are examples of methods for inducing thiamin deficiency:

a) by the provision of a diet deficient in the vitamin, b) by the introduction of intestinal flora that produce thiaminase, or c) by the introduction of a compound or compounds that i) acts as a competitive or noncompetitive antimetabolite of thiamin ii) sequesters thiamin, or iii) destroys thiamin. An example of an agent that would destroy thiamin is a thiaminase, but other compounds exist and still others can be designed and synthesized or identified that would render thiamin inactive by cleaving it or by other bio-molecular reaction.

As is known, method a) would produce a generalized thiamin deficiency which, if uncontrolled, would lead to beriberi in humans and similar diseases in other animals. Reduction of thiamin in the diet, while treating localized cell groups to produce thiamin deficiency, can be useful to amplify the effectiveness of the selective anti-thiamin treatment. Such general subclinical thiamin deficiency could be closely monitored by the medical team that stands ready to apply thiamin replacement as necessary. Thiamin deficiency can be monitored by several methods, including measurement of the thiamin in blood and in urine; the thiamin secreted in urine usually reaches zero as a deficiency begins. A reliable method is by measurement of the stimulation of erythrocyte transketolase by added TPP (the "TPP effect"). As thiamin and TPP become deficient, stimulation by added TPP increases; a stimulation of ≧15% indicates a thiamin deficiency (Wilson, 1991).

3. Thiaminases

As described above, thiaminases are readily available from several quite different organisms, from bacteria to ferns, from a protozoan to some fish. Such thiaminases can be used as thiamin-depleting agents in this invention. Although most of these have not yet been extensively purified or characterized, and only one has been sequenced (Costello et al., 1996), the diversity provides a variety of options for designing ideal therapeutic combinations.

We are working to clone and sequence selected thiaminase genes, and to express the thiaminases of *Naegleria gruberi* strain NEG, of bracken, and of carp in prokaryotes and in eukaryotes. Our work with partially purified *Naegleria* death-inducing agent (thiaminase) indicates that the agent retains ≧50% of its biological activity after one week incubation in cell culture medium at 37° C. The agent remains active after more than 12 months of storage at −20° C., including repeated cycles of freezing and thawing. Examples of the stability of other thiaminases, especially that of bracken, have been described above, and their stabilities indicate suitability for application as therapeutic drugs. In addition, a molluscan thiaminase I injected into mice and rats was detected 3-6 hours after parenteral administration, and even after 4 days if injected subcutaneously (Puzach, 1991; Puzach 1995). Such injected thiaminase caused specific symptoms of thiamin deficiency, but showed no intrinsic toxicity when administered parenterally for a week (Puzach and Ostrovsky, 1976; Ostrovsky et al., 1988).

a. Isolation or Purification of Thiaminases

Thiaminases can be purified using the methods used by previous workers, as well as more current methods (Deutscher, 1990; Menge, 1994; Costello et al., 1996). Purification can be monitored by assays of thiaminase activity, as well as evaluations of protein purity by gel electrophoresis; at some stages these procedures can be combined (Abe et al., 1987). Picomole quantities of peptides from the pure protein will be N-terminal sequenced (Matsudaira, 1990).

b. Isolation of Nucleic Acid Sequences Encoding Thiaminases

As indicated above, a variety of different organisms are known to produce thiaminases; these thiaminases can be used in the present invention. It is advantageous to have isolated, purified, or enriched nucleic acid sequences encoding such thiaminases. Such nucleic acid sequences can be obtained using routine techniques known to those skilled in the art.

In one approach, using procedures known to those skilled in the art, the amino acid sequence can be used to design primers, and these will be used in conjunction with the polymerase chain reaction to identify the corresponding thiaminase gene (genomic or cDNA sequences) (Mullis et al., 1994). Preferably, amino acid sequences are used which correspond to unique or low degeneracy primer sequences. Genes will be cloned, sequenced, and expressed using standard techniques (Sambrook et al., 1989). Clones expressing thiaminase can be detected on plates using a color method (Abe et al., 1986) or radioactivity (Edwin, 1979).

Another approach can be used to identify and obtain thiaminase genes which have significant homology to the *Bacillus thiaminolyticus* thiaminase gene. Primers are designed based on the known sequence of the *B. thiaminolyticus* thiaminase gene, and used to PCR amplify a portion of a homologous gene from another organism. Preferably primer sequences are selected from regions expected to be conserved between species. An example would be sequences around the active site of the enzyme. Those skilled in the art understand the sequence and primer length considerations for utilizing this approach. The amplified sequence can be used to identify cDNA or genomic DNA clones which contain the sequence. The inserts in such clones can be expressed using standard expression systems, and thiaminase activity assayed.

Thiaminase I activity can be assayed at 25° C. using secondary nucleophiles and measuring the absorbance change at 252 nm which result from the reaction of thiamin with the secondary nucleophile (Lienhard, 1970; Costello et al., 1996). For both thiaminase I and II, one can also measure the amount of thiamin that remains using the thiochrome method (see Wyatt et al., 1989), or measure the degradation directly using thiamin that is radioactively labeled in the thiazole ring (Evans, 1975; Edwin, 1979; Alston and Abeles, 1987).

c. Advantageous Characteristics of Thiaminases

In comparison with other antithiamins, thiaminases offer certain advantageous characteristics:

i) They offer the amplifying action of catalysis, such that one thiaminase molecule can destroy many thiamin molecules. For example, the *Bacillus thiaminolyticus* thiaminase I has a $k_{cat}$ of 34 s$^{-1}$ (Costello et al, 1996). In contrast, for example, most thiamin-binding protein molecules would bind one molecule of thiamin and it has been estimated that about 40 molecules of pyrithiamin are required to nullify one molecule of thiamin—a ratio that was considered efficient for an antimetabolite (Woolley and White, 1943).

ii) Thiaminase has the potential to cause thiamin deficiency by acting externally to any cell or group of cells the enzyme can "surround," and iii) Thiaminases offer opportunities to utilize the protein nature of the enzyme or its derivatives for localization.

Because of these characteristics, the examples use thiaminases to illustrate the invention, but this invention should not be considered limited with respect to the method used to induce a localized thiamin deficiency.

4. Mutagenesis of Thiaminase and Creation of Thiaminase Derivatives and Synthetic Thiaminases Naturally occurring thiaminases, in addition to direct use as thiamin-depleting agents, can also be used to provide the basis for constructing and/or designing other thiamin-cleaving compounds based on the sequence and/or structure of biologically active portions of the natural thiaminases. Such compounds thus include thiaminase derivatives and artificial or synthetic thiaminases.

Dissection of the thiaminase polypeptide to a smaller core or reduced size polypeptide containing enzyme activity and apoptosis-inducing activity can facilitate targeted delivery.

It is useful to define the segment of the thiaminase molecule that is necessary for enzymatic activity and death-inducing function (i.e., the core enzyme). Thiaminase, used as a drug, is less likely to be cleaved by proteases or to be immunogenic if it is trimmed to minimal, or at least smaller size. It may also be easier to target. This dissection and trimming can be achieved, for example, by targeted mutagenesis of the thiaminase gene of interest, expressed in bacteria, using standard procedures (Sambrook et al., 1989) to identify the segments that are essential for thiaminase activity and for apoptosis induction. The ability to trim thiaminase while retaining activity is supported by the observation that limited proteolytic cleavage of a molluscan thiaminase I does not decrease its activity (Ostrovsky et al., 1988).

In addition to dissecting the segment of a thiaminase that is required for biological activity, targeted mutagenesis will allow the production of thiaminase protein or segments thereof that are enzymatically inactive, which will be useful in drug development and testing, and or for inducing immunologic tolerance toward a corresponding active polypeptide thiaminase or thiaminase derivative.

While size reduction of the thiaminase molecule provides thiamin-cleaving compounds having certain advantages, chemical modification and/or insertion of non-natural amino acids can also be used to produce compounds which can be even more resistant to degradation or which have other advantageous properties for use in vivo.

The analysis of the active site can also be used to design artificial or synthetic thiaminases. In this respect it can be useful to utilize information from a number of different thiaminases from different organisms. Examples of some potential sources for thiaminases were described above. For most purposes, it will be preferable to analyze a set of functionally related thiaminases, for example, a set of either thiaminase I or thiaminase II enzymes. While many different thiaminases could be used, an exemplary set of thiaminase I enzymes could include those from a strain/species of the protozoan *Naegleria*, from a fish of the family Cyprinidae (carp and goldfish), and from a pteridophyte (e.g., the fern bracken).

Isolation of the thiaminases can be accomplished directly by routine methods of protein purification, or can be obtained by isolating and expressing nucleic acid sequences encoding the desired thiaminase or thiaminases, also by routine methods. For example, peptide sequences of at least part of a thiaminase can be obtained using small quantities of purified protein. These peptide sequences can be used to design oligonucleotide primers or probes, which are preferably either unique or of low degeneracy. These oligonucleotides can then be used, directly or using PCR amplification, to identify cDNA or genomic DNA clones containing complementary sequences. The sequences so identified can then be sequenced; if necessary, the inserts from two or more clones can be used to construct a complete coding region. The sequence obtained can be inserted into an expression vector and expressed. The activity of the product can be tested and confirmed. This process provides both the nucleic acid sequence and the isolated product for further analysis and manipulation.

Analysis of the geometry and critical amino acid residues of the active site will reveal the important structural features for thiamin-cleaving activity. These structural features can be incorporated into peptides or polypeptides having size and amino acid sequences selected to enhance or optimize properties such as stability and tumor penetration.

The analysis can also be used to design artificial thiaminases which are not solely composed of natural amino acids and which may be completely or partially non-peptide structures. This allows the incorporation of bonds and structures having appropriate rigidity while also providing an appropriate active site structure. This can allow the design of a molecule which is considerably smaller and/or more resistant to degradation than even reduced size thiaminase derivatives and which may have further advantageous properties. For example, in some cases such a molecule can be orally bioactive.

It is often advantageous to test a large number of different potentially active compounds. Therefore, in one approach, combinatorial synthesis is used to provide libraries of such peptidomimetic compounds designed based on the active site of one or more thiaminases. The library compounds can then be tested for activity against thiamin, as well as for the ability to induce apoptosis in vitro.

5. Inducing Tolerance

For the use of thiaminase protein for chemotherapy, it is desirable to avoid or minimize the production of anti-thiaminase antibodies that could neutralize or destroy the thiaminase. The extent to which this might be a problem depends on the immunogenicity of the polypeptide used as well as the method and place of delivery (e.g., intravenous or oral delivery favor tolerance (Schwartz, 1993)). It also depends on how long the thiaminase needs to be present to complete its task; for example, if apoptosis is induced in a tissue as rapidly as it is induced in vitro, the treatment may be complete before production of antibodies became a problem. If the production of anti-thiaminase antibodies becomes a problem, this immune reaction could be reduced or eliminated by various methods, such as by one or more of the following:

a) Since several thiaminases are available, one could simply change to a thiaminase with different antigens during therapy.

b) One could avoid an immune response overall by use of immunosuppressive drugs such as cyclosporin during the treatment. For the proposed treatment the immune system needs to be compromised only for a short period.

c) One could create tolerance in the treated individual by flooding the system with an excess of enzymatically inactive thiaminase (prepared by mutagenesis, as described above). Often oral provision of antigen is an efficient method of inducing tolerance (Weiner et al., 1994), but antigen given parenterally in high concentrations also induces tolerance (Dixon and Mauer, 1955).

6. Synthetic Thiaminase

Drugs capable of specifically recognizing and catalyzing the cleavage of thiamin can also be designed; such drugs would be small peptides or even nonpeptides, such as peptiomimetic compounds. Such "synthetic thiaminases" could then be coupled to other molecules, as described below, and targeted to selected cells. These synthetic thiaminases can be selected to avoid the immunogenicity and susceptibility to proteases which can be associated with protein thiaminases. It is also possible to produce small molecules that would go where proteins would not go as readily (e.g., into solid tumors).

The properties of thiamin indicate that it will be relatively straightforward to design such molecules. Thiamin is relatively stable (e.g., it can be autoclaved for 30 min at $pH \leqq 5$), yet the methylene bridge between the pyrimidine and thiazole rings is easily cleaved, either by $pH \geqq 9$ at room temperature or especially by a number of compounds, including sulfites (Friedrich, 1988). Sulfite ion will cleave thiamin quantitatively at pH 5 and room temperature into its two halves (Williams et al., 1935; Uray et al., 1993). The lability of the methylene bridge of thiamin to high pH or to sulfite suggests that a catalyst which would cleave this bridge would be easy to design; in addition the catalyst would be designed to have specificity to thiamin.

7. Thiamin-sequestering Compounds

Compounds that specifically sequester thiamin have been described above; the best known are proteins that bind thiamin in a 1:1 molar ratio. Such compounds, properly localized in the animal, could achieve the same result as true or synthetic thiaminases if present at a sufficient level.

8. Thiamin Antagonists

Thiamin antagonists, in order to be useful in inducing apoptosis by creating a localized thiamin deficiency, should a) be able to be localized and b) be able to enter target cells where they would affect thiamin metabolism. Either competitive or noncompetitive antimetabolites can be used. Such a compound could be a cleavable compound, one that, for example, might combine a targeting molecule in a cleavable compound with a thiamin analogue such as oxythiamin or pyrithiamin. Further, the ability to couple thiamin antimetabolites with targeting ligands is indicated by the retention of function of analogues coupled to cellulose (Ostrovsky et al., 1987; Zimatkina et al., 1996). Alternatively, the compound could be carried to target cells in a package, such as liposomes. Other delivery methods, as indicated below, can also be used as appropriate for the specific compound and the targeted cells.

9. Growth-arrest Dependent Apoptosis and Cancer Chemotherapy

In our in vitro experiments with cell cultures, mammalian cells have grown continuously, at normal rate and with normal morphology, in the presence of the *Naegleria* agent (thiaminase I) until they reached stationary phase or became growth arrested. We have also shown that thiaminase I can kill quiescent cells directly, i.e., if the agent is added to quiescent cells, the cells die after a latent period (e.g., 4 days) without ever resuming growth. On the other hand, the agent does not kill cells while they are actively growing. This growth-arrest dependent apoptosis raises three important points, here addressed specifically with respect to cancer therapy.

First, even if thiamin depletion induces apoptosis only in non-cycling cells, it would target a population of cells found in most cancers and in all solid tumors, a population which is especially abundant in some tumors such as advanced prostate cancer. These non-cycling cells present a problem for current therapies using radiation and chemicals, which are more damaging to actively growing cells. Thus even if thiamin-deficiency-induced apoptosis targets mainly or only non-cycling cells, this offers an important therapeutic application not presently available.

Second, in all but rare cases no single therapeutic treatment currently available is expected to eliminate all cancer cells, and multiple therapies are usually applied. The addition of thiamin-deficiency-induced apoptosis offers a powerful tool even if it preferentially attacks non-cycling cells, as combined conventional chemotherapy and radiation attack actively dividing cells.

Third, we do not yet know how thiamin deficiency induces apoptosis. Thiamin, via TPP, lies at the heart of the citric acid cycle and cellular energy production, and a true deficiency would be expected to profoundly affect growing cells. We suspect that so far in our in vitro culture conditions we have reached a true deficiency only after the cells have become growth arrested due to some other cause, such as becoming confluent. Conversely, it seem likely that cells, which in fact become thiamin deficient would, for this reason alone, cease to grow. Thus, the apparent dependence of induction of apoptosis by the *Naegleria* agent on growth arrest may simply indicate that thiamin-deficient cells cannot grow, and in fact undergo apoptotic death. In this sense, thiamin deficiency will induce death of growing cells as well, but they are likely to stop growing before they die.

Thus, a therapy focused on non-cycling cells offers unique opportunities, in conjunction with other therapies, and there is no reason to anticipate that the induction of apoptosis by thiamin depletion cannot be broadened to include actively growing cells as well.

10. An Example of a Specific Use of Thiaminase: Prostate Cancer

Before considering some of the possible methods of targeting thiaminase or other means of creating a localized thiamin deficiency, it is instructive to examine how targeted thiamin depletion might be used in cancer therapy. The selected example illustrates its use in prostate cancer; this illustrative example should not be considered to limit the invention.

Prostate cancer is responsible for 43% of new noncutaneous cancer cases in men, and has become the second leading cause of male cancer deaths (Parker et al., 1991; da Vita, 1997, pp. 1322-1386). The tumor cells in the adenocarcinomas are initially androgen dependent, and androgen ablation (e.g., castration) causes apoptosis of these cells. This causes initial remission of the prostate cancer, but any tumor cells left behind eventually change from androgen-dependent to androgen-independent (see Umekita et al., 1996). Thus after an initial remission as the androgen-dependent cells die, within a year or two the androgen-independent cancer cells become evident, grow, metastasize, and eventually kill the patient. The major problem in devising a therapy to kill these androgen-independent tumor cells has been that most of the cells are not actively proliferating at any particular time; it has been estimated that about 2% undergo division on any given day. As J. T. Isaacs and his coworkers put it, "Unfortunately, more than 90% of prostatic cancer cells within an individual patient are in interphase" (Kyprianou et al., 1991). These authors concluded that the only hope to improve survival rates for prostate cancer is simultaneous therapy of androgen ablation to kill the androgen-dependent cells and some therapy to eliminate the androgen-independent cells. One way to eliminate the androgen-independent cells is to increase the rate of apoptosis among non-proliferating cancer cells.

Prostate cancer provides an excellent situation for use of thiamin-depletion-induced apoptosis. The many cells lines in which the *Naegleria* agent (thiaminase I) was shown to induce apoptosis include two cell lines derived from human prostate cancers, LNCaP, which is an androgen-dependent cell line, and PC-3, which is an androgen-independent cell line that is null for the p53 gene, so prostate cancers are among good candidates for treatments using our invention. In order to induce apoptosis in these cancer cells, it would suffice to surround the cells, the tissues, or the tumors with thiaminase, and thereby starve the cells for thiamin.

For this therapy it is important to maintain the low level of thiaminase continuously around the cancer cells until the cells become depleted of the vitamin and undergo apoptosis. The therapy does not require that every cell be surrounded. Adequately surrounding a group of cells (e.g., a solid tumor) would be sufficient. A particularly useful approach would be to localize the thiaminase by lining the walls of the capillaries that feed the prostate cancer cell mass, thus destroying all thiamin brought to the tissue. The principle of this method is to surround the cancer cells and starve them of thiamin until they all undergo apoptosis. Properly applied, this therapeutic approach could avoid the widespread nonspecific tissue damage that accompanies use of poisons and radiation.

IV. Combination of Thiamin Depletion and Accessory Treatment for Targeted Cells.

In addition to the use of thiamin depletion to induce apoptosis of a targeted group of cells, a variety of different accessory treatments can be utilized in conjunction with the thiamin depletion to enhance the effectiveness of the treatment. Conversely, for some treatments, such as other antineoplastic treatments, the use of apoptosis induced by thiamin depletion can be regarded as enhancing the effectiveness of that other treatment. Thus, the present invention includes such combination therapy, where thiamin deficiency induced apoptosis is used in conjunction with another treatment method. In these combination methods, the thiamin depletion can be targeted by any of a variety of methods, for example, by any of the methods described herein. Also, the accessory methods also preferably involve localized or targeted treatment. Any of a variety of methods may be used for such targeting also, again for example, the targeting methods described for targeting of thiamin depletion, with the choice of targeting method being appropriate for the type of composition involved in the accessory treatment. Those skilled in the art will readily recognize the appropriate selections.

A. Thiamin Depletion in Conjunction with Conventional Antineoplastic Treatments

As indicated, one type of accessory treatment is the use of another antineoplastic treatment, for example, conventional anticancer treatments. These include, for example, radiation treatment and treatments with compounds which preferentially inhibit actively growing cells or which preferentially target neoplastic cells (e.g., cancer cells). Combining thiamin depletion with another antineoplastic treatment can provide additive effect, or preferably can provide a complementary effect, where one treatment is effective against a group of cells against which another treatment is less effective or even ineffective. For example, as indicated, many antineoplastic agents are effective against actively growing cells, but significantly less effective against quiescent cells. Therefore, administration of such an antineoplastic agent may kill a sub-population of actively growing cancer cells, but be ineffective against quiescent cancer cells, such as those in the interior of a solid tumor. Creation of a localized thiamin deficiency in those remaining cancer cells can then lead to apoptosis of the quiescent cells. In such a situation, both the administration of a treatment or agent which is preferentially effective against actively growing cells and the use of localized thiamin depletion can mutually enhance effectiveness against tumor cells.

In the context of the use of thiamin depletion and one or more accessory methods, the term "in conjunction" indicates that the use of the two or more methods is temporally related. However, the term does not require that the methods be used simultaneously, though such simultaneous use is utilized in preferred embodiments. Thus, one method can be utilized before another or the uses may overlap or the uses may be simultaneous. However, the term does indicate that the methods are used sufficiently close in time so that relevant physiological effects persist from the use of the first method at least until the use of an immediately following method. Such physiological effects include, for example, a reduction of the number of tumor cells, reduction of the level of activity of a relevant cellular protein, and reduction in the level of cellular thiamin.

B. Thiamin Depletion in Conjunction with Treatment Affecting Carbohydrate Metabolism In cultured cell lines in vitro, production of thiamin-deficiency, e.g., using thiaminase, induces apoptosis of the cells after a latent period during which the cells proliferate normally and reach stationary phase in which most of the cells become quiescent before they die.

Treatments that alter carbohydrate metabolism can affect this latent period as well as the rapidity at which the cell population subsequently dies. For example, if cells of the rat glioma C6 cell line are grown in medium containing glucose at 1 g/liter and thiamin-deficiency is induced with thiaminase added at day 0, the cells grow normally and begin to die on day 4. If the glucose is increased up to 2 to 5 g/liter ("hyperglycemia"), the latent period is extended by a day or more, e.g., in one experiment from 4 days to 7 days. Yet when apoptosis does occur the cell population in the hyperglycemic condition dies more rapidly and synchronously than the cell population grown with less glucose. In several experiments, the presence of excess glucose resulted in the death of clonogenic surviving cells such that within 3 to 6 days after morphological death began, there were only 0 to 6 clonogenic survivors per $10^7$ original stationary phase cells. This is an extraordinarily effective killing compared to that achieved by therapeutically allowable doses of most chemotherapeutic drugs. Once cell death began, the killing of the cell population was even more rapid and complete than has been obtained in low-glucose media, although in this case too, there were <10 survivors per $10^7$ original stationary phase cells.

Without being limited by the following description of the possible mechanism for carbohydrate enhancement of thiamin deficiency induced apoptosis, it is believed that the excess glucose increases the extent to which the cells derive their energy from glycolysis vs. respiration, increasing the sensitivity to thiamin depletion.

The enhancement of thiamin deficiency induced apoptosis by high carbohydrate levels (e.g., high glucose levels) is also consistent with early reports on the development of beriberi in rats. For example, a classic biochemistry textbook (Fruton and Simmonds, 1958, p.983) noted that "[t]he close relation between thiamine and carbohydrate metabolism is indicated further by the observation that rats are able to survive many months without dietary thiamine if their diet contains no carbohydrate. The addition of glucose to the diet of such thiamine-deficient rats leads to loss of weight, polyneuritis, and death."

Such glucose or other carbohydrate elevation can be accomplished by simple means known to those practiced in the art, for example, by simple glucose intravenous administration.

In addition to manipulation of carbohydrate levels, e.g., glucose levels, to alter the course of thiamin-induced apoptosis, other nutritional factors can be manipulated to beneficially affect the apoptotic process. An example of such other nutritional factor is iron. Depletion of iron is believed to lead to apoptosis. Thus, combination of iron depletion with thiamin depletion, with one or both of the depletions being localized to target cells will provide enhancement of the apoptotic effect for killing the target cells. The enhancement may be an increase in cell-killing efficiency and/or a change in the time course of apoptosis.

C. Combined Use of Antiangiogenesis or Antivascular Therapy and Thiamin Depletion It has been shown that the growth of solid tumors beyond about 2 mm depends on vascularization (Folkman, 1997). Recent studies have shown that inhibitors of this angiogenesis can result in tumors becoming quiescent (Boehm et al., 1997: O'Reilly et al., 1996; Skobe et al., 1997). As described above, thiamin deficiency induced apoptosis kills quiescent cells. Thus, inducing quiescence of cells in a solid tumor would markedly enhance the therapeutic effectiveness of inducing a targeted thiamin deficiency in that tumor by increasing the fraction of quiescent cells.

A variety of different agents may be used for antiangiogenesis therapy. Examples of antiangiogenesis agents (e.g., angiogenesis inhibitors) include angiostatin (O'Reilly et al., 1996; Sim et al., 1997) and endostatin (Boehm et al., 1997), which may be used in combination. Other compounds can target other angiogenesis-related targets and processes, for example, vascular endothelial growth factor (VEGF) or enzymes required for angiogenesis, including enzymes involved in extracellular matrix modification. Usually, the compound will be selected to inhibit the function of the angiogenesis-related biomolecule.

In connection with the inhibition of angiogenesis-related biomolecules, such inhibition may be achieved in a variety of ways. For example, the activity of proteins may be inhibited with small molecule inhibitors, or expression of proteins or RNA molecules may be inhibited. As recognized by those skilled in the art, inhibition of expression can also be obtained using any of a variety of different methods. In particular, in addition to small molecule inhibitors, expression can be inhibited using ribozymes or other catalytic nucleic acid molecules or antisense or triple helix approaches. The use of such inhibitors is briefly described in a following section.

A list of selected angiogenesis inhibitors other than angiostatin and endostatin which have been evaluated at least to some extent and references describing each compound follows, divided into broad categories:

Extracellular proteins and protein fragments

Matrix matalloproteinase (MMP) inhibitors (Rasmussen and McCann, 1997, review). This is a group of approximately 15 proteases involved in tissue remodeling by degeneration of the extracellular matrix, and they are needed for tumor growth and tumor cell invasion and metastasis.

| | |
|---|---|
| AG3340 | Santos et al., 1997 |
| Batimastat | Parsons et al., 1997 |
| Marimastat (BB2516) | Denis & Verweij, 1997; Rasmussen & McCann, 1997 |

-continued

| | |
|---|---|
| GM6001 (N-[2R-2-(hydroxamido-carbonymethyl)-4-methylpentanoyl)]-L-tryptophan methylamide) | Galardy et al., 1994 |
| PEX | Brooks et al., 1998. A proteolytic fragment of MMP-2 also found in vivo; binds to integrin and disrupts angioigenesis. |
| Antibodies to angiogenic agents | |
| anti-VEGF | Borgstrom et al., 1998; Borgstrom et al., 1996; Presta et al., 1997 (humanized antibody). |
| anti-angiogenin | Piccoli et al., 1998 (including humanized antibodies). |
| anti-bFGF | Pluda, 1997 (antibody to basic fibroblast growth factor) |
| anti-integrin $\alpha_v\beta_3$ | Brooks et al., 1994 (disrupts angiogenesis by blocking this integrin, leading to regression of tumors). |
| Pentosan polysulfate | Pluda, 1997 (sulfated polysaccharide xylanopolyhydrogensulfate, inhibits bFGF-induced angiogenesis. If toxicity is too great for human use, less toxic derivatives may be more useful alternatives.) |
| TNP-470 (AGM-1470) | Berensen et al., 1998; Kudelka et al., 1998 (synthetic derivative of the antibiotic fumagillin which inhibits the growth of blood vessels by unknown mechanism). |
| FR-118487 | Eda et al., 1998 (a synthetic derivative of another antibiotic). |
| PF4 (platelet factor-4) | Pluda, 1997; Brooks et al., 1998 (mechanism uncertain; believed to block binding of bFGF to its receptor). |
| Linomide | Ziche et al., 1998; Hartley-Asp et al., 1997 (synthetic compound which blocks VEGF-dependent angiogenesis). |
| Metastat | Glinsky et al., 1996 (compound competes for specific carbohydrate-lectin interactions). |
| Tecogalin (DS4152, SP-PG) | Eckhardt et al., 1996 (derived from a bacterially produced sulfated polysaccharide, inhibits bFGF receptors). |
| Thrombospondin-1(TSP-1) | Campbell et al., 1998 (a natural protein of uncetain mechanism of action; may interact with integrin $\alpha_v\beta_3$). |
| Angiopoietin-2 | Maisonpierre et al., 1997 (a natural antagonist in the angiopoietin family inhibiting Tie2 receptor tyrosine kinase). |
| Thalidomide | Gutman et al., 1996; Minchinton et al., 1996 (may block angiogenesis by antagonizing bFGF; subject to well-known limitations on use). |
| Interleukin-12 (IL-12) | Pluda, 1997 |
| CT2584 | Marucci et al., 1997 |
| Carboxyamidotriazole (CAI) | A $Ca^{2+}$ channel blocker, suppresses proliferation of endothelial cells. |

Angiogenesis inhibitors—mechanisms varied or unknown
Nitrous oxide blocking agents—may be useful as such agents have anti-angiogenic properties.

The angiogenesis inhibitors listed above, as well as active derivatives and analogs of those compounds, provide examples of compounds which may be useful in conjunction with thiamin deficiency induced apoptosis in targeting a group or groups of neoplastic cells (preferably cancer cells) for cell death. Of course, such accessory treatment is not limited to the use of these compounds, but can utilize any of a variety of different compounds which inhibit angiogenesis or other process involved in the development of tumors.

A number of the compounds listed above have been tested in various clinical or preclinical trials. Included are trials involving gene therapy using DNA sequences encoding oligo- or polypeptide angiogenesis inhibitors, demonstrating that gene therapy is an appropriate administration method for peptidic compounds in accessory treatment methods for this invention. Examples include a trial with angiostatin cDNA (Yoneda et al., 1998) and a thrombospondin-1 DNA trial (Cao et al., 1998).

In addition to gene therapy involving angiogenesis inhibitors, the expression or level of activity of a number of different genes involved in angiogenesis can be modulated. A variety of such genes have been identified, for example, in Yoneda et al., 1998. Thus, expression of genes which promote angiogenesis may be inhibited, for example, using ribozymes or other catalytic nucleic acid molecules or antisense molecules against the mRNA encoding a relevant polypeptide. Also, the activity of particular gene products may be inhibited in the usual manner using small molecule inhibitors, which may, for example, be identified by screening assays in a conventional manner.

While not strictly an antiangiogenesis method, other methods can be used as accessory treatments which reduce the maintenance of a tumor. Thus, for example, in a method directed to the neovasculature of a tumor, CM101 (GBS toxin) induces inflammation in tumor neovasculature (Pluda, 1967; Wamil et al., 1997). Another example of an antivascular treatment is the induction of blood clots (infarcts) in tumor blood vessels, which can cause regression of tumors in mice (Huang et al., 1997). Such inflammation or blockage is expected to decrease provision of nutrients to the tumor cells, thereby reducing the ability of the tumors to expand and even killing at least some of the tumor cells. As with antiangiogenesis treatments, this approach is useful as an accessory treatment in the present invention. Other such treatments directed against tumor growth or maintenance are also within the scope of the present invention.

Antiangiogenesis therapy appears to work by disrupting the tumor microvasculature that provides nutrients, including oxygen, to a tumor and takes away waste. In that sense, antiangiogenesis therapy produces overall "starvation" of the tumor. Some cells die, apparently both by necrosis and by apoptosis, while others simply become dormant (quiescent). Overall starvation, depending on the exact (and locally variable) conditions, induces death of some cells and quiescence in others. In contrast, specific starvation for thiamin induces apoptotic death, even in quiescent cells. Thus, these paradigms differ, and are, in fact, complementary. Used together, for example, antiangiogenesis therapy can arrest cell growth and LAIDT therapy can kill the arrested cells.

D. Thiamin Depletion in Conjunction with Modulation of the Level of Activity of Apoptosis-related Proteins The effectiveness of thiamin induced apoptosis can also be enhanced by altering the level of activity of one or more apoptosis related proteins. It has been found that a variety of different intracellular and secreted proteins were involved in the induction of apoptosis for a number of different apoptosis inducing agents or conditions. It has further been found that some of those proteins are apoptosis enhancing and others are apoptosis suppressing proteins. As a result, inhibition of the activity of an apoptosis suppressing protein or proteins and/or elevation of the activity of one or more apoptosis enhancing proteins will have effects on the induction and rate and completeness of cell death in targeted cells.

For example, a family of secreted apoptosis-related proteins (SARPs) have been found which are produced by cells and which modify the sensitivity of signaling pathways (Melkonyan et al., 1997). Some of these SARPs increase the sensitivity of cells to signals that induce apoptosis, while others suppress such sensitivity. Thus, as indicated above, the activity of such SARPs can be modulated to enhance the effectiveness or increase the rapidity of thiamin deficiency induced apoptosis.

In preferred embodiments, the accessory method involves inhibition of the activity of an apoptosis inhibiting secreted apoptosis related protein. As is generally understood, the level of activity of a protein can be inhibited in a variety of different ways. Examples include inhibition of expression, such as by targeting, transcription or translation, as well as direct inhibition of the protein product. Thus, in preferred embodiments the method involves inhibiting the expression of an apoptosis related protein. Such inhibition of expression can be accomplished by a variety of methods known in the art, for example, through the use of antisense or triple-helix forming oligonucleotides, or ribozymes or other catalytic nucleic acid molecules.

1. Complementary Oligonucleotides and Ribozymes

As indicated in the Summary above, in cases where it is advantageous to inhibit the expression of a gene product such as a polypeptide, nucleotide-based inhibitors can be used. Such inhibitors can function, for example, by antisense, triple helix, or catalytic mechanisms. Thus, such inhibitors include, for example, antisense oligonucleotides and ribozymes and other catalytic nucleic acid molecules including analogs and derivatives.

While such molecules are described here in connection with the inhibition of apoptosis-related proteins as an accessory method to localized thiamin depletion, it is clear that this approach is also useful for inhibition of other gene products. Such other gene products include a number of angiogenesis-promoting molecules. Thus, in further examples, such inhibitor molecules can also be used as antiangiogenesis agents.

Thus, oligonucleotides or oligonucleotide analogs which interact with complementary sequences of cellular target DNA or RNA can be synthesized and used to inhibit or control gene expression at the levels of transcription or translation. The oligonucleotides of this invention can be either oligodeoxyribonucleotides or oligoribonucleotides, or derivatives thereof, which are complementary to target nucleic acid sequences or they can act enzymatically, such as ribozymes. Both antisense RNA and DNA can be used in this capacity as chemotherapeutic agents for inhibiting gene transcription or translation, as in Trojan, J., et al., "Treatment and prevention of rat glioblastoma by immunogenic C6 cells expressing antisense insulin-like growth factor I RNA," *Science* 259:94-97 (1993). Inhibitory complementary oligonucleotides may be used as inhibitors for cancer therapeutics because of their high specificity and lack of toxicity.

Included in the scope of the invention are oligoribonucleotides, including antisense RNA and DNA molecules and ribozymes and other catalytic nucleic acid molecules that function to inhibit expression of a gene in an accessory treatment to creation of a thiamin deficiency. Anti-sense RNA and DNA molecules act to directly block the translation of mRNA by binding to targeted mRNA and preventing protein translation or directing RNase mediated degradation of the mRNA. With respect to antisense DNA, oligodeoxyribonucleotides derived from the translation initiation site, e.g., between −10 and +10 regions of the relevant nucleotide sequence, are preferred.

Ribozymes are enzymatic RNA molecules capable of catalyzing the specific cleavage of RNA. The mechanism of ribozyme action involves sequence specific interaction of the ribozyme molecule to complementary target RNA, followed by a endonucleolytic cleavage. Within the scope of the invention are engineered hammerhead, hairpin, and other motif ribozyme molecules that catalyze sequence specific endonucleolytic cleavage of RNA sequences encoding a gene product essential for cell survival, growth, or vitality.

Specific ribozyme cleavage sites within any potential RNA target can initially be identified by scanning the target molecule for ribozyme cleavage sites, such as sites which include the following sequences, GUA, GUU and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate targets may also be evaluated by testing their accessibility to hybridization with complementary oligonucleotides, using ribonuclease protection assays. See, for example, Draper PCT WO 93/23569. For the present invention, the target site will generally include a sequence variance site as described above.

Both anti-sense RNA and DNA molecules and ribozymes of the invention may be prepared by any method known in the art for the synthesis of RNA and DNA molecules. See, for example, Draper, supra. hereby incorporated by reference herein. These include techniques for chemically synthesizing oligodeoxyribonucleotides well known in the art such as, for example, solid phase phosphoramidite chemical synthesis. Alternatively, RNA molecules may be generated by in vitro and in vivo transcription of DNA sequences encoding the antisense or ribozyme RNA molecule. Such DNA sequences may be incorporated into a wide variety of vectors which incorporate suitable RNA polymerase promoters such as the T7 or SP6 polymerase promoters. Alternatively, antisense or ribozyme cDNA constructs that synthesize antisense or ribozymes RNA constitutively or inducibly, depending on the promoter used, can be introduced stably into cell lines.

Various modifications to the DNA molecules may be introduced as a means of increasing intracellular stability and half-life. Possible modifications include but are not limited to the addition of flanking sequences of ribo- or deoxy-nucleotides to the 5' and/or 3' ends of the molecule or the use of phosphorothioate or methyl phosphonate rather than phosphodiesterase linkages within the oligodeoxyribonucleotide backbone. Modifications may also be made on the nucleotidic sugar or purine or pyrimidine base, such as 2'-O-alkyl (e.g., 2'-O-methyl), 2'-O-allyl, 2'-amino, or 2'-halo (e.g., 2'-F). A variety of other substitutions are also known in the art and may be used in the present invention. More than one type of nucleotide modification may be used in a single modified oligonucleotide. In addition, portions of the ribozyme may contain one or more non-nucleotidic moieties.

A specific application of generating inhibitors which are either complementary oligonucleotides or inhibitory oligopeptides is described in Holzmayer, Pestov, and Roninson, "Isolation of dominant negative mutants and inhibitory antisense RNA sequences by expression selection of random DNA fragments," *Nucleic Acids Research* 20:711-717 (1992). In this study, genetic suppressor elements (GSEs) are identified by random DNA fragmentation and cloning in expression plasmids.

Preferred oligonucleotide inhibitors include oligonucleotide analogues which are resistant to degradation or hydrolysis by nucleases. These analogues include neutral, or non-ionic, methylphosphonate analogues, which retain the ability to interact strongly with complementary nucleic acids. Miller and Ts'O, *Anti-Cancer Drug Des.* 2:11-128 (1987). Further oligonucleotide analogues include those containing a sulfur atom in place of the 3'-oxygen in the phosphate backbone, and oligonucleotides having one or more nucleotides which have modified bases and/or modified sugars. Particularly useful modifications include phosphorothioate linkages and 2'-modification (e.g., 2'-O-methyl, 2'-F, 2'-amino).

In addition to ribozymes and derivatives thereof, other catalytic nucleic acid molecules can be obtained which also are able to cleave target nucleic acid sequences. A variety of different methods for obtaining such catalytic molecules, including methods for ribozyme "evolution" using iterative selection and mutation and/or methods using a combinatorial approach using short building blocks. Such approaches can also be combined with rational design methods utilizing knowledge of the catalytic regions of known ribozymes and other catalytic nucleic acid molecules. Examples of such methods are provided in the literature, for example, Orgel, 1979, *Proc. R. Soc. London* B205:435; Joyce, 1989, *Gene* 82:83-87; Beaudry et al., 1992, *Science* 257:635-641; Joyce, 1992, *Scientific American* 267:90-97; Breaker et al., 1994, *TIBTECH* 12:268; Bartel et al., 1993, *Science* 261:1411-1418; Szostak, 1993, *TIBS* 17:89-93; Kumar et al., 1995, *FASEB J.* 9:1183; Breaker 1996, *Curr. Op. Biotech.*, 7:442; Breaker, 1997, *Nature Biotech.* 15:427; Campbell et al., 1995, *RNA* 1:598; Lieber et al., 1995, *Mol. Cell. Biol.* 15:540; Lieber et al., International Publication WO 96/01314; Szostak, 1988 in *Redesigning the Molecules of Life*, Ed. S. A. Brenner, pp.87ff, Springer-Verlag, Germany; Kramer et al., U.S. Pat. No. 5,616,459; Joyce, U.S. Pat. No. 5,595,873; Szostak et al., U.S. Pat. No. 5,631,146; Nakamaye & Eckstein, 1994, *Biochemistry* 33:1271; Long & Uhlenbeck, 1994, *Proc. Natl. Acad. Sci.* 91:6977; Ishizaka et al., 1995, *BBRC* 214:403; Vaish et al., 1997, *Biochemistry* 36:6495; and Berzal et al., 1993, *EMBO J.* 12:2567.

Further, using similar iterative selection and modification methods, enzymatic nucleic acid molecules can be obtained which catalyze reactions different from the cleavage of an ester linkage in a ribonucleic acid sequence. For example, an aptamer approach can be used, in which a nucleic acid molecule is selected which binds to a desired target molecule. That nucleic acid molecule is then utilized in rounds of selection and modification to identify at least one molecule which catalyzes the desired reaction. Thus, such catalytic nucleic acid molecules can be used in accessory treatment methods as described herein to inhibit or enhance a cellular process thereby enhancing the effectiveness of the thiamin deficiency induced apoptosis or the converse.

Alternatively, such catalytic nucleic acid molecules can be obtained which act as thiamin cleaving or thiamin inactivating compounds, as catalytic nucleic acid molecules can be developed that cleave substrates other than RNA (Wilson & Szostak, 1995). For example, a catalytic nucleic acid molecule which cleaves the methylene bridge of thiamin (i.e., a synthetic thiaminase) could be developed from random sequence RNAs. These molecules could be used as described for thiaminases and thiaminase derivatives to create a thiamin deficiency in a localized manner.

As described for ribozymes and antisense oligonucleotides, such other catalytic nucleic acid molecules may be delivered using a gene therapy approach, e.g., using expression of the desired molecule from a plasmid encoding the molecule. Alternatively, the nucleic acid molecule may be used to obtain active synthetic derivatives, as for ribozymes, which render the molecule more resistant to degradation and/or increase the catalytic activity. Such derivatives can be delivered in a targeted manner.

E. Use of a Prodrug to Enhance the Effectiveness of Thiamin Deficiency Induced Apoptosis "Prodrugs" are currently being developed for targeted cancer therapy (Bagshawe, 1995; Blakey et al., 1995). Prodrugs of this type are compounds that are themselves not toxic (or have low toxicity), but which become toxic when activated by enzymes that have been targeted to the tumors. (Another prodrug example described above is an inactive precursor of a thiamin-cleaving compound which is chemically modified, e.g., cleaved, to produce an active compound.) The use of such a prodrug depends on the availability of a foreign enzymes, i.e., one not naturally found in the host, to activate the drug. An example of a prodrug enzyme combination is the use of the prodrug ganciclovir (not toxic), together with the herpes simplex virus thymidine kinase gene. The viral enzyme phosphorylates ganciclovir, converting it into a compound that kills cells. This prodrug-enzyme combination is currently being developed for cancer therapy (for references see Aghi et al., 1998).

As described herein, the enzyme thiaminase, or any thiaminase derivative or synthetic thiamin-cleaving compound, is not naturally found in mammals, e.g., humans, and thus constitutes a foreign enzyme. Such an enzyme can cleave thiamin, thereby depleting thiamin, but can also be used to cleave a prodrug, where the cleaving enzyme is localized, or targeted. Such a prodrug is preferably a compound structurally related to thiamin which preferably does not provide vitamin B-1 activity. A cleavage product of the prodrug would be selected or designed to be lethal to adjacent cells, preferably by inducing apoptosis. The ability to obtain such a thiamin-related prodrug (TRP) is indicated by the observation that thiaminase is able to cleave many derivatives of thiamin (see, e.g., Murata, 1982). An approach to developing a TRP can be as follows:

1. Combinatorial chemistry is used to create libraries of modified thiamin derivatives (for example, fluoro-derivatives of various pyrimidine-methylene bridge-thiazole compounds).
2. Each compound in the library is tested in three cell-culture assays, which are generally available and can be easily adapted for large scale testing of compounds.
   i. assay for vitamin B-1 activity for the growth of mammalian cells in culture in thiamin-deficient medium;
   ii. assay for direct toxicity for the growth of mammalian cells in culture with thiamin supplied; and
   iii. assay for toxicity to mammalian cells in culture after the compound is treated with thiaminase or a selected thiamin-cleaving catalyst. If toxicity is found, it would be characterized, e.g., with respect to growth-arrest vs. cell killing, apoptosis vs. necrosis; latent period, etc.

Suitable candidate compounds would not substitute for thiamin in test i, would not be directly toxic to cells in test ii, but would become toxic in test iii after treatment (cleavage) with thiaminase.

The use of a thiamin-related prodrug would enhance the effectiveness of thiamin deficiency induced apoptosis, as any tumor cells that escaped killing by thiamin deficiency could be killed by the localized production of the toxic prodrug product.

One of the factors that should be considered with many low-molecular weight prodrugs is diffusion (or other transport process) of the toxic cleavage product and undesired toxicity to surrounding tissues. In therapies with a targeted thiamin depleting agent, alone or in combination with anti-angiogenesis or other therapy, the treatment is preferably continued for several days. On possible method for controlling undesired toxic prodrug product diffusion is to stage the treatment, adding the prodrug near the conclusion of therapy rather than during the full period of thiamin depletion. In this way potential difficulties associated with diffusion can be reduced while killing cells that survived the thiamin depletion. Alternatively, the prodrug could be administered in pulse mode. In this way, the prodrug would be administered in discrete intervals or doses with sufficient separation in time to allow the toxic products to dissipate between administrations so that surrounding tissue is not subjected to levels of the toxic product sufficient to result in significant tissue damage.

F. Use of Generalized Thiamin Deficiency in Conjunction with Localized Thiamin Deficiency Induced Apoptosis The creation of a generalized thiamin deficiency, preferably a subclinical deficiency, in the body of a person who is to be treated with LAIDT can enhance the ability of the localized treatment to induce apoptosis of the targeted cells by lowering the amount of thiamin within the targeted cells, or available to those cells from other parts of the body. Such a generalized subclinical thiamin deficiency can be created in different ways. For example, the diet provided to the patient can be selected to be deficient in thiamin, or containing a subtoxic dose of a thiamin antimetabolite, or can be pretreated, e.g., with a thiaminase, to destroy available thiamin. In addition, thiaminase-producing bacteria can be localized to the intestines, where the thiaminase can cleave a significant fraction of the ingested thiamin, thereby creating a generalized subclinical thiamin deficiency.

Further, while useful as an accessory treatment along with LAIDT, the creation of a generalized subclinical thiamin deficiency can be useful alone in connection with anti-cancer treatment. In this method, the generalized subclinical thiamin deficiency would affect the actively growing tumor cells to a greater extent than quiescent cells in the body. Thus, creation of a thiamin deficiency at a level insufficient to kill or create significant permanent damage to the patient may still result in apoptosis of the actively growing cancer cells. Alternatively, a generalized subclinical thiamin deficiency can cause actively growing cells to become quiescent, thereby making them more susceptible to apoptosis induced by a localized thiamin deficiency.

G. Use of a Second Apoptosis-inducing Treatment in Conjunction with Thiamin Deficiency Induced Apoptosis In order to enhance the effectiveness and efficiency of apoptosis induction, a second apoptosis-inducing treatment can be used in conjunction with creation of a localized thiamin deficiency. A variety of different conditions and agents are known which induce apoptosis of vertebrate, e.g., human, cells. It is also known that various pathways for apoptosis induction exist and have different response characteristics. Thus, administration of one or more other apoptosis inducing treatments would result in enhanced efficiency of apoptosis induction in the selected group of cells. In most cases it is desirable that the second apoptosis inducing treatment also be targeted to the selected group of cells. Alternatively, where the second treatment results in greater sensitivity of the cells to thiamin deficiency induced apoptosis (or the converse), either or both of the thiamin deficiency and the second method can be targeted.

V. Drug Delivery—Targeted Thiamin Deficiency

A. General

Figure 4:
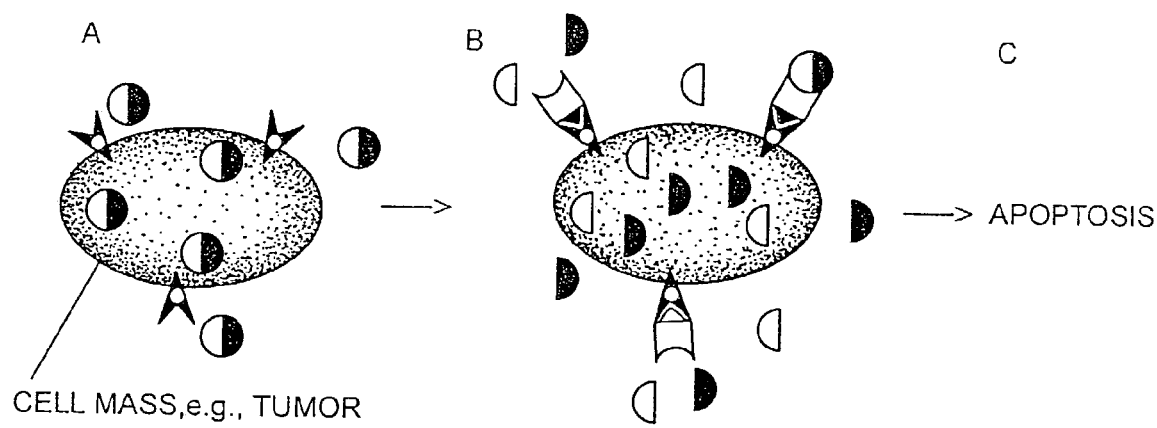
FIG. 4 is a schematic diagram illustrating localized apoptosis induced by the depletion of cellular thiamin (LAIDT). This example illustrates the depletion of cellular thiamin using an extracellular thiamin-cleaving compound, e.g., a thiaminase. In this diagram, a thiaminase is targeted to the cell using a receptor-binding molecule such as an antibody or targeting peptide. The presence of the thiaminase results in the extracellular cleavage of thiamin and thus a depletion of the intracellular thiamin level.

Successful therapy using LAIDT involves surrounding the desired cells, tissue, or organ in vivo to create a sustained thiamin deficiency, such that the target cells become starved for thiamin and remain continuously starved for this vitamin until these cells undergo apoptosis. While the invention is not limited to the use of such compounds, many of our examples use a localized thiamin-cleaving molecule to induce apoptosis in vivo. A general scheme for this approach is illustrated in FIG. 4. Part A shows a cell mass, such as a tumor, before treatment. Thiamin is continually supplied to the cells, to replace that consumed in metabolism. In B, the cell mass is undergoing therapy. Cell surface "receptors," such as antigens, are targeted by a conjugate of a receptor-binding molecule (ligand) with a thiamin-cleaving molecule, such as an antibody-thiaminase. Thiamin brought to the cell mass is cleaved to its components, and the thiamin within the cells is consumed by metabolism. When the thiamin in the cell mass is depleted, the cells undergo apoptosis (C). The method thus involves:

a) efficiently and selectively localizing the thiamin-cleaving molecules to the desired cell mass or masses, b) the presence and thiamin-cleaving activity of the conjugate should be sufficient to continually prevent access of the cell mass to exogenous thiamin until the cells die. In vitro experiments indicate that the thiamin deficiency needs to be maintained for 4 to 13 days, depending on the cell type, before all the cells die.

The following examples of methods to create a localized thiamin deficiency focus mainly on targeted delivery of a death-inducing agent as a thiaminase enzyme (or an active portion thereof). This provides a clearly defined example of a method of inducing localized thiamin deficiency. It has the advantage that, as an enzyme, its effect is amplified: one molecule can destroy many substrate molecules. Being a polypeptide, thiaminase is relatively easy to target to particular cells. It has the additional advantages that the enzyme can work outside of cells and it can create a thiamin deficiency in cells that are adjacent to those directly targeted.

The examples of methods using thiaminase and cancer cells apply to other approaches to creating a thiamin deficiency and to targeted apoptosis of groups of cells other than cancer cells, and thus the examples should not be considered to exclude other approaches to creating a localized thiamin deficiency or to cells other than cancer cells.

B. Delivery of thiaminase

1. General

Normally if a drug is a protein molecule, oral administration would not be suitable because the protein would be digested in the gastrointestinal tract (Benet, 1996). However, at least in the case of the fern thiaminases (from bracken and nardoo), it appears that they retain activity during passage through the gastrointestinal tract. Although examples are described below in which the ingestion of a thiaminase or of bacteria producing thiaminase would produce therapeutic effects, for most targeting purposes it is proposed that thiaminase should be parenterally administered in whichever form proves most suitable in a particular application. As mentioned above, experimental data indicate effective stability of thiaminase introduced parenterally to mice and rats (Ostrovsky et al., 1988). It is also recognized that the resistance of polypeptides, such as thiaminases or thiamin-binding proteins, to degradation can be increased by modifying the polypeptide. Such modifications are understood by those skilled in the art and include chemical modifications and amino acid substitutions.

As a foreign protein, it is anticipated that thiaminase may cause an immune reaction. In previous experiments, we have shown that injection of rabbits with concentrated extracts of *Naegleria*, which we now know contained the *Naegleria* agent (thiaminase I), did not cause sickness or death, although the injections did elicit antibodies to *Naegleria* proteins (Fulton, 1970, p. 454). There is no reason to anticipate that thiaminase would be toxic to animals except by lowering the thiamin concentration. In time, however, it is likely that circulating thiaminase would lead to production of antibodies against itself. Immunosuppression and other methods can be used to extend the therapeutic window. The potential toxicity and immunogenicity of various thiaminases and their derivatives, as well as their stability in vivo, can be monitored by regular animal testing during the development of suitable therapeutic drugs.

Parenteral administration, and especially intravenous infusion of the drug, will subject the conjugated thiaminase to travel in the bloodstream. Human blood contains esterases and proteases which are capable of hydrolyzing some foreign proteins rapidly (Benet, 1996). For each thiaminase, it can be determined whether the core thiaminase activity as well as apoptotic activity of various thiaminases are susceptible to serum proteases. If they are susceptible, the sites of cleavage can be identified and altered by targeted mutagenesis to provide a thiaminase that is not cleaved in the blood. Alternatively, the protein could be encapsulated to protect it in the serum, for example, as described below, or chemically modified.

2. Targeting Thiaminase Using Monoclonal Antibodies to Tumor-associated Antigens Among the methods available for targeting thiamin-depleting compounds to particular groups of cells is the use of antibodies, particularly monoclonal antibodies. Throughout this century, attempts have been made to use antibodies to attack cancers. Recent applications have used monoclonal antibodies coupled to various compounds (reviews: Reisfeld and Cheresh, 1987; Waldmann, 1991; Boleti et al., 1995; Henderson and Finn, 1996). Immunoconjugates include antibodies coupled to radioisotopes for radioimmunotherapy (Kairemo, 1996), to chemotherapeutic agents such as cisplatin to create immunotoxins (Waldmann, 1991; Vitetta et al., 1993), and to enzymes to create immunoenzymes (Bagshawe, 1987; Blakey et al., 1995; Melton and Sherwood, 1996).

In the latter case antibody-enzyme conjugates are being used to target the enzyme to the surface of tumor cells. Once the immunoenzymes are on the surface of the target cells, a prodrug is injected, and the localized enzyme converts the relatively harmless prodrug into a cytotoxic compound that kills the adjacent tumor cells. This procedure is called antibody-dependent enzyme prodrug therapy or ADEPT. Most antigen-enzyme conjugates remain on the surface of the targeted cells, or at least are internalized inefficiently and slowly enough to be useful. Each of these approaches of attaching monoclonal antibodies to various "warheads" (Melton and Sherwood, 1996) to be directed to tumors are giving positive results in cancer therapy, and many are undergoing trials in patients.

Another approach is the selection of human catalytic antibodies that localize to tumors and also possess enzyme activity (Wentworth et al., 1996).

The most useful antibodies have been monoclonal antibodies to tumor-associated antigens, generated in mice. There are numerous antibodies with promising specificities. Some common hurdles in their use are: rapid clearance from the blood giving poor pharmacokinetics, immunogenicity resulting in the development of human anti-mouse antibodies, and poor penetration of solid tumors. To improve on these mouse monoclonal antibodies three major approaches are being used. These approaches rely on genetic engineering to modify and reconstruct the antibodies:

i) Use antibody fragments (e.g., Fab or $F(ab')_2$) or especially genetically engineered smaller antibodies. The most successful of these are constructed "single-chain fragment-variable" or scFv antibodies, in which the heavy chain and light chain variable regions are combined into a single molecule using a peptide linker (Bird et al., 1988; Huston et al., 1993). These scFv antibodies retain their antigen-binding specificity but have smaller size, show better tissue penetration, and frequently are less immunogenic than conventional monoclonal antibodies.

ii) Modify the antibodies so the murine variable regions are surrounded by human antibody framework. These "humanized" antibodies have reduced immunogenicity and improved pharmacokinetics (Jones et al., 1986; Winter and Harris, 1993).

iii) Generate the antibodies in "phage display libraries" (McCafferty et al., 1990; Winter et al., 1994). This procedure allows the generation of diverse antibodies modified as desired. For example, combinatorial libraries are available from which one can select human scFv antibodies of diverse binding specificities.

The genetically-engineered antibodies are usually produced in *Escherichia coli*, although other organisms are also used. Yields of 0.2 to 2 mg of antibody per liter can be obtained in standard laboratory cultures, and in excess of 500 mg per liter in fermenters (Winter et al., 1994).

Herein when antibodies are referred to, they include the possibility of modifications such as the production of human or humanized scFv antibodies.

Antibodies can be stably conjugated to enzymes using chemical procedures, such as intermolecule disulfide bond formation (King et al., 1978; Melton and Sherwood, 1996). Various procedures are used for the coupling of antibodies to compounds other than enzymes (Vitetta et al., 1993). For coupling of two proteins, such an antibody-enzyme, when feasible the preferred procedure is splicing the genes to create the appropriate peptide linkage and then synthesizing the chimeric polypeptide in bacteria (e.g., Chaudhary et al., 1989). A preferred embodiment of such a combination to express for this invention is a human or humanized scFv antibody in peptide linkage with a minimal active core of a suitable thiaminase.

a. Antibodies Available to Use in Antibody-thiaminase Conjugates

Antibodies and various immunoconjugates have been shown to be effective in selectively targeting specific tumors in many animal studies (Pratt and Taylor, 1990, p. 253, and above references). Some of these recognize tumor-associated antigens found on many tumor types but not appreciably on normal cells. An example of an antigen expressed on many human cancers but not on normal cells is $Le^Y$, which is thus a potential tumor target (Brinkmann et al., 1991; Benhar and Pastan, 1995; Scherf et al. 1996). Another example is carcinoembryonic antigen (CEA), a 180 kDa cell surface molecule widely expressed on human cancers, including colon, lung, and breast, and at low levels in normal tissues. A humanized version of an antibody to carcinoembryonic antigen showed excellent tumor targeting (Sharkey et al., 1995). An anti-CEA scFv, selected from a combinatorial library and produced in bacteria, was shown to efficiently find all known tumor deposits in patients (Begent et al., 1996).

Other antibodies tend to target particular types of cancer. For example, melanoma cells were effectively targeted by several antibodies, including human antibodies to the GD2 antigen, which is expressed on 70% of melanomas (Irie and Morton, 1986). Intratumor injection of human anti-GD2 antibodies caused regression of melanomas. In another example, a human scFv from a phage display library, essentially a heavy chain antibody, proved very specific to melanoma cells (Cai and Garen, 1996). Gliomas also are good candidates for antibody therapy. In one of the very positive cases, human glioma intracranial xenographs in athymic rats were treated with intravenously administered $^{131}I$-labeled monoclonal antibody 81C6, which reacts with tenascin, a glioma-associated extracellular matrix component. Tumor-bearing rats treated with this antibody, but not with a $^{131}$I-labeled control antibody, showed significant survival prolongation (Lee et al., 1988; see also Bigner et al., 1995). An antibody such as 81C6, appropriately conjugated to thiaminase, could show more dramatic therapeutic effects in treating these difficult cancers.

Especially promising antibodies are available to target three of the most frequent human cancers, breast, prostate, and colorectal cancers that, when metastatic, are infrequently cured, and for which chemotherapy and radiation often prolong survival only for months.

b. Examples of Use of Antibodies to Target Breast Cancer

Breast cancer is the most frequently diagnosed cancer in women, and the second cause of cancer deaths (Parker et al., 1997). Antibodies such as those against carcinoembryonic antigen can be used to deliver thiaminase to breast cancer. Similarly, a humanized antibody to the HER2 growth factor antigen expressed on breast cancer cells (Baselga et al., 1996) can also be used for delivery. This humanized antibody localized well, was well tolerated, and was clinically beneficial.

Particularly promising is antibody BrE-3, a monoclonal antibody to human milk fat globule that reacts with most human breast cancer biopsies, and is nearly absent in normal tissues. This antibody efficiently eradicated tumors in immunodeficient mice grafted with human breast cancer (Blank et al., 1992). The antibody can deliver radioactivity to widely dispersed breast cancer metastases. In a phase I trial, the antibody conjugated to $^{90}$Y was given to women with advanced breast cancer (Schrier et al., 1995). The major toxicities noted were from the radiation, and objective partial responses were observed in four of eight patients.

Any of these antibodies could be coupled to thiaminase to deliver the enzyme to the surface of breast cancer cells.

C. Example of Use of a Monoclonal Antibody to Target Prostate Cancer

A number of monoclonal antibodies are known that target prostate cancer cells (Abdel-Nabi et al., 1992; Bander, 1994). One example is antibody CYT-346, an IgG1 specific for an antigen expressed on prostate epithelial cells and at higher levels on prostate adenocarcinoma cells (Horoszewicz et al., 1987). CYT-346 is being developed for radioimmunotherapy of androgen-independent prostate cancers (Deb et al., 1996). It is relatively less immunogenic than some other murine monoclonal antibodies. Antibodies such as CYT-346 could be coupled to thiaminase to deliver the enzyme to the external surface of prostate adenocarcinoma cells. Another advantageous choice for targeting to prostate cancer are antibodies that bind to the external domain of prostate-specific membrane antigen (PSMA) as well as to some tumor-specific vascular endothelial cells (Liu et al., 1997).

d. Examples of Use of Monoclonal Antibodies to Target Colorectal Cancer

Colorectal cancer accounts for 8% and 11% of new cancer cases in men and women, respectively, and remarkably deaths caused by these cancers account for 9% and 10% of cancer deaths (Parker et al., 1997). As in most cancers, new therapies are desperately needed.

Monoclonal antibody C242 recognizes a mucin-type glycoprotein commonly expressed on the surface of human colorectal cancer cells. Antibody C242 conjugated to a prodrug was found to be highly cytotoxic toward cultured colon cancer cells in an antigen-specific manner and showed remarkable efficacy in vivo, curing mice with human colon tumor xenografts of their tumors (Liu et al., 1996).

One of the most striking examples of an effective antibody is mouse monoclonal antibody 17-1A, prepared using a human colon cancer cell line as immunogen, which recognizes a tumor-associated glycoprotein (Herlyn et al., 1979). Antibody 17-1A binds to almost all colon adenocarcinomas. Initial evidence of effective tumor targeting by this antibody (Sears et al., 1985) has been followed by extensive clinical trials to treat colorectal cancer patients (Riethmüller et al., 1994). Some prolonged remissions have been obtained using antibody alone (Henderson and Finn, 1996).

These examples just begin to suggest the range of monoclonal antibodies to human tumor-associated antigens that are currently available to target various cancers. In addition, many others are being defined and tested. There are many good candidates available for testing and use in the proposed therapies.

e. Use of Antibody-thiaminase Conjugates

As indicated above, this invention provides antibodies coupled to the catalytic portion of the thiaminase molecule as a means of cancer therapy through antibody targeting of this death-activating agent. To maximize the effectiveness of these antibody-enzyme conjugates, it may be advantageous to make the conjugates small, minimally immunogenic, stable in blood, with high affinity for the targeted cells and yet not efficiently internalized by these cells.

In one approach to administration of the drug, antibody-thiaminase conjugates could be injected by a route appropriate to the tumor under attack. Depending on the results of therapeutic trials, the, antibody-thiaminase could be given as a single injection, multiple doses, or continuous infusion.

Several general considerations govern the use of these conjugates.

Antibodies generally penetrate solid tumors poorly, and most action would therefore take place at the surface of the tumor or in the vascular endothelial cells. Because of the way this therapy works, this need not present a problem. If a tumor is effectively surrounded with thiaminase molecules, this would cause starvation of all of the cells of the tumor for thiamin, resulting in apoptosis even though the antibody-enzyme did not reach every cell. Similarly, most tumors show some heterogeneity in their antigens, and a given antibody is not likely to bind to every tumor cell (Fleuren et al., 1995). Since cells surrounded by thiaminase would deplete the thiamin of adjacent cells (the "bystander effect"; cf. Retta et al., 1996), as long as there is sufficient targeted thiaminase to prevent thiamin from reaching the cells, all the cells should become thiamin starved and undergo apoptosis.

As long as the antibody and enzyme are foreign proteins, the patient may mount an immune response. For example, in one study using a mouse antibody and a bacterial enzyme, patients developed antibody responses to both components in 10-12 days (Melton and Sherwood, 1996). This would limit the time available for treatment, although immunosuppression can be used to extend this therapeutic window. Based on the in vitro experiments with thiaminase, a period of 10-14 days of effective thiamin depletion has been sufficient to induce apoptosis in all cells. At least some in vivo treatment may take longer, for example because of the time required to affect cells throughout a solid tumor when each cell is not surrounded with thiaminase or other thiamin-depleting agent.

Immunoconjugates between selected monoclonal antibodies directed to human tumors and the essential catalytic portion of a thiaminase molecule can be evaluated in vitro for their ability to direct thiaminase specifically to human cancer cells expressing the recognized antigen. The ability of these antibody-thiaminase conjugates to induce apoptosis in cells carrying the antigen but not in cells devoid of antigen can also be established in vitro. The antibody-thiaminase conjugates will be administered parenterally to test animals, and tested for their stability in blood, their toxicity, their immunogenicity, and then their localization to antigen-bearing tumor cells in vivo. The conjugates will also be tested in immunodeficient mice bearing human tumor xenografts for the localization of the conjugates to tumors and their ability to cause regression of these tumors. Once the studies using animal models indicate low toxicity, high selectivity, and effectiveness against tumors, clinical studies in humans would be undertaken.

3. Targeting: Cell Surface Receptors

In addition to the possible use of antibodies to target thiaminase to specific cell surface antigens on a tumor, one can also identify other molecules that will target receptors specific to tumor cells. As an example, a synthetic pentadecapeptide retained the specificity of its parent monoclonal antibody and effectively localized to breast cancers, including metastatic sites (Sivolapenko et al., 1995).

One can obtain a collection of peptides to test, either by dissecting promising antibodies or by generating random peptide sequences using phage display peptide libraries (Smith and Scott, 1993; Barry et al., 1996). In either case the peptides can be screened for those that show selectivity for the cells, tissues, or organ that one wishes to target. Once specific cell-targeting peptides are obtained, they can be attached to thiaminase or a derivative. Such a compound can be constructed by various means, including using recombinant DNA techniques, as described for antibody-thiaminase conjugates. An exemplary demonstration n the therapeutic use of "tumor homing peptides" produced by phage display may be found in a recent paper (Arap et al., 1998) described below.

In a second-generation series of targeting molecules, a targeting peptide can be coupled to a reduced size thiaminase derivative or synthetic thiaminase. This compound, being smaller than natural thiaminase, would localize readily to tumors without being immunogenic or subject to proteolysis. Once prepared, a targeting-peptide conjugated to a thiamin-cleaving peptide or peptidomimetic would be evaluated and employed similarly to the procedures outlined above for antibody-thiaminase conjugates. Such a conjugate can be prepared by genetic engineering methods.

4. Targeting: Liposome-mediated Delivery

Liposomes offer potential advantages for delivering thiamin-depleting compounds to cell masses (Gregoriadis, 1995; Langer, 1998). Liposomes can be used to protect the compounds while directing them to specific cells. Proteins can be protected effectively simply by coating them with polyethylene glycol; the waxy envelope protects them during passage through the blood (Hershfield et al., 1987; see also Ron et al., 1993). Alternatively, the antibody-thiaminase complexes described above could be encapsulated into a liposome that would still target to cells carrying the antigen recognized by the antibody (e.g., Moradpour et al., 1995). One can also generate immunoliposomes directed to their target by a specific antibody but carrying instead of thiaminase a small-molecule analogue of thiamin, such as pyrithiamin or oxythiamin. The delivery of thiamin-depleting drugs using targeted liposomes provides a useful approach.

5. Site-specific Drug Delivery Using Biodegradable Long-circulating Polymeric Nanospheres As an alternative to liposomes, an immunoconjugate of a thiamin-depleting drug and a tumor-directing antibody could be coupled to biodegradable polymers as a means of site-specific drug delivery. Monodisperse biodegradable nanospheres have been developed from amphiphilic copolymers composed of two biocompatible blocks (Gref et al., 1994). These nanospheres are long-circulating in the blood stream and are not eliminated by the reticulo-endothelial system as quickly as conventional injectable monoparticulate carriers. These new nanospheres also have reduced liver accumulation in mice. Furthermore, they trap up to 45% by weight of the drug in the dense core in a one-step procedure and could be freeze-dried and easily redispersed without additives in aqueous solutions. These nanospheres can be targeted, e.g., by attaching an antibody to their polyethylene glycol end group (Gref et al., 1994).

6. Targeting Solid Tumors by Targeting to Surrounding Capillaries

Targeting thiaminase specifically to the endothelial cells of the capillary beds that feed tumors by lining the capillaries that feed a prostate or other tumor mass with a thiamin-cleaving compound, will destroy the thiamin delivered by the blood before it enters the tissue or tumor. "Vascular targeting" using endoglin and other tumor endothelial cell markers is a promising new area of cancer targeting (Thorpe and Burrows, 1995). In addition, using a "phage display" library, peptides have been found that preferentially bind to receptor molecules of the capillaries of a specific tissue; in a first trial, peptides were found that localized to capillaries of mouse brain or kidney (Pasqualini and Ruoslahti, 1996). Homing peptides have been found that recognize specific "addresses" on many cell types and on the specific vascular endothelial cells feeding at least 15 different tissues (Ruoslahti, personal comm., June 1998). Peptides were selected that home specifically to tumor blood vessels. Two of these peptides, with 9 and 13 amino acids, were covalently linked to the chemotherapeutic drug doxorubicin. Targeting the drug markedly increased its effectiveness against human breast cancer xenografts in mice, and markedly reduced its toxicity (Arap et al., 1998). Based on that success, it is expected that specific "addresses" for the vasculature specific to other organs, tissues, and tumors could also be identified and utilized for homing of agents to tumors. By targeting thiaminase to "surround" a specific solid organ (such as the prostate) or solid tumor, the consequence would be starvation of that organ or tissue for thiamin and consequent apoptosis. If the vasculature targeting of the thiamin-depleting compound also eventually destroyed the blood vessels feeding the tumor, that would simply aid in the process. Homing peptides could also be coupled to thiamin antimetabolites to target these to tumor cells or to tumor vascular cells.

A related approach for targeting tumor vasculature utilizes compounds which modulate angiogenesis, or derivatives or analogs of such compounds. Compounds are selected which bind to targets associated with blood vessels or the formation of new blood vessels, preferably tumor blood vessels. Compounds which modulate angiogenesis are particularly advantageous as the site of action of many angiogenesis promoters and inhibitors is at or near the epithelial cells, site of potential blood vessel formation. Thus, if one or more suitable angiogenesis promoters or inhibitors is attached directly or indirectly to an anti-thiamin compound (e.g., a thiamin-cleaving compound such as a thiaminase, or a thiamin antimetabolite) or other compound for which localization is desired (see, e.g., accessory treatments described above), the binding of the angiogenesis promoter or inhibitor in the blood vessels or adjacent tissue, preferably at a site of potential angiogenesis, provides localization of the anti-thiamin compound. Clearly, the angiogenesis promoter or inhibitor can also be replaced in this application by a derivative or analogue which retains selective binding activity, but which may have different or no angiogenesis-related effects.

For compounds which bind to targets in blood vessels generally, localization may be increased, for example, by localized administration upstream of the particular blood vessels which are desired to be affected. As an example, the administration may be by injection upstream of a particular capillary bed. Such localization may be further enhanced by utilizing additional component(s) which enhance binding or blood vessel penetration or cellular uptake of the targeting compound and/or an associated anti-thiamin compound or other compound to be localized.

For compounds which bind to targets associated with tumor angiogenesis, or with tumor neovasculature or tumor vasculature generally, the desired localization can be provided as above by association of binding compound with the anti-thiamin compound (or other compound to be localized). Administration can, for example, be generally into the circulatory system with localization provided by the localized binding to targets only or predominantly located in or around a tumor.

Particular examples of compounds which modulate angiogenesis, particularly those which inhibit, are described above in connection with the use of antiangiogenesis treatments as accessory treatments for creation of localized thiamin deficiency. Those compounds and derivatives and structural analogs of those compounds can be used to identify suitable binding compounds for targeting.

In addition, compounds appropriate for other tumor vasculature-targeted accessory methods and derivatives and analogs of such compounds can also be used to provide targeting and localization of other compounds such as anti-thiamin compounds. As pointed out in the description above of antiangiogenesis accessory methods, examples include compounds which induce inflammation in tumor blood vessels and compounds which induce infarcts in tumor vasculature.

Thus, a variety of targeting compounds can be utilized for localization to tumor blood vessels or the blood vessels supplying another selected group of cells. As described, such targeting compounds bind to targets in or associated with the desired blood vessel localization, or which themselves localize to the desired area, for example, during the process of angiogenesis.

7. Targeting Tumors Using Bacteria a. Utilization of *Salmonella*

Bacterial infections of tumors, sometimes associated with regression of the tumors, have been known for two centuries (Nauts, 1989). There have been many reports of the use of living bacteria for cancer therapy (reviewed in Minton and Oultram, 1988; Pawelek et al., 1997; Saltzman et al., 1997). In one frequent use, since 1976, attenuated "*bacille Calmette-Guèrin*" (BCG) has been instilled intravesically into bladders to reduce recurrence of bladder cancer. The procedure offers benefit (e.g., Lamm et al., 1991).

One especially notable approach involves the use of *Salmonella* spp., especially *S. typhimurium*, for cancer therapy (e.g., Pawelek et al., 1997; Saltzman et al., 1997). For example, it was found (Pawelek et al., 1997) that attenuated (non-pathogenic) hyperinvasive, polyauxotrophic mutants of *S. typhimurium* targeted melanomas in mice, and in vivo reduce the rate of tumor growth and increased survival to as much as twice the survival time of uninfected mice. The bacteria were found at high concentrations in the tumors, both in the necrotic zone of the tumors and inside cells.

The advantageous attributes of *Salmonella* as a living vector to deliver thiaminase to a tumor include:

1. known affinity of *Salmonella* for tumors, and growth therein;
2. presence on these bacteria of systems for invading vertebrate cells;
3. ease of culture;
4. facultative anaerobe, able to grow both aerobically and anaerobically, whether in culture or in tumors;
5. ease of isolating mutants, e.g., attenuated, hyperinvasive, or auxotrophs;
6. availability of the extensive, powerful genetics and molecular biology techniques of enteric bacteria; and
7. extensive knowledge of the pathogenicity of this species.

To use this system for thiamin-deficiency therapy, attenuated, hyperinvasive bacterial strains that efficiently express and secrete thiaminase are engineered, using well known molecular biology techniques. These bacteria would be injected into animals bearing tumors, where they would preferentially locate and grow in the tumors, both intracellularly and extracellularly. The thiaminase produced by those bacteria would cause LAIDT. As with other methods of causing LAIDT, this treatment can be combined with other therapies.

b. Utilization of Anaerobic Bacteria such as *Clostridium* to Target the Hypoxic Interior of Solid Tumors A particular example of the use of bacteria as tumor-specific, amplifiable protein expression vectors is the use of an anaerobe to specifically target the hypoxic environment of tumors.

Metastatic solid tumors present the greatest challenges for cancer therapy. While cells at the surface of the tumor mass often are actively proliferating and usually susceptible to radiation and chemotherapy, the central cells, in addition to being inaccessible, are largely not proliferating and stubbornly resistant to therapeutic treatments (Hickman et al., 1994). The centers of such solid tumors are often hypoxic (oxygen deficient), an environment that favors selection of cells that express bcl-2 but not p53 and thus become highly resistant to apoptosis induced by currently used therapeutic agents (Graeber et al., 1996). Hypoxia in these tumor masses is correlated with insensitivity to non-surgical therapies and a poor prognosis for successful control of the cancer and for patient survival. For example, among 103 patients with advanced cervical carcinomas including solid tumors >3 cm in diameter, 50% of the tumors were hypoxic. The presence of hypoxic tumors was a strong predictor of probable disease recurrence and of poor survival (Höckel et al., 1996).

Based on in vitro studies, it is anticipated that sustained thiamin depletion will induce apoptosis in the non-cycling "dormant" cells of solid tumor masses. In addition to the possibility of "surrounding" tumor masses with a thiamin-cleaving compound, another approach to LAIDT uses anaerobic bacteria as carriers.

Spores of *Clostridium* species have long been known to exhibit remarkable specificity for solid tumors. The spores become localized in, germinate, and grow in the hypoxic tissue (reviewed in Minton et al., 1995). This unique property can be used to locate solid tumors in the body as well as to target therapeutic agents. Even nonpathogenic species kill some of the cancer cells, but infection alone is not sufficient to kill the tumor. For example, *C. butyricum* M-55 injected intravenously or intratumorally caused tumor lysis after 5-8 days, in some cases leaving only the outer rim of cancer cells (which regrew) (e.g., Möse and Möse, 1959; Heppner and Möse, 1978). Any associated toxemia could be controlled with antibiotics.

Recently, nonvirulent *C. beijerinckii* have been genetically engineered to express enzymes that would cleave prodrugs (Minton et al., 1995; Fox et al., 1996). Animals bearing solid tumors are injected with these Clostridia, and, after the bacteria have lodged in the tumors, the animals are injected with the prodrug. Cleavage of the prodrug by the enzyme secreted in the tumor targets the toxic drug to the core of solid tumor.

*Clostridium* sp. that expresses thiaminase can be used to target and infect solid tumors, and thereby induce localized thiamin deficiency. One possibility for a suitable bacterium would be the avirulent *C. sporogenes* ATCC 8075, already known to make and secrete a thiaminase I (Kobayashi, 1975a). The *C. butyricum* M-55 used in early attempts to treat tumors is now classified as *C. sporogenes* ATCC 13732, so is presumably closely related to the strain known to secrete thiaminase. An alternative possibility is to use another species of *Clostridium*, or even another genus of anaerobes. It may be desirable to genetically restrict or attenuate the bacterium used so it will accomplish the effective delivery of thiaminase and induction of apoptosis without causing unwanted sepsis. One possibility would be to use the *C. beijerinckii* currently being used in prodrug experiments (Minton et al., 1995; Fox et al., 1996), and to engineer this strain to overexpress and secrete an appropriate thiaminase.

Treatment of solid tumors with Clostridia expressing thiaminase would induce apoptosis of the central tumor mass. To assure death of the whole tumor mass the *Clostridium*-thiaminase therapy would preferably be coupled with a treatment directed at the peripheral cells, such as conventional radiation and chemotherapy or separately surrounding these cells with thiamin-cleaving compound by some other means, for example, using an antibody-thiaminase conjugate.

8. Targeting Prostate Cancer Using Prostate-specific Antigen

In addition to the delivery of active antithiamin agent, another method is to devise a thiamin-destroying polypeptide that is inactive until activated by a proteolytic cleavage that requires a specific tumor-associated protease. This compound would circulate through the blood stream and be activated specifically where the protease is localized. Prostate cancer provides such an opportunity and example.

Prostate epithelial cells release prostate-specific antigen (PSA), which forms an important constituent of the seminal fluid. Prostate-derived adenocarcinomas also release PSA at $\geq 10$ times the level of normal prostate tissue (Gittes, 1991). PSA is a 33 kDa serine protease with a chymotrypsin-like substrate specificity (Watt et al., 1986; Christensson et al., 1990). The cleavage site of human PSA is specific to human prostate cells, different from those of monkey, baboon, dog, rabbit, or chicken (T. M. Chu, personal communication, December 1996). PSA is enzymatically active in seminal fluid, but most excess PSA released into the blood serum is enzymatically inactive due to binding of the PAS to $\alpha_1$-antichymotrypsin (Christensson et al., 1990; Lilja et al., 1991). Attempts are being made to use the specific serine protease activity of PSA adjacent to prostate cancer cells to convert a harmless prodrug into a drug that would kill the non-cycling prostate cancer cells (Denmeade et al., 1996). PSA is used as an illustrative example; other proteases produced solely or to a sufficiently greater extent in the vicinity of tumor cells to provide localized activation of a prodrug could also be used. For example, kallikrein hD2 is an alternative enzyme for prostate cancer cells.

The PSA can be used to target depletion of thiamin in the environment of PSA-secreting androgen-dependent and androgen-independent prostate cancer cells. Two routes illustrate this method:

a) Develop a prodrug as a peptide with a thiamin analogue that would be cleaved and thus made active by PSA. Existing inhibitors that could form a starting point for such a design include amprolium, which inhibits thiamin uptake into cells, pyrithiamin, which prevents the conversion of thiamin to TPP, and oxythiamin, which is converted to oxy-TPP but inhibits the activity of thiamin-dependent enzymes such as transketolase. In each case, localized release of the analogues would create a thiamin-deficiency induced apoptosis in prostate cancer cells.

b) an inactive catalyst precursor could be designed based on a thiamin-cleaving compound, natural or synthetic, engineered so its catalytic activity was inactive (blocked) until a peptide was cleaved by PSA, analogous to the activation of trypsinogen by cleavage. Such a thiaminase prodrug could be even more effective than thiamin antimetabolite prodrugs, since unblocking a single molecule would initiate the destruction of many molecules of thiamin in the environment of the prostate cancer cells.

These prodrugs and inactive precursors, supplied by intravenous infusion, would circulate through the body but be activated only by PSA-secreting prostate cells. (Small amounts released by any enzymatically active free circulating PSA would be harmless if a proper level of thiamin was maintained in the blood.) At the site of the PSA-secreting cells, the thiamin analogue or thiamin-cleaving compound would be released by the serine protease, where it would produce a localized thiamin deficiency leading to apoptosis of the targeted cells.

Developing a suitable peptide substrate that would be specifically cleaved by PSA could utilize phage display of randomized peptide sequences. This method has already been used to select substrates to specific proteases (Matthews and Wells, 1993; Smith et al., 1995).

Although synthesis of PSA was once thought to be exquisitely specific to prostate cells (Chu, 1994b), recent results indicate the presence of PSA associated with some other tumors, most notably breast cancer (Levesque et al., 1995; Yu et al., 1995). Although the substrate specificity and other features of PSA associated with breast cancer will need to be determined, this finding suggests that PSA could be similarly utilized for thiamin-depletion therapy of breast cancer as well as prostate cancer.

9. Direct Localized Delivery of Drug

This example describes the approach of increasing exposure of cells by localized administration of the drug. In the simplest case, where a tumor mass is localized, injection into the tumor can profoundly localize the product (e.g., Irie and Morton, 1986). In a broader sense, the method of injection can matter. For example, direct injection of cisplatin into the peritoneal cavity yields an intraperitoneal concentration of cisplatin that is $\geq 12$ times that of the plasma (Alberts et al., 1997). In this example intraperitoneal injection increased survival of women with advanced ovarian cancer over intravenous injection (survival for 49 vs. 41 months). This example indicates that even a small molecule tends to stay where it is put.

In order to decrease the toxicity of a chemotherapeutic agent and at the same time to increase the pharmacological effect of the agent on a tumor or metastasis, techniques of localized introduction of the drug have been developed and are extensively used (Ensminger and Gyves, 1984; Benet, 1996). Some procedures involve injection into "third spaces" in the body, such as the peritoneum or cerebrospinal fluid. Another technique consists of the delivery of the chemotherapeutic agent directly to the tumor area by surgical placement of a catheter in the artery that irrigates the tumor or metastasis. Intra-arterial infusion of the chemotherapeutic drug is performed at a predetermined rate by using a subcutaneously attached infusion pump (Ensminger and Gyves, op. cit.). This technique has been extensively used in the treatment of both primary and metastatic cancer of the liver, brain tumors, cancer of the extremities such as sarcomas or melanomas, as well as urogenital tumors. As shown by recent publications, the development of more effective chemotherapeutic agents for inter-arterial administration is an important field of research in cancer therapy (e.g., Munck et al., 1993).

Other methods of directly localized instillation of a chemotherapeutic agent, which allow enrichments up to 1000-fold, include administration of agents directly to the cerebrospinal fluid for the treatment of brain tumors (Werthle et al., 1994) or intraperitoneal administration for treatment of ovarian cancer (Ensminger and Gyves, 1984).

A localized treatment that could be particularly applicable for the direct use of thiaminase would be the intravesical administration of this agent for the treatment of cancer of the bladder (Nseyo and Lamm, 1996). One could even engineer living *bacille Calmette-Guèrin* (BCG) that expressed and excreted thiaminase. The modified BCG could be instilled intravesically into bladders treated for carcinomas (for conditions of treatment, see Lamm et al., 1991). In the bladder, the bacteria could give the benefits of both therapies, the BCG therapy of unknown mechanism and apoptosis induced by thiaminase depletion.

These therapies, which depend on local delivery of therapeutic agents, are primarily suitable for attack on localized tumors, since the agents do not seek distant metastases.

10. Intestinal Thiaminase: Site-specific Delivery to the Gastrointestinal Tract

Thiaminase or thiaminase-producing bacteria offer special opportunities for localized induction of thiamin-deficiency apoptosis in the gut.

Intestinal flora that include a sufficient quantity of thiaminase-producing bacteria are known in some cases to produce an organism-wide thiamin deficiency that can be cured by administration of thiamin. By deliberately colonizing a colon with a thiaminase producer, one could initiate a thiamin deficiency in the colon, thereby inducing apoptosis, while at the same time protecting the rest of the organism by administrating thiamin into the circulation intravenously or intramuscularly. Different bacteria colonize different parts of the intestine (Parsonnet, 1992), including the small intestine (e.g., Albert et al., 1980); one would choose a nonpathogenic strain appropriate to the targeted region. In some cases, one of the thiaminase-producing bacteria already described from the human intestine might be useful (*Bacillus thiaminolyticus, B. aneurinolyticus, C. sporogenes*). In others, it might be more appropriate to engineer another species, such as one of the *Bacteroides* species that is so abundant in the colon, to produce and excrete thiaminase. To assist in colonizing a new bacterium, the patient could be pretreated with lavage and/or antibiotics to reduce existing flora (Chambers and Sande, 1996). For maximum therapeutic effect, one would preferably use a bacterial species that would establish residence, and specifically adhere and become embedded in the mucus of the intestinal epithelial cells (see Cohen and Laux, 1995; Dean-Nystrom, 1995), but would not produce any undesired toxins. When treatment is completed, the thiaminase-producing bacterium could be eliminated using antibiotics.

By choosing specific bacteria adapted to colonize various parts of the body (Sherris, 1984), one could produce localized thiaminase in any tissue that is normally colonized, and thus target thiaminase therapy to other cancers. For example, the vagina could be colonized with a suitable, resident Lactobacillus species that was engineered to produce and excrete thiaminase.

In the gastrointestinal tract, one could potentially obtain the same effect by feeding thiaminase directly, since at least fern thiaminase I appears to be able to survive passage through the digestive system. To protect parts of the gut not involved in the therapy, or to protect the thiaminase until it is needed, one could encapsulate the thiaminase so that it would be released only when it reached the appropriate part of the GI tract, using methods known in the art. (An advantage of using a bacterium producing thiaminase is that it self-renews the therapy as long as needed, and it should not tend to move into other tissues.)

The delivery of thiaminase using colonizing bacteria could be combined with other therapies, even other therapies using thiamin depletion. For example, one could combine, in concurrent therapies, treatments of colorectal cancer that brought thiaminase to the gut, additional thiaminase to surround colon cancer cells brought through the blood using an antibody-thiaminase conjugate, and even thiaminase directed to solid colorectal tumor masses using *Salmonella* or *Clostridium* producing thiaminase, a thiamin antimetabolite brought to the tumor by a homing peptide, or vectors with hypoxia-induced control of expression of a thiamin-depleting agent. In some cases all these thiamin-depleting therapies could be applied simultaneously without any unwanted toxicities or major side effects accompanying the combined assault on a colon or rectal cancer.

11. Targeting by Pulmonary Absorption

In addition to targeting lung cancer by other means, reduction of the active core domain of thiaminase to the size of a peptide (e.g., $\geq 30$ amino acids) will allow an atomized version of thiaminase to be prepared that could be inhaled as fine droplets (aerosol) and absorbed through the pulmonary epithelium and mucus membranes of the respiratory tract. Access to the circulation is rapid by this route, because the surface area is large. Such treatment could produce apoptosis, which would aid in the treatment of lung cancer, which remains the leading cause of cancer deaths in men and women (Parker et al., 1997).

12. Gene Therapy

Introduction of nucleic acid sequences encoding and expressing a thiamin-depleting agent or a plurality of such agents (e.g., a thiaminase) into target cells by gene delivery or gene therapy provides a means to induce a thiamin deficiency and consequently apoptosis in the targeted cells. Some approaches and results in gene therapy were reviewed in Miller (1992); Eck and Wilson (1996); and Anderson (1998). The methods described in those references can be utilized in the present invention.

In connection with the use of gene delivery or gene therapy using thiamin-depleting agents, it is, in general, not necessary to introduce such nucleic acid molecules into all of the potential target cells in an organism, as it is only necessary to reduce the level of thiamin in the target cells, not specifically to express the thiamin-depleting agent in each cell. For example, either of two approaches can provide thiamin depletion in cells which have not been transfected with the nucleic acid sequences. One would be to take advantage of the "bystander effect" (Freeman et al., 1993; Freeman et al., 1996). If a sufficient fraction of cells is genetically transformed so as to express a thiaminase gene to produce thiaminase that was active intracellularly, these cells would undergo thiamin-deficiency apoptosis and release thiaminase; in turn the released thiaminase could induce a thiamin deficiency and apoptosis in surrounding cells. Another approach is to target selected cells with a vector that would encode a thiaminase that the transformed cells would secrete into the extracellular space as active enzyme (e.g., Ridder et al., 1995). Either of these methods could create a cell-type specific, localized thiamin deficiency even if only a fraction of the targeted cells was transformed to produce thiaminase. Preferably a significant fraction of the cells would be transformed. The effectiveness of the gene therapy could be enhanced using a thiamin analogue prodrug activated by the thiaminase, as described above.

Certain vectors used, such as retroviral vectors, transform only dividing cells (Miller et al., 1990), and thus would preferably be used in a manner to take advantage of bystander or vicinity effects, particularly in the case of metastatic cancers that produce solid tumors. Several other vectors are available, including adenovirus vectors and synthetic lipid-DNA vectors that are currently being developed commercially (Brown, 1996). Some in vivo gene therapies for cancer have had encouraging success. For example, cells in a gliomal brain tumor were transformed to sensitivity to a drug (ganciclovir) by adenovirus-mediated gene therapy; treatment caused local regression of primary tumors though not elimination of secondary tumors (Chen et al., 1994).

Many cell types have been targeted for gene therapy, including lung epithelium, transplanted bone marrow cells, skin fibroblasts, and so forth (Watson et al., 1992, Chapter 28; Eck and Wilson, 1996).

Targeting has been accomplished by diverse means, including direct injection, aerosols into the lung, use of a virus with a targeting ligand in its envelope (e.g., Han et al., 1995), addition of a specific ligand to the DNA (Lu et al., 1994), receptor-mediated uptake (Perales et al., 1994), liposome encapsulation (Vieweg et al., 1995), or even systemic administration of a gene that is expressed only in the target tissue (Arteage and Holt, 1996; Lee et al., 1996). The methods listed will allow targeting of suitably engineered genes encoding thiaminase or other thiamin-depleting agent to cancers of the breast, brain, colon, liver, lung, prostate, skin, as well as other tissues.

A new method of targeting gene expression, suitable for use with this invention, is provided by the use of genes or coding sequences whose expression is activated in the hypoxic cells found in the centers of many solid tumors. Such activation can be provided by the use of expression control elements which allow significantly higher expression under hypoxic conditions than under the normally oxygenated conditions present in most tissues. Generally such elements are nucleic acid sequences which regulate transcription of an associated coding sequence and which thus provide inducible control of the transcription level.

A hypoxia-inducible factor-1 (HIF-1) involved in hypoxia-inducible gene expression is found in most if not all mammalian cells. In hypoxic cells, HIF-1 activates expression of genes that contain the hypoxia-responsive element (HRE) in appropriate positional relationship to the gene promoter sequence. The HRE is a sequence element binding site for HIF-1. The use of the HIF-1/IRE system has recently been demonstrated to be of promise for gene therapy of hypoxic tumor cells (Dachs et al., 1997). A suitable vector, using a promoter regulated by the HRE element or a comparable one active in hypoxic cells to drive the expression of a thiaminase gene or its derivative, could be introduced into patients using methods standard to gene therapy, such as those described below. This vector would express the thiaminase gene only, or primarily, in hypoxic cells, as found in solid tumor masses and not in the normally oxygenated tissues of the body. The transfected cells that expressed the thiaminase would die of thiamin deficiency. In turn, if enough of the cells in the tumor mass were transfected, the liberated thiaminase would produce thiamin deficiency in surrounding, untransfected cells. In addition, this therapy could be combined with targeted treatment of thiaminase applied outside of the tumor or outside of the tumor cells. Examples of such vectors, incorporating the HIF-1/HRE system in a retroviral vector system, have been developed (Fox, 1997; Vectors developed by Oxford BioMedica plc, Oxford, U.K.).

Along with the various methods of targeting, a number of different delivery methods can be used. A variety of such delivery methods are known in the art; some methods of delivery that may be used include:

a. complexation with lipids,
b. transduction by retroviral vectors,
c. localization to nuclear compartment utilizing nuclear targeting sites found on most nuclear proteins,
d. transfection of cells ex vivo with subsequent reimplantation or administration of the transfected cells,
e. a DNA transporter system.

A nucleic acid sequence encoding a thiamin-depleting compound may be administered utilizing an ex vivo approach whereby cells are removed from an animal, transduced with the nucleic acid sequence and reimplanted into the animal. For example, the liver can be accessed by an ex vivo approach by removing hepatocytes from an animal, transducing the hepatocytes in vitro with the nucleic acid sequence and reimplanting them into the animal (e.g., as described for rabbits by Chowdhury et al, *Science* 254: 1802-1805, 1991, or for humans by Wilson, *Hum. Gene Ther.* 3: 179-222, 1992) incorporated herein by reference).

Exogenous cells can also be used. In this approach a vector encoding a thiamin-depleting agent, such as a thiaminase, is inserted into cells. If desired, the cells can then be grown in culture. The cells carrying the vector are then delivered into the animal to be treated. Preferably the cells are targeted or localized to the locality of the targeted cells. For example, the cells can be inserted in a tumor mass; expression of the thiamin-depleting agent will induce apoptosis of the surrounding cells.

Many nonviral techniques for the delivery of a nucleic acid sequence encoding a thiamin-depleting polypeptide into a cell can be used, including direct naked DNA uptake (e.g., Wolff et al., *Science* 247: 1465-1468, 1990), receptor-mediated DNA uptake, e.g., using DNA coupled to asialoorosomucoid which is taken up by the asialoglycoprotein receptor in the liver (Wu and Wu, *J. Biol. Chem.* 262: 4429-4432, 1987; Wu et al., *J. Biol. Chem.* 266: 14338-14342, 1991), and liposome-mediated delivery (e.g., Kaneda et al., *Expt. Cell Res.* 173: 56-69, 1987; Kaneda et al., *Science* 243: 375-378, 1989; Zhu et al., *Science* 261: 209-211, 1993). Many of these physical methods can be combined with one another and with viral techniques; enhancement of receptor-mediated DNA uptake can be effected, for example, by combining its use with adenovirus (Curiel et al., *Proc. Natl. Acad. Sci. USA* 88: 8850-8854, 1991; Cristiano et al., *Proc. Natl. Acad. Sci. USA* 90: 2122-2126, 1993).

Expression vectors derived from viruses such as retroviruses, vaccinia virus, adenovirus, adeno-associated virus, herpes viruses, several RNA viruses, or bovine papilloma virus, may be used for delivery of nucleotide sequences into the targeted cell population (e.g., tumor cells). Methods which are well known to those skilled in the art can be used to construct recombinant viral vectors containing sequences encoding thiamin-cleaving polypeptides or other polypeptide thiamin-depleting agents. See, for example, the techniques described in Sambrook et al. (1989) and in Ausubel et. al., *Current Protocols in Molecular Biology*, Greene Publishing Associates and Wiley Interscience, N.Y. (1989). Alternatively, recombinant nucleic acid molecules encoding thiamin-depleting protein sequences can be used as naked DNA or in a reconstituted system e.g., liposomes or other lipid systems for delivery to target cells (see e.g., Feigner et. al., *Nature* 337:387-8, 1989). Several other methods for the direct transfer of plasmid DNA into cells exist for use in human gene therapy and involve targeting the DNA to receptors on cells by complexing the plasmid DNA to proteins.

In its simplest form, gene transfer can be performed by simply injecting minute amounts of DNA (e.g., a plasmid vector encoding a thiamin-depleting polypeptide into the nucleus of a cell, through a process of microinjection (Capecchi M R, *Cell* 22:479-88 (1980)). The DNA can be part of a formulation which protects the DNA from degradation or prolongs the bioavailability of the DNA, for example by complexing the DNA with a compound such as polyvinylpyrrolidone. Once recombinant genes are introduced into a cell, they can be recognized by the cells' normal mechanisms for transcription and translation, and a gene product will be expressed. Other methods have also been used for introducing DNA into larger numbers of cells. These methods include: transfection, wherein DNA is precipitated with $CaPO_4$ and taken into cells by pinocytosis (Chen C. and Okayama H, *Mol. Cell Biol.* 7:2745-52 (1987)); electroporation, wherein cells are exposed to large voltage pulses to introduce holes into the membrane (Chu G. et al., *Nucleic Acids Res.*, 15:1311-26 (1987)); lipofection/liposome fusion, wherein DNA is packaged into lipophilic vesicles which fuse with a target cell (Feigner P L., et al., *Proc. Natl. Acad. Sci. USA.* 84:7413-7 (1987)); and particle bombardment using DNA bound to small projectiles (Yang N S. et al., *Proc. Natl. Acad. Sci.* 87:9568-72 (1990)). Another method for introducing DNA into cells is to couple the DNA to chemically modified proteins.

It has also been shown that adenovirus proteins are capable of destabilizing endosomes and enhancing the uptake of DNA into cells. The admixture of adenovirus to solutions containing DNA complexes, or the binding of DNA to polylysine covalently attached to adenovirus using protein crosslinking agents substantially improves the uptake and expression of the recombinant gene (Curiel D T et al., *Am. J. Respir. Cell. Mol. Biol.*, 6:247-52 (1992)).

As used herein "gene transfer" means the process of introducing a foreign nucleic acid molecule into a cell. Gene transfer is commonly performed to enable the expression of a particular product encoded by the gene. The product may include a protein, polypeptide, anti-sense DNA or RNA, or enzymatically active RNA. Gene transfer can be performed in cultured cells or by direct administration into animals. Generally gene transfer involves the process of nucleic acid contact with a target cell by non-specific or receptor mediated interactions, uptake of nucleic acid into the cell through the membrane or by endocytosis, and release of nucleic acid into the cytoplasm from the plasma membrane or endosome. Expression may require, in addition, movement of the nucleic acid into the nucleus of the cell and binding to appropriate nuclear factors for transcription.

As used herein "gene therapy" is a form of gene transfer and is included within the definition of gene transfer as used herein and specifically refers to gene transfer to express a therapeutic product from a cell in vivo or in vitro. Gene transfer can be performed ex vivo on cells which are then transplanted into a patient, or can be performed by direct administration of the nucleic acid or nucleic acid-protein complex into the patient.

In another preferred embodiment, a vector having nucleic acid sequences encoding a thiamin-depleting agent is provided in which the nucleic acid sequence is expressed only in specific tissue. Examples or methods of achieving tissue-specific gene expression are described in International Publication No. WO 93/09236, published May 13, 1993, filed Nov. 3, 1992.

The nucleic acid sequences appropriate for use in this invention can encode various types of thiamin-depleting agents, which are generally peptides or proteins. Thus, for example, the encoded agent can be a thiaminase or fragment or polypeptide derivative of a thiaminase or a thiamin-sequestering polypeptide.

In all of the preceding vectors set forth above, a further aspect of the invention is that the nucleic acid sequence encoding a thiamin-depleting agent contained in the vector may include additions, deletions or modifications to some or all of the sequence of the nucleic acid, as described above or as known in the art.

C. Antidote

Any regime of drug administration, especially those involving conventional chemotherapies, includes the possibilities of drug overdose. Even with targeted application of agents to induce a localized thiamin deficiency, it is always possible that an overdose could occur and produce more widespread effects than intended. With most chemotherapeutic agents, once the agent is injected there is no ready antidote. A fortunate feature of our proposed therapies is that an effective antidote to thiamin-deficiency therapies is always readily available. This antidote can be applied quickly in large, non-toxic, inexpensive, easily administered doses, even after symptoms of thiamin deficiency appear.

Many have reported the remarkably rapid recovery of animals and of people from thiamin deficiency, even after dramatic symptoms develop. For example, Peters describes the development of symptoms of thiamin deficiency in pigeons, up to convulsions and head retraction, and notes that these symptoms "could be cured in a matter of minutes when thiamin was injected into the subarachnoid space in the brain" (Peters, 1963). In another example, when mice were caused to develop a thiamin deficiency by pyrithiamin could no longer stand upright, they were given thiamin. Improvement was noted within one hour, and within 20 hours the mice had no discernible symptoms (Woolley and White, 1943). The rapid recovery of rats from neurological symptoms produced by ingestion of fern thiaminases has been described. In humans, Platt describes how acute beriberi patients usually recovered within a few hours after being given a few milligrams of thiamin (Platt, 1967). All these observations fit our in vitro result that cells can be brought to the brink of apoptosis by thiamin deficiency induced by thiaminase, to within hours of death, and yet show full recovery if excess thiamin is added to the culture medium.

When thiamin needs to be administered, there is a very large therapeutic margin, and the vitamin can be administered by virtually any route without adverse reactions. In rats, prolonged overdoses of thiamin for several generations were without effect (Williams and Spies, 1938). Extremely high doses, achieving $\geq 70$ mg of thiamin per liter of blood, can cause respiratory paralysis; artificial respiration enables survival even of these extreme concentrations (Harris et al., 1954). Orally, in humans amounts in excess of 3-10 mg per dose are not absorbed, but instead are excreted in urine and feces. Commonly used doses for rapid administration are 100 mg of thiamin per liter of parenteral fluid for intravenous administration (Marcus and Coulston, 1996) or 50 mg per liter intramuscularly (Wilson, 1991). There is considerable latitude in administering thiamin to prevent unwanted damage due to localized thiamin-deficiency therapy, while at the same time not adversely affecting the ongoing therapy. The need for thiamin can be monitored in urine, blood, and tissues as described.

The ability to reverse the effects of thiamin deficiency until apoptosis begins, and if necessary to rapidly administer large doses of thiamin, offers this form of therapy advantages possessed by few if any others. This ability effectively provides an antidote for this therapy.

VI. Oligopeptide and Polypeptide Chemical Derivatives of Thiamin-Depleting Agents As indicated above, natural thiamin-depleting compounds such as thiaminases can be used to induce apoptosis by thiamin depletion of a selected group of cells. However, such natural thiaminases are estimated to range from about ≦400 to ≧1000 amino acids in length. In order to enhance the in vivo effectiveness of such compounds, it can be advantageous to use the natural polypeptide as a starting point, and to modify the natural compound to provide modifications or derivatives having similar or even improved antithiamin activity, but which have improved properties for in vivo use, such as improved resistance to chemical or enzymatic degradation, reduced antigenicity, improved tissue penetration, or improved delivery characteristics.

In addition to active modifications and derivatives, it can also be useful to provide inactive modifications or derivatives of polypeptide thiamin-depleting compounds. For example, a catalytically inactive thiaminase derivative which has essentially the same epitopes as the corresponding natural thiaminase can be used to induce immunological tolerance in a patient being treated. The induction of tolerance can then allow uninterrupted treatment with the active thiaminase to continue for a significantly longer period of time. Similarly, inactive modifications corresponding to active modified thiaminases or derivatives can be used in a similar manner.

Modified thiamin-depleting polypeptides and derivatives can be produced using a number of different types of modifications to the amino acid chain; many such methods are known to those skilled in the art. The changes can include reduction of the size of the molecule, and/or the modification of the amino acid sequence of the molecule. In addition, a variety of different chemical modifications of the naturally-occurring polypeptide can be used, either with or without modifications to the amino acid sequence or size of the molecule. Such chemical modifications can, for example, include the incorporation of modified or non-natural amino acids or non-amino acid moieties during synthesis or the chain, or the post-synthesis modification of incorporated chain moieties.

The oligopeptides of this invention can be synthesized chemically or through an appropriate gene expression system. Synthetic peptides can include both naturally occurring amino acids and laboratory synthesized, modified amino acids.

Also provided herein are functional derivatives of a polypeptide or protein. By "functional derivative" is meant a "chemical derivative," "fragment," "variant," "chimera," or "hybrid" of the polypeptide or protein, which terms are defined below. A functional derivative retains at least a portion of the function of the protein, for example reactivity with a specific antibody, enzymatic activity or binding activity mediated through noncatalytic domains, which permits its utility in accordance with the present invention.

A "chemical derivative" of the complex contains additional chemical moieties not normally a part of the protein. Such moieties may improve the molecule's solubility, absorption, biological half life, and the like. The moieties may alternatively decrease the toxicity of the molecule, eliminate or attenuate any undesirable side effect of the molecule, and the like. Moieties capable of mediating such effects are disclosed in Alfonso and Gennaro (1995). Procedures for coupling such moieties to a molecule are well known in the art. Covalent modifications of the protein or peptides are included within the scope of this invention. Such modifications may be introduced into the molecule by reacting targeted amino acid residues of the peptide with an organic derivatizing agent that is capable of reacting with selected side chains or terminal residues, as described below.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, chloroacetyl phosphate, N-alkylmaleimides, 3-nitro-2-pyridyl disulfide, methyl 2-pyridyl disulfide, p-chloro-mercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing primary amine-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pK of the guanidine functional group. Furthermore, these reagents may react with the groups of lysine as well as the arginine alpha-amino group.

Tyrosyl residues are well-known targets of modification for introduction of spectral labels by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction carbodiimide (R'—N—C—N—R') such as 1-cyclohexyl-3-(2-morpholinyl(4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Derivatization with bifunctional agents is useful, for example, for cross-linking component peptides to each other or the complex to a water-insoluble support matrix or to other macromolecular carriers. Commonly used cross-linking agents include, for example, 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[p-azidophenyl] dithiolpropioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the alpha-amino groups of lysine, arginine, and histidine side chains (Creighton, T. E., *Proteins: Structure and Molecular Properties*, W. H. Freeman & Co., San Francisco, pp. 79-86 (1983)), acetylation of the N-terminal amine, and, in some instances, amidation of the C-terminal carboxyl groups.

Such derivatized moieties may improve the stability, solubility, absorption, biological half life, and the like. The moieties may alternatively eliminate or attenuate any undesirable side effect of the protein complex. Moieties capable of mediating such effects are disclosed, for example, in Alfonso and Gennaro (1995).

The term "fragment" is used to indicate a polypeptide derived from the amino acid sequence of the protein or polypeptide having a length less than the full-length polypeptide from which it has been derived. Such a fragment may, for example, be produced by proteolytic cleavage of the full-length protein. Preferably, the fragment is obtained recombinantly by appropriately modifying the DNA sequence encoding the proteins to delete one or more amino acids at one or more sites of the C-terminus, N-terminus, and/or within the native sequence.

Another functional derivative intended to be within the scope of the present invention is a "variant" polypeptide which either lacks one or more amino acids or contains additional or substituted amino acids relative to the native polypeptide. The variant may be derived from a naturally occurring polypeptide by appropriately modifying the protein DNA coding sequence to add, remove, and/or to modify codons for one or more amino acids at one or more sites of the C-terminus, N-terminus, and/or within the native sequence.

A functional derivative of a protein or polypeptide with deleted, inserted and/or substituted amino acid residues may be prepared using standard techniques well-known to those of ordinary skill in the art. For example, the modified components of the functional derivatives may be produced using site-directed mutagenesis techniques (as exemplified by Adelman et al., 1983, *DNA* 2:183; Sambrook et al., 1989) wherein nucleotides in the DNA coding sequence are modified such that a modified coding sequence is produced, and thereafter expressing this recombinant DNA in a prokaryotic or eukaryotic host cell, using techniques such as those described above. Alternatively, components of functional derivatives of complexes with amino acid deletions, insertions and/or substitutions may be conveniently prepared by direct chemical synthesis, using methods well-known in the art.

VII. Identification of Thiamin-Depleting Agents

The present invention also concerns the identification and evaluation of thiamin-depleting agents. Such agents can have various types of anti-thiamin activity, including thiamin-cleaving activity (e.g., thiaminases), thiamin-binding or sequestering activity, or thiamin inhibiting activity (antagonists). Such antagonists and other antithiamins can be peptides, antibodies, products from natural sources such as fungal or plant extracts or small molecular weight organic compounds. In general, small molecular weight organic compounds are preferred.

Examples of classes of compounds that can be tested for antithiamin activity are, for example but not limited to, modified derivatives of naturally-occurring thiaminases, thiamin binding compounds, and thiamin antagonists. However, large compound libraries, including combinatorial libraries can also be screened to identify compounds having a desired type of anti-thiamin activity. For example, a plurality of compounds, preferably a large number of compounds can be screened to determine whether any of the compounds causes cleavage of the thiamin molecule, or preferentially binds to the thiamin molecule. Compounds identified as having either of these activities can then be evaluated further for binding or cleavage specificity, and in cell culture and/or animal model systems to determine the pharmacological properties of the compound, including the ability of the compound to induce apoptosis both in vitro and in vivo.

For mixtures of natural products, including crude preparations, once a preparation or fraction of a preparation is shown the have an antithiamin activity, the active substance can be isolated and identified using techniques well known in the art, if the compound is not already available in a purified form.

Compounds can also be screened for their ability to induce apoptosis of vertebrate cells by reducing the level of thiamin available to the cell. The method involves incubating the cells with test compounds. Thus, in this method vertebrate cells are contacted with test compounds, preferably test compounds that have been shown to have an anti-thiamin activity. As described above, the period of time before apoptosis is induced by thiamin depletion varies between cell lines. Thus, the test compound is maintained in contact with the cells for a sufficient time for apoptosis to occur if the test compound is an effective apoptosis-inducing compound. If apoptosis of the cells occurs, this indicates that the test compound is a potentially useful thiamin-depleting agent.

This method is particularly appropriate for testing compounds which have been previously identified as having an anti-thiamin activity (e.g., thiamin cleaving activity as for thiaminases), and for compounds which have structural similarity with at least a portion of a compound known to have anti-thiamin activity (e.g., a thiamin antimetabolite). For example, this includes chemical derivatives of previously identified anti-thiamins, modified or unmodified fragments of other anti-thiamins, gene products from genes homologous to genes encoding known antithiamins or sequences encoding portions or derivatives of such products, and compounds having structural similarity to the binding portion or enzymatic portion of other anti-thiamins. The latter category is especially appropriate for small molecule analogs of the active regions of naturally occurring antithiamins (e.g., the catalytic portion of a natural thiaminase).

VIII. Preparation & Administration of Thiamin-Depleting Agents

For the treatment of patients suffering from a tumor or other condition in which the elimination of a group of cells is desired, the preferred method of preparation or administration will generally vary depending on the type of antithiamin compound to be used. Thus, those skilled in the art will understand that administration methods as known in the art will also be appropriate for the compounds of this invention. Examples have been provided in the section on Drug Delivery.

The particular compound that exhibits anti-thiamin activity can be administered to a patient either by itself, or in pharmaceutical compositions where it is mixed with suitable carriers or excipient(s). In treating a patient exhibiting a disorder or condition of interest, a therapeutically effective amount of an agent or agents is administered. A therapeutically effective dose refers to that amount of the compound that results in amelioration of one or more symptoms or a prolongation of survival in a patient.

Toxicity and therapeutic efficacy of such compounds can be determined by standard pharmaceutical procedures in cell cultures and/or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays. Such information can be used to more accurately determine useful doses in humans. Levels in plasma may be measured, for example, by HPLC or other means appropriate for detection of the particular compound.

The exact formulation, route of administration and dosage can be chosen by the individual physician in view of the patient's condition (see e.g. Fingl et. al., in *The Pharmacological Basis of Therapeutics*, 1975, Ch. 1 p. 1).

It should be noted that the attending physician would know how to and when to terminate, interrupt, or adjust administration due to toxicity, or to organ dysfunctions, or to systemic thiamin deficiency. Conversely, the attending physician would also know to adjust treatment to higher levels if the clinical response were not adequate (precluding toxicity). The magnitude of an administered dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above also may be used in veterinary medicine.

Depending on the specific conditions being treated and the targeting method selected, such agents may be formulated and administered systemically or locally. Techniques for formulation and administration may be found in Alfonso and Gennaro (1995). Suitable routes may include, for example, oral, rectal, transdermal, vaginal, transmucosal, or intestinal administration; parenteral delivery, including intramuscular, subcutaneous, or intramedullary injections, as well as intrathecal, intravenous, or intraperitoneal injections.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular those formulated as solutions, may be administered parenterally, such as by intravenous injection. Appropriate compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve the intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions, including those formulated for delayed release or only to be released when the pharmaceutical reaches the small or large intestine.

The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The thiamin depleting compounds and methods and accessory methods described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, using other thiamin-depleting agents, targeting methods, and/or methods of administration, and other accessory methods to be used in conjunction with thiamin depletion are all within the scope of the present invention. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Thus, additional embodiments are within the scope of the invention and within the following claims.

IX. References

Abdel-Nabi, H., Wright, G. L., Gulfo, J. V., D. P., P., Neal, C. E. and et al. (1992). Monoclonal antibodies and radioimmunoconjugates in the diagnosis and treatment of prostate cancer. Semin. Urol. 10, 45-54.

Abe, M., Ito, S., Kimoto, M., Hayashi, R. and Nishimune, T. (1987). Molecular studies on thiaminase I. Biochim. Biophys. Acta 909, 213-221.

Abe, M., Nishimune, T., Ito, S., Kimoto, M. and Hayashi, R. (1986). A simple method for the detection of two types of thiaminase-producing colonies. FEMS Microbiol. Lett. 34, 129-133.

Aghi, M., Kramm, C. M., Chou, T. C., Breakefield, X. O. and Chiocca, E. A. (1988). Synergistic anticancer effects of ganciclovir/thymidine kinase and 5-fluorocytosine/cytosine deaminase gene therapies. J. Natl. Cancer Inst. 90, 370-380.

Ågren, G. (1945). On the purification of the thiamin-inactivating fish factor. Acta physiol. Scand. 9, 306.

Albert, M. J., Mathan, V. I. and Baker, S. J. (1980). Vitamin $B_{12}$ synthesis by human small intestinal bacteria. Nature 283, 781-782.

Alberts, D. S., Liu, P. Y., Hannigan; E. V., O'Toole, R., Williams, S. D., Young, J. A., Franklin, E. W., Clarke-Pearson, D. L., Malviya, V. K., DuBeshter, B., Adelson, M. D. and Hoskins, W. J. (1997). Intraperitoneal cisplatin plus intravenous cyclophosphamide versus intervenous cisplatin plus intravenous cyclophosphamide for stage III ovarian cancer. New Engl. J. Med. 335, 1950-1955.

Alexander, L., Green, R. G., Evans, C. A. and Wolf, L. E. (1941). Alcohol encephalopathy in man and fish-diet diseases in foxes and fishes. Trans. Am. Neurol. Assoc. 67, 119-122.

Alfonso, R. and Gennaro, L. C. (1995): "Remington: The Science and Practice of Pharmacy, 19th ed." Easton, Pa.: Mack Publishing Co.

Alston, T. A. and Abeles, R. H. (1987). Enzymatic conversion of the antibiotic metronidazole to an analog of thiamine. Arch. Biochem. Biophys. 257, 357-362.

Anderson, W. F. (1998). Human gene therapy. Nature 392 (suppl.). 25-30.

Arap, W., Pasqualini, R. and Ruoslahti, E. (1998). Cancer treatment by targeted drug delivery to tumor vasculature in a mouse model. Science 279, 377-380.

Arteage, C. L. and Holt, J. T. (1996). Tissue-targeted antisense c-fos retroviral vector inhibits established breast cancer xenografts in nude mice. Cancer Res. 56, 1098-1103.

Backstrom, A. D., McMordie, R. A. and Begley, T. P. (1995). Biosynthesis of thiamin I: The function of the thiE gene product. J. Am. Chem. Soc. 117, 2351-2352.

Bagshawe, K. D. (1985). Antibody-directed enzyme prodrug therapy: a review. Drug Dev. Res. 34, 220-230.

Bagshawe, K. D. (1987). Antibody directed enzymes revive anti-cancer prodrug concept. Br. J. Cancer 56, 531-532.

Bander, N. H. (1994). Current status of monoclonal antibodies for imaging and therapy of prostate cancer. Semin. Oncol. 21, 607-612.

Barry, M. A., Dower, W. J. and Johnston, S. A. (1996). Toward cell-targeting gene therapy vectors: Selection of cell-binding peptides from random peptide-presenting phage libraries. Nature Med. 2, 299-305.

Baselga, J., Tripathy, D., Mendelsohn, J., Baughman, S., Benz, C. C., Dantis, L., Sklarin, N. T., Seidman, A. D., Hudis, C. A., Moore, J., Rosen, P. P., Twaddell, T., Henderson, I. C. and Norton, L. (1996). Phase II study of weekly intravenous recombinant humanized anti-p185HER2 monoclonal antibody in patients with HER2/neu-overexpressing metastatic breast cancer [see comments]. *J. Clin. Oncol.* 14, 737-744.

Basu, T. K., Dickerson, J. W. T., Raven, R. W. and Williams, D. C. (1974). The thiamine status of patients with cancer as determined by the red cell transketolase activity. *Int. J. Vitam. Nutr. Res.* 44, 53-58.

Begent, R. H., Verhaar, M. J., Chester, K. A., Casey, J. L., Green, A. J., Napier, M. P., Hope Stone, L. D., Cushen, N., Keep, P. A., Johnson, C. J., Hawkins, R. E., Hilson, A. J. and Robson, L. (1996). Clinical evidence of efficient tumor targeting based on single-chain Fv antibody selected from a combinatorial library. *Nature Med* 2, 979-984.

Benet, L. Z., D. L. Kroetz, and L. B. Sheiner (1996). Pharmacokinetics: The dynamics of drug absorption, distribution, and elimination. In *Goodman and Gilman's The Pharmacological Basis of Therapeutics, Ninth Edition* (ed. Hardman, J. G. and Limbird, L. E.), pp. 3-27. McGraw-Hill: New York.

Benhar, I. and Pastan, I. (1995). Cloning, expression and characterization of the Fv fragments of the anticarbohydrate monoclonal antibodies B I and B5 as single-chain immunotoxins. *Protein Eng.* 7, 1509-1515.

Bernsen, H. J., Rijken, P. F., Peters, H., Bakker, H. and van der Kogel, A. J. (1998). The effect of the anti-angiogenic agent TNP-470 on tumor growth and vascularity in low passaged xenografts of human gliomas in nude mice. *J. Neurooncol.* 38, 51-57.

Bigner, D. D., Brown, M., Coleman, R. E., Friedman, A. H., Friedman, H. S., McLendon, R. E., Bigner, S. H., Zhao, X. G., Wikstrand, C. J., Pegram, C. N. and et al. (1995). Phase I studies of treatment of malignant gliomas and neoplastic meningitis with 131 I-radiolabeled monoclonal antibodies anti-tenascin 81C6 and anti-chondroitin proteoglycan sulfate Me1-14 F (ab')2—a preliminary report. *J. Neurooncol.* 24, 109-122.

Bird, R. E., Hardman, K. D., Jacobson, J. W., Johnson, S., Kaufman, B. M., Lee, S.-M., Lee, T., Pope, S. H., Riordan, G. S. and Whitlow, M. (1988). Single-chain antigen-binding proteins. *Science* 242, 423-426.

Blakey, D. C., Burke, P. J., Davies, D. H., Dowell, R. I., Melton, R. G., Springer, C. J. and Wright, A. F. (1995). Antibody-directed enzyme prodrug therapy (ADEPT) for treatment of major solid tumour disease. *Biochem. Soc. Trans.* 23, 1047-1050.

Blank, E. W., Pant, K. D., Chan, C. M., Peterson, J. A. and Ceriani, R. L. (1992). A novel anti-breast epithelial mucin MoAb (BrE-3). *Cancer* 5, 38-44.

Boehm, T., Folkman, J., Browder, T. and O'Reilly, M. S. (1997). Antiangiogenic therapy of experimental cancer does not induce acquired drug resistance. *Nature* 390, 404-7.

Boleti, E., George, A. J. T. and Epenetos, A. A. (1995). Therapeutic monoclonals. *Biochem. Soc. Trans.* 23, 1044-1047.

Borgstrom, P., Bourdon, M. A., Hillan, K. J., Sriramarao, P. and Ferrara, N. (1998). Neutralizing anti-vascular endothelial growth factor antibody completely inhibits angiogenesis and growth of human prostate carcinoma micro tumors in vivo. *Prostate* 35, 1-10.

Borgstrom, P., Hillan, K. J., Sriramarao, P. and Ferrara, N. (1996). Complete inhibition of angiogenesis and growth of microtumors by anti-vascular endothelial growth factor neutralizing antibody: Novel concepts of angiostatic therapy from intravital videomicroscopy. *Cancer Res.* 56, 4032-4039.

Boros, L. G., Brandes, J. L., Lee, W.-N. P., Cascante, M., Puigianer, J., Revesz, E., Bray, T. M., Schirmer, W. J. and Melvin, W. S. (1998). Thiamine supplementation to cancer patients: a double edged sword. *Anticancer Res.* 18, 595-602.

Boros, L. G., Puigianer, J., Cascante, M., Lee, W. N., Brandes, J. L., Bassilian, S., Yusuf, F. I., Williams, R. D., Muscarella, P., Melvin, W. S. and Schirmer, W. J. (1997). Oxythiamine and dehydroepiandrosterone inhibit the nonoxidative synthesis of ribose and tumor cell proliferation. *Cancer Res.* 57, 4242-4248.

Brinkmann, U., Pai, L. H., FitzGerald, D. J., Willingham, M. and Pastan, I. (1991). B3(Fv)-PE38 KDEL, a single-chain immunotoxin that causes complete regression of a human carcinoma in mice. *Proc. Natl. Acad. Sci. USA* 88, 8616-8620.

Brooks, P. C., Montgomery, A. M. P., Rosenfeld, M., Reisfeld, R. A., Hu, T., Klier, G. and Cheresh, D. A. (1994). Integrin $\alpha\gamma\beta_3$ antagonists promote further tumor regression by inducing apoptosis of angiogenic blood vessels. *Cell* 79, 1157-1164.

Brooks, P. C., Silletti, S., von Schalscha, T. L., Friedlander, M. and Cheresh, D. A. (1998). Disruption of angiogenesis by PEX, a noncatalytic metalloproteinase fragment with integrin binding activity. *Cell* 92, 391-400.

Brown, K. S. (1996). Hunt for viable vectors leads to jobs for gene therapy researchers. *The Scientist* 10, 1, 7.

Cai, X. and Garen, A. (1996). A melanoma-specific VH antibody cloned from a fusion phage library of a vaccinated melanoma patient. *Proc. Natl. Acad. Sci. USA* 93, 6280-6285.

Campbell, S. C., Volpert, O. V., Ivanovich, M. and Bouck, N. P. (1998). Molecular mediators of angiogenesis in bladder cancer. Cancer Res. 58, 1298-1304

Cao, Y., O'Reilly, M. S., Marshall, B., Flynn, E., Je, R. W. and Folkman, J. (1998). Expression of Angiostatin cDNA in a Murine Fibrosarcoma Suppresses Primary Tumor Growth and Produces Long-Term Dormancy of Metastases. *J. Clin. Invest.* 101, 1055-63.

Chambers, H. F. and Sande, M. A. (1996). Antimicrobial agents: General considerations. In *Goodman and Gilman's The Pharmacological Basis of Therapeutics, Ninth Edition* (ed. Hardman, J. G. and Limbird, L. E.), pp. 1029-1056. McGraw-Hill: New York.

Chaudhary, V. J., Queen, C., Junghans, R. P., Waldmann, T. A., FitzGerald, D. J. and Pastan, I. (1989). A recombinant immunotoxin consisting of two antibody variable domains fused to Pseudomonas exotoxin. *Nature* 339, 394-397.

Chen, S.-H., Shine, H. D., Goodman, J. C., Grossman, R. G. and Woo, S. L. C. (1994). Gene therapy for brain tumors: Regression of experimental gliomas by adenovirus-mediated gene transfer in vivo. *Proc. Natl. Acad. Sci. USA* 91, 3054-3057.

Christensson, A., Laurell, C.-B. and Lilja, H. (1990). Enzymatic activity of prostate-specific antigen and its reactions with extracellular serine protease inhibitors. *Eur. J. Biochem.* 194, 755-763.

Chu, G. (1994a). Cellular responses to cisplatin. The roles of DNA-binding proteins and DNA repair. *J. Biol. Chem.* 268, 787-790.

Chu, T. M. (1994b). Prostate-specific antigen in screening of prostate cancer. *J. Clin. Lab. Anal.* 8, 323-326.

Cohen, J. J. (1993). Apoptosis. *Immunol. Today* 14, 126-136.

Cohen, J. J., Duke, R. C., Fadok, V. A. and Sellins, K. S. (1992). Apoptosis and programmed cell death in immunity. *Annu. Rev. Immunol.* 10, 267-293.

Cohen, P. S. and Laux, D. C. (1995). Bacterial adhesion to and penetration of intestinal mucus in vitro. *Methods Enzymol.* 253, 309-314.

Cooper, J. R and Pincus, J. H. (1967). The role of thiamine in nerve conduction. In *Thiamine Deficiency* (ed. Wolstenholme, G. E. W. and O'Connor, M.), pp. 112-121. Little, Brown: Boston.

Costello, C. A., Kelleher, N. L., Abe, M., McLafferty, F. W. and Begley., T. P. (1996). Mechanistic studies on thiaminase I. Overexpression and identification of the active site nucleophile. *J. Biol. Chem.* 271, 3445-3452.

Cowgill, G. R. (1939). The physiology of vitamin $B_1$. In *The Vitamins* (ed. American Medical Association), pp. 159-178. American Medical Association: Chicago.

Dachs, G. U., et al., (1997). Targeting Gene Expression to Hypoxic Tumor Cells. *Nature Medicine* 3(5):515-520.

Da Vita, V. T., Jr., Hellman, S., and Rosenberg, S. A. (1997): "Cancer: Principles and Practice of Oncology, 5th edition." Philadelphia: Lippincott-Raven.

Dean-Nystrom, E. A. (1995). Identification of intestinal receptors for enterotoxigenic *Escherichia coli*. *Methods Enzymol.* 253, 315.

Deb, N., Goris, M., Trisler, K., Fowler, S., Saal, J., Ning, S., Becker, M., Marquez, C. and Knox, S. (1996). Treatment of hormone-refractory prostate cancer with $^{90}$Y-CYT-356 monoclonal antibody. *Clin. Cancer Res.* 2, 1289-1297.

Denmeade, S. R., Lin, X. S. and Isaacs, J. T. (1996). Role of programmed (apoptotic) cell death during the progression and therapy for prostate cancer. *Prostate* 28, 251-265.

Denis, L. J. and Verweij, J. (1997). Matrix metalloproteinase inhibitors: present achievements and future prospects. *Invest. New Drugs* 15, 175-185.

Deolalkar, S. T. and Sohonie, S. (1954). Thiaminase from fresh-water, brackish-water and salt-water fish. *Nature* 173, 489-490.

Deutsch, H. F. and Hasler, A. D. (1943). Distribution of a vitamin $B_1$ destructive enzyme in fish. *Proc. Soc. Exptl. Biol. Med.* 53, 63-65.

Deutsch, H. F. and Ott, G. L. (1942). Mechanism of vitamin $B_1$ destruction by a factor in raw smelt. *Proc. Soc. Exptl. Biol Med.* 51, 119-122.

Deutscher, M. P., (ed.) (1990). Guide to Protein Purification. *Methods Enzymol.* 182, 1-894.

Dixon, F. J. and Mauer, P. H. (1955). Immunologic unresponsiveness induced by protein antigens. *J. Exp. Med.* 101, 245-257.

Donehower, L., Harvey, M., Slagle, B. L., McArthur, M. J., Montgomery, J. C. A., Butel, J. S. and Bradley, A. (1992). Mice deficient for p53 are developmentally normal but susceptible to spontaneous tumors. *Nature* 356, 215-221.

Douthit, H. A. and Airth, R. L. (1966). Thiaminase I of *Bacillus thiaminolyticus*. *Arch. Biochem. Biophys.* 113, 331-337.

Dunnebacke, T. H. and Dixon, J. S. (1989). NACM, a cytopathogen from Naegleria ameba: Purification, production of monoclonal antibody, and immunoreactive material in NACM-treated vertebrate cell cultures. *J. Cell Sci.* 93, 391-401.

Dunnebacke, T. H. and Schuster, F. L. (1971). Infectious agent from a free-living soil amoeba, *Naegleria gruberi*. *Science* 174, 516-518.

Dunnebacke, T. H. and Schuster, F. L. (1977a). Cytopathogenic material from amoebae of the genus Naegleria. In *Microbiology* 1977 (ed. Schlesinger, D.), pp. 583-585. American Society for Microbiology:

Dunnebacke, T. H. and Schuster, F. L. (1985). Morphological response of cultured cells to Naegleria amoeba cytopathogenic material. *J. Cell Sci.* 75, 1-16.

Dunnebacke, T. M. and Schuster, F. L. (1977b). The nature of a cytopathogenic material present in amebae of the genus Naegleria. *Amer. J. Trop. Med. Hyg.* 26, 412-421.

Earl, J. W. and McCleary, B. V. (1994). Mystery of the poisoned expedition. *Nature* 368, 683-684.

Eastman, A. (1990). Activation of programmed cell death by anticancer agents: Cisplatin as a model system. *Cancer Cells* 2, 275-280.

Eck, S. L. and Wilson, J. M. (1996). Gene-based therapy. In *Goodman and Gilman's The Pharmacological Basis of Therapeutics, Ninth Edition* (ed. Hardman, J. G. and Limbird, L. E.), pp. 77-101. McGraw-Hill: New York.

Eckhardt, S. G., Burris, H. A., Eckardt, J. R., Weiss, G., Rodriguez, G., Rothenberg, M., Rinaldi, D., Barrington, R., Kuhn, J. G., Masuo, K., Sudo, K., Atsumi, R., Oguma, T., Higashi, L., Fields, S., Smetzer, L. and Von Hoff, D. D. (1966). A phase I clinical and pharmacokinetic study of the angiogenesis inhibitor, tecogalan sodium, *Ann. Oncol.* 7, 491-496.

Eda, I., Soga, H., Ueoka, M., Okada, A., Yamashita, K. and Shimizu, N. (1998). The suppression of postoperative liver metastasis caused by the continuous intraportal infusion of angiogenesis inhibitor FR-118487 in a rabbit colon cancer model. *Surg. Today* 28, 273-278.

Edwin, E. E. (1979). Determination of thiaminase activity using thiazole-labeled thiamine. *Methods Enzymol.* 62, 113-117.

Einsenstein, T. K., Bushnell, B., Meissler, J. J., Jr., Dalal, N., Schafer, R. and Havas, H. F. (1995). Immunotherapy of a plasmacytoma with attenuated salmonella. *Med. Oncol.* 12, 103-108.

Ellis, R. E., Yuan, J. and Horvitz, H. R. (1991). Mechanisms and functions of cell death. *Annu. Rev. Cell Biol.* 7, 663-698.

Ensminger, W. D. and Gyves, J. W. (1984). Regional cancer chemotherapy. *Cancer Treat. Rep.* 68, 101-115.

Evans, W. C. (1975). Thiaminases and their effects on animals. *Vitamins and Hormones* 33, 467-504.

Evans, W. C., Jones, N. R. and Evans, R. A. (1950). The mechanism of anti-aneurin activity of bracken (*Pteris aquilina*). *Biochem. J.* 46, xxxviii-xxxix.

Ferrari, G., Rossini, S., Giavazzi, R., Maggioni, D., Nobili, N., Soldati, M., Ungers, G., Mavilio, G., Gilboa, E., and Bordignon, C. (1991): An in vivo model of somatic cell gene therapy for hyman severe combined immunodeficiency. *Science* 251:1363-1366.

Field, J. B., Elvehjem, C. A. and Juday, C. (1943). A study of the blood constituents of carp and trout. *J. Biol. Chem.* 148, 261-269.

Fisher, D. E. (1994). Apoptosis in cancer therapy: Crossing the threshold. *Cell* 78, 539-542.

Fleuren, G. J., Gorter, A., Kuppen, P. J., Litvinov, S. and Warnaar, S. O. (1995). Tumor heterogeneity and immunotherapy of cancer. *Immunol. Rev.* 145, 91-122.

Folkman, J. (1997). Angiogenic therapy. In *Cancer: Principles and practice of Oncology*, 5$^{th}$ Ed. (ed. DeVita, V. T., Jr.; Hellman, S. and Rosenberg, S. A.), pp. 3075-3085. Lippincott-Raven; Philadelphia.

Fox, M. E., Lemmon, M. J., Mauchline, M. L., Davis, T. D., Giaccia, A. J., Minton, N. P. and Brown, J. M. (1996). Anaerobic bacteria as a delivery system for cancer gene therapy: in vitro activation of 5-fluorocytosine by genetically engineered clostridia. *Gene Therapy* 3, 173-179.

Fox, S. Oxford BioMedica Builds its Business on Development of Retroviral Vectors. *Genetic Engineering News*, Jun. 15, 1997 at 27.

Freeman, S. M., Abboud, C. N., Whartenby, K. A., Packman, C. H., Koeplin, D. S., Moolten, F. L. and Abraham, G. N. (1993). The "bystander effect": tumor regression when a fraction of the tumor mass is genetically modified. *Cancer Res.* 53, 5274-5283.

Freeman, S. M., Whartenby, K. A., Freeman, J. L., Abboud, C. N. and Marrogi, A. J. (1996). In situ use of suicide genes for cancer therapy. *Semin. Oncol.* 23, 31-45.

Friedrich, W. (1988). *Vitamins*. 339-401. Walter de Gruyter: Berlin.

Fruton, J. S. and Simmonds, S. (1958). "General Biochemistry, 2nd Edition. John Wiley and Sons, New York.

Fujimiya, M. (1951). Studies on thiaminase in human feces. III. Frequency of the disease with thiaminase. *Vitamins* 3, 270.

Fujita, A. (1954). Thiaminase. *Adv. Enzymol.* 15, 389-421.

Fujita, A. (1955). Thiaminase. *Methods Enzymol.* 2, 622-628.

Fujita, A., Nose, Y., Kozuka, S., Tashiro, T., Ueda, K. and Sakamoto, S. (1952a). Studies on thiaminase. I. Activation of thiamine breakdown by organic bases. *J. Biol. Chem.* 196, 289-295.

Fujita, A., Nose, Y., Uyeo, S. and Koizumi, J. (1952b). Studies on thiaminase. IV. Synthesis of thiamine. *J. Biol. Chem.* 196, 313-320.

Fulton, C. (1970). Amebo-flagellates as research partners: The laboratory biology of Naegleria and Tetramitus. *Meth. Cell Physiol.* 4, 341-476.

Fulton, C. (1977). Cell differentiation in *Naegleria gruberi*. *Annu. Rev. Microbiol.* 31, 597-629.

Fulton, C. (1993). Naegleria A research partner for cell and developmental biology. *J. Euk. Microbiol.* 40, 520-532.

Fulton, C. and Dingle, A. D. (1967). Appearance of the flagellate phenotype in populations of Naegleria amebae. *Dev. Biol.* 15, 165-191.

Galardy, R. E., Grobelny, D., Foellmer, H. G. and Fernandez, L. A. (1994). Inhibition of angiogenesis by the matrix metalloprotease inhibitor N-[2R-2-(hydroxamidocarbonymethyl)-4-methylpentanoyl)]-L-tryptophan methylamide. *Cancer Res.* 54, 4715-4718.

Georgiannos, S. N., Weston, P. M. and Goode, A. W. (1993). Micronutrients in gastrointestinal cancer. *Br. J. Cancer* 68, 1195-1198.

Gerschenson, L. E. and Rothello, R. J. (1992). Apoptosis: a different type of cell death. *FASEB J.* 6, 2450-2455.

Gittes, R. F. (1991). Carcinoma of the prostate. *New Engl. J. Med.* 324, 236-245.

Glinsky, G. V., Mossine, V. V., Price, J. E., Bielenberg, D., Glinsky, V. V., Ananthaswamy, H. N. and Feather, M. S. (1996). Inhibition of colony formation in agarose of metastatic human breast carcinoma and melanoma cells by synthetic glycoamine analogs. *Clin. Exp. Metastasis* 14, 253-267.

Graeber, T. G., Osmanian, C., Jacks, T., Housman, D. E., Koch, C. J., Loew, S. W. and Giaccia, A. J. (1996). Hypoxia-mediated selection of cells with diminished apoptotic potential in solid tumours. *Nature* 379, 88-91.

Green, R. G., Carlson, W. C. and Evans, C. A. (1942). *J. Nutrition* 23, 165-174.

Green, R. G., Carlson, W. E. and Evans, C. A. (1941). A deficiency disease of foxes produced by feeding fish. $B_1$ avitaminosis analogous to Wernicke's disease of man. *J. Nutr.* 21, 243.

Gref, R., Minamitake, Y., Peracchia, M. T., Trubetskoy, V., Torchilin, V. and Langer, R. (1994). Biodegradable long-circulating polymeric nanospheres. *Science* 263, 1600-1603.

Gregoriadis, G. (1995). Engineering liposomes for drug delivery: progress and problems. *Trends Biotech.* 13, 527-537.

Gutman, M., Szold, A., Ravid, A., Lazauskas, T., Merimsky, O. and Klausner, J. M. (1996). Failure of thalidomide to inhibit tumor growth and angiogenesis in vivo. *Anticancer Res.* 16, 3673-3677.

Haake, P. (1987). Thiamine-dependent enzymes. In *Enzyme Mechanisms* (ed. Page, M. I. and Williams, A.), pp. 390-403. Royal Society of Chemistry: London.

Hamada, K. (1953). Studies on dispositions of carriers of *Bacillus thiaminolyticus* Matsukawa et Misawa in the intestinal canal, I. On so-called thiaminosis-patients and carriers of *B. thiaminolyticus* Matsukawa et Misawa. *Vitamins* 6, 951-956.

Hamada, K. (1954a). Studies on dispositions of carriers of *Bacillus thiaminolyticus* Matsukawa et Misawa in the intestinal canal, III. On the oral administration of *B. thiaminolyticus* Matsukawa et Misawa on various animals. *Vitamins* 7, 65.

Hamada, K. (1954b). Studies on dispositions of carriers of *Bacillus thiaminolyticus* Matsukawa et Misawa in the intestinal canal, IV. Action of bile and bile acids on various animals on *B. thiaminolyticus* Matsukawa et Misawa on various animals. *Vitamins* 7, 70.

Han, X., Kasahara, N. and Kan, Y. W. (1995). Ligand-directed retroviral targeting of human breast cancer cells. *Proc. Natl. Acad. Sci. USA* 92, 9747-9751.

Hannun, Y. A. (1997): Apoptosis and the ddilemma of cancer chemotherapy. *Blood* 89:1845-1853.

Harris, R. S. (1951). Thiaminase. In *The Enzymes. Chemistry and Mechanism of Action* (ed. Sumner, J. B. and Myrbäck, K.), pp. 1186-1206. Academic Press: New York.

Harris, R. S., Jansen, B. C. P., Wuest, H. M., Unna, K. R. and Sebrell, W. H., Jr. (1954). Thiamine. In *The Vitamins. Chemistry, Physiology, Pathology* (ed. Sebrell, W. H., Jr. and Harris, R. S.), pp. 403-480. Academic Press: New York.

Hartley-Asp, B., Vukanovic, J., Joseph, I. B., Strandgarden, K., Polacek, J. and Isaacs, J. T. (1997). Anti-angiogenic treatment with linomide as adjuvant to surgical castration in experimental prostate cancer. *J. Urol.* 158, 902-907.

Hartmann, A., Blaszyk, H., Kovach, J. S. and Sommer, S. S. (1997). The molecular epidemiology of P53 gene mutations in human breast cancer. *Trends Genet.* 13, 27-33.

Henderson, R. A. and Finn, O. J. (1996). Human tumor antigens are ready to fly. *Adv. Immunol.* 62, 217-256.

Heppner, F. and Möse, J. R. (1978). The liquefaction (oncolysis) of malignant gliomas by a nonpathogenic Clostridium. *Acta Neurochir.* 42, 123-125.

Herlyn, M., Steplewski, Z., Herlyn, D. and Kaprowski, H. (1979). Colorectal carcinoma-specific antigen: detection by means of monoclonal antibodies. *Proc. Natl. Acad. Sci. USA* 76, 1438-1452.

Hershfield, M. S., Buckley, R. E., Greenberg, M. L., Melton, A. L., Schiff, R., Hatem, C., Kurtzberg, J., Markert, M. L., Kobayashi, R. H., Kobayashi, A. L. and Abuchowski, A. (1987). Treatment of adenosine deaminase deficiency with polyethylene glycol-modified adenosine deaminase. *New Engl. J. Med.* 316, 589-596.

Hickman, J. A. (1992). Apoptosis induced by anticancer drugs. *Cancer Metast. Rev.* 11, 121-139.

Hickman, J. A., Potten, C. S., Merrit, A. J. and Fisher, T. C. (1994). Apoptosis and cancer chemotherapy. *Phil. Trans. R. Soc. B* 345, 319-325.

Höckel, M., Schienger, K., Aral, B., Mitze, M., Schäffer, U. and Vaupel, P. (1996). Association between tumor hypoxia and malignant progression in advanced cancer of the uterine cervix. *Cancer Res.* 56, 4509-4515.

Horikawa, Y. (1951). Studies on thiaminase in human feces. *Vitamins* 4, 118, 366.

Horoszewicz, J. S., Kawinski, E. and Murphy, G. P. (1987). Monoclonal antibodies to a new antigenic marker in epithelial prostatic cells and serum of prostatic cancer patients. *Anticancer Res.* 7, 927-935.

Huang, X., Molema, G., King, S., Watkins, L., Edgington, T. S. and Thorpe, P. E. (1997): Tumor infarction in mice by antibody-directed targeting of tissue factor to tumor vasculature. *Science* 275:547-550.

Huston, J. S., McCartney, J., Tai, M.-S., Mottola-Hartshorn, C., Jin, D., Warren, F., Keck, P. and Opperman, H. (1993). *Int. Rev. Immunol.* 10, 195-217.

Hutter, J. A. and Slama, J. T. (1987). Inhibition of thiaminase I from *Bacillus thiaminolyticus*. Evidence supporting a covalent 1,6-dihydropyrimidinyl-enzyme intermediate. *Biochem.* 26, 1969-1973.

Ikehata, H. (1960). The purification of thiaminase II. *J. Gen. Appl. Microbiol.* 6, 30-39.

Inoue, K. and Katsura, E. (1965). Etiology and pathology of beriberi. In *Review of Japanese Literature on Beriberi and Thiamine* (ed. Shimazono, N. and Katsura, E.), pp. 1-28. Igaku Shoin, Ltd.: Tokyo.

Irie, R. F. and Morton, D. L. (1986). Regression of cutaneous metastatic melanoma by intralesional injection with human monoclonal antibody to ganglioside GD2. *Proc. Natl. Acad. Sci. USA* 83, 8694-8698.

Jaffee, E., Dranoff, G., Cohen, L. K., Hauda, K. M., Clift, S., Marshall, F. F., Mulligan, R. C. and Pardoll, D. M. (1993). High efficiency gene transfer into primary human tumor explants without cell selection. *Cancer Res.* 53, 2221-2226.

Jones, P. T., Dear, P. H., Foote, J., Neuberger, M. S. and Winter, G. (1986). Replacing the complementarity-determining regions in a human antibody with those from a mouse. *Nature* 321, 522-525.

Kairemo, K. J. (1996). Radioimmunotherapy of solid cancers: A review. *Acta Oncol.* 35, 343-55.

Kenten, R. H. (1957). The partial purification and properties of a thiaminase from bracken (*Pteridium aquilinum* (L) Kuhn). *Biochem. J.* 67, 25-33.

Kimura, M. (1965). Thiamine decomposing bacteria. In *Review of Japanese Literature on Beriberi and Thiamine* (ed. Shimazono, N. and Katsura, E.), pp. 255-274. Igaku Shoin, Ltd.: Tokyo.

Kimura, Y. and Iwashima, A. (1987). Occurrence of thiaminase II in *Saccharomyces cerevisiae*. *Experientia* 43, 888-890.

King, T. P., Li, Y. and Kochoumian, L. (1978). Formation of protein conjugates via intermolecular disulfide bond formation. *Biochem.* 17, 1499-1505.

Kobayashi, S. (1975a). Thiaminase from *Clostridium sporogenes*. I. Purification of thiaminase I. *Vitamins* 49, 45-51.

Kobayashi, S. (1975b). Thiaminase from *Clostridium sporogenes*. II. Properties of the purified thiaminase I. *Vitamins* 49, 111-119.

Kobayashi, S. (1975c). Thiaminase from *Clostridium sporogenes*. III. Thiamine synthesis by the purified thiaminase I. *Vitamins* 49, 185-194.

Korsmeyer, S. J. (1995). Regulators of cell death. *Trends Genet.* 11, 101-105.

Krampitz, L. O. and Woolley, D. W. (1944). The manner of inactivation of thiamine by fish tissue. *J. Biol. Chem.* 152, 9.

Kudelka, A. P., Verschragen, C. F. and Loyer, E. (1998). Complete remission of metastatic cervical cancer with the angiogenesis inhibitor TNP-470. *N. Engl. J. Med.* 338, 991-992.

Kyprianou, N., Martikainen, P., Davis, L., English, H. F. and Isaacs, J. T. (1991). Programmed cell death as a new target for prostatic cancer therapy. In *Prostate Cancer: Cell and Molecular Mechanisms in Diagnosis and Treatment*. (*Cancer Surveys*, vol 11) (ed. Isaacs, J. T.), pp. 265-277. Cold Spring Harbor Laboratory Press: Cold Spring Harbor, N.Y.

Lai, E. Y., Minucci, S., Coon, H. G. and Fulton, C. (1990). An infective agent from Naegleria amebae induces delayed cell death in mammalian cells. *J. Cell Biol.* 111, 494a (abstr.).

Lamm, D. L., Blumenstein, B. A., Crawford, E. D. and et al. (1991). A randomized trial of intravesical doxorubicin and immunotherapy with bacille Calmette-Guèrin for transitional cell carcinoma of the bladder. *New Engl. J. Med.* 325, 1205-1209.

Langer, R. (1998). Drug delivery and targeting. *Nature* 392 (suppl.). 5-10. Lee, C. H., Liu, M., Sie, K. L. and Lee, M. S. (1996). Prostate-specific antigen promoter driven gene therapy targeting DNA polymerase-alpha and topoisomerase II alpha in prostate cancer. *Anticancer Res.* 16, 1805-1811.

Lee, Y., Bullard, D. E., Humphrey, P. A., Colapinto, E. V., Friedman, H. S., Zalutsky, M. R., Coleman, R. E. and Bigner, D. D. (1988). Treatment of intracranial human glioma xenografts with $^{131}$I-labeled anti-tenascin monoclonal antibody 81C6. *Cancer Res.* 48, 2904-2910.

Levesque, M., Yu, H., D'Costa, M. and Diamantis, E. P. (1995). Prostate specific antigen expression by various tumors. *J. Clin. Lab. Anal.* 9, 123-128.

Levy, Y. Y., Lai, E. Y., Remillard, S. P., Heintzelman, M. B. and Fulton, C. (1996). Centrin is a conserved protein that forms diverse associations with centrioles and MTOCs in Naegleria and other organisms. *Cell Motil. Cytoskeleton* 33, 298-323.

Lienhard, G. E. (1970). Kinetic evidence for a (4-amino-2-methyl-5-pyrimidinyl)methyl-enzyme intermediate in the thiaminase I reaction. *Biochem.* 9, 3011-3020.

Lilja, H., Christensson, C., Dahlen, U. and et al. (1991). Prostate-specific antigen in human serum occurs predominantly in complex with $\alpha_1$-antichymotrypsin. *Clin. Chem.* 37, 1618-1625.

Liu, C., Tadayoni, B. M., Bourret, L. A., Mattocks, K. M., Derr, S. M., Widdison, W. C., Kedersha, N. L., Ariniello, P. D., Goldmacher, V. S., Lambert, J. M., Blattler, W. A. and Chari, R. V. (1996). Eradication of large colon tumor xenografts by targeted delivery of maytansinoids. *Proc. Natl. Acad. Sci. USA* 93, 8618-8623.

Liu, H., Moy, P., Kim, S., Xia, Y., Rajasekaran, A., Navarro, V., Knudsen, B. and Bander, N. H. (1997). Monoclonal antibodies to the extracellular domain of prostate-specific membrane antigen also react with tumor vascular endothelium. *Cancer Res.* 57, 3629-3634.

Lowe, S. W., Ruley, H. E., Jacks, T. and Housman, D. E. (1993). p53-dependent apoptosis modulates the cytotoxicity of anticancer agents. *Cell* 74, 957-967.

Lu, X. M., Fischman, A. J., Jyawook, S. L., Hendricks, K., Tompkins, R. G. and Yarmush, M. L. (1994). Antisense DNA delivery in vivo: liver targeting by receptor-mediated uptake. *J. Nucl. Med.* 35, 269-275.

Maisonpierre, P. C., Suri, C., Jones, P. F., Bartunkova, S., Wiegand, S. J., Radziejewski, C., Compton, D., McClain, J., Aldrich, T. H., Papadopoulos, N., Daly, T. J., Davis, S., Sato, T. N. and Yancopoulos, G. D. (1997): Angiopoietin-2, a natural antagonist for Tie2 that disrupts in vivo angiogenesis. *Science* 277:55-60.

Marcus, R. and Coulston, A. M. (1996). Water-soluble vitamins: The vitamin B complex and ascorbic acid. In *Goodman and Gilman's The Pharmacological Basis of Therapeutics, Ninth Edition* (ed. Hardman, J. G. and Limbird, L. E.), pp. 1555-1572. McGraw-Hill: New York.

Martin, S. J. and Green, D. R. (1995). Apoptosis and cancer: the failure of controls on cell death and cell survival. *Crit. Rev. Oncol. Hematol.* 18, 137-153.

Marucci, L., Varticovski, L. and Arias, I. M. (1997). Effect of a xanthine analog on human hepatocellular carcinoma cells (Alexander) in culture and in xenografts in SCID mice. *Hepatology* 26, 1195-1202.

Matsudaira, P. (1990). Limited N-terminal sequence analysis. *Methods Enzymol.* 182, 602-613.

Matsukawa, D., Chang, S., Fujimiya, M. and Misawa, H. (1955). *J. Vitaminol.* 1, 53-55.

Matthews, D. J. and Wells, J. A. (1993). Substrate phage: Selection of protease substrates by monovalent phage display. *Science* 260, 1113-1117.

McCafferty, J., Griffiths, A. D., Winter, G. and Chiswell, D. J. (1990). Phage antibodies: filamentous phage displaying antibody variable domains. *Nature.* 348, 552-554.

McCleary, B. V. and Chick, B. F. (1977). The purification and properties of a thiaminase I enzyme from nardoo (*Marsilea drummondii*). *Phytochemistry* 16, 207-213.

Melkonyan, H. S., Chang, W. C., Shapiro, J. P., Mahadevappa, M., Fitzpatrick, P. A., Kiefer, M. C., Tomei, L. D. and Umansky, S. R. (1997). SARPs: A family of secreted apoptosis-related proteins. *Pros. Natl. Acad. Sci. USA* 94, 13636-13641.

Melnick, D., Hochberg, M. and Oser, B. L. (1945). *J. Nutrition* 30, 81-88.

Melton, R. G. and Sherwood, R. F. (1996). Antibody-enzyme conjugates for cancer therapy. *J. Natl. Cancer Inst.* 88, 153-165.

Menge, U. (1994). Purification of proteins from cell culture supernatant solutions. *Methods Enzymol.* 228, 617-626.

Mickelsen, O. (1956). Intestinal synthesis of vitamins in the nonruminant. *Vitamins and Hormones* 14,1-95.

Miller, A. D. (1992): Human gene therapy comes of age. *Nature* 357:455-460.

Miller, D. G., Adam, M. A. and Miller, A. D. (1990). Gene transfer by retrovirus vectors occurs only in cells that are actively replicating at the time of infection. *Mol. Cell. Biol.* 10, 4239-4242.

Minchinton, A. I., Fryer, K. H., Wendt, K. R., Clow, K. A. and Hayes, M. M. (1996). The effect of thalidomide on experimental tumors and metastases. *Anticancer Drugs* 7, 339-343.

Minton, N. P. and Oultram, J. D. (1988). Host: vector systems for gene cloning in Clostridium. *Microbiol. Sci.* 5, 310-315.

Minton, N. P., Mauchline, M. L., Lemmon, M. J., Brehm, J. K., Fox, M., Michael, N. P., Giaccia, A. and Brown, J. M. (1995). Chemotherapeutic tumour targeting using clostridial spores. *FEMS Microbiol Rev.* 17, 357-364.

Minz, B. (1938). *Compt. rend. soc. biol.* 127, 1251.

Moradpour, D., Compagnon, B., Wilson, B. E., Nicolau, C. and Wands, J. R. (1995). Specific targeting of human hepatocellular carcinoma cells by immunoliposomes in vitro. *Hepatology* 22, 1527-1537.

Möse, J. R. and Möse, G. (1959). Oncolysis by clostridia. I. Activity of *Clostridium butyricum* (M-55) and other non-pathogenic clostridia against the Ehrlich carcinoma. *Cancer Res.* 24, 212-216.

Mulligan, R. C. (1993): The basic science of gene therapy. *Science* 260:926-931.

Munck, J.-N., Riggi, M., Rougier, P., Chabot, G. G., Ramirez, L. H., Zhao, Z., Bognel, C., Ardouin, P., Herait, P. and Gouyette, A. (1993). Pharmacokinetic and pharmacodynamic advantages of pirarubicin over adriamycin after intraarterial hepatic administration in the rabbit VX2 tumor model. *Cancer Res.* 53, 1550-1554.

Murata, K. (1965). Thiaminase. In *Review of Japanese Literature on Beriberi and Thiamine* (ed. Shimazono, N. and Katsura, E.), pp. 220-254. Igaku Shoin, Ltd.: Tokyo.

Murata, K. (1982). Actions of two types of thiaminase on thiamin and its analogues. *Ann. N. Y. Acad. Sci.* 378, 146-155.

Nauts, H. C. (1989). Bacteria and cancer-antagonisms and benefits. *Cancer Surv.* 8, 713-723.

Nseyo, U. O. and Lamm, D. L. (1996). Therapy of superficial bladder cancer. *Semin. Oncol.* 25, 598-604.

O'Reilly, M. S., Holmgren, L., Chen, C. and Folkman, J. (1996). Angiostatin induces and sustains dormancy of human primary tumors in mice. *Nature Med.* 2, 689-692.

Oparin, D. A. and Zabrodskaya, S. V. (1992). [Antitumor effect of hydroxythiamine in mice with Ehrlich ascites carcinoma] (In Russian). *Eksp. Onkol.* 14, 74-77.

Ostrovsky, Y. M. (1965). [Impermeability of the blood-brain barrier to hydroxythiamine]. *Vopr. Med. Khim.* 11, 95-97.

Ostrovsky, Y. M. (1991). Benefits from thiamine deficiency: Prospects for medicine. In *Biochemistry and Physiology of Thiamin Diphosphate Enzymes.* (ed. Bisswanger, H. and Ullrich., J.), pp. 382-389. VCH: Weinheim.

Ostrovsky, Y. M., Puzach, S. S. and Gorbach, Z. V. (1988). Activity of thiaminase I and its fragments after administration of the enzyme to the animal organism. *Biol. Zentralbl.* 107, 17-20.

Ostrovsky, Y. M., Zimatkina, T. I., Gorenshtein, B. I., Iurkshtovich, T. L. and Ryzhaia, E. V. (1987). [Specific activity of thiamine and oxythiamine immobilized on modified cellulose] (In Russian). *Vopr. Pitan.* 1987, 47-50.

Ostrovsky, Y. M., Zimatkina, T. L., Zimatkin, S. M. and Velichko, M. G. (1985). [Effect of oxythiamin on the growth of Ehrlich's ascites tumor in white mice] (In Russian). *Dokl. Akad. Nauk BSSR* 29, 655-657.

Parker, S. L., Tong, T., Bolden, S. and Wingo, P. A. (1997). Cancer statistics, 1997. *CA Cancer J. Clin.* 47, 5-27.

Parsonnet, J. (1992). Gastrointestinal microbiology. In *Encyclopedia of Microbiology* (ed. Lederberg, J.), pp. 245-258. Academic Press, Inc.: San Diego.

Parsons, S. L., Watson, S. A. and Steele, R. J. (1997). Phase I/II trial of batimastat, a matrix metalloproteinase inhibitor, in patients with malignant ascites. *Eur. J. Surg. Oncol.* 23, 526-531.

Parsons, H. T. (1953). An anti-thiamine effect produced in human subjects by bracken ferns. *J. Amer. Dietetic Assoc.* 31, 790.

Pasqualini, R. and Ruoslahti, E. (1996). Organ targeting in vivo using phage display peptide libraries. *Nature* 380, 364-366.

Pawelek, J. M., Low, K. B. and Bermudes, D. (1997). Tumor-targeted Salmonella as a novel anticancer vector. *Cancer Res.* 57, 4537-4544.

Perales, J. C., Ferkol, T., Beegen, H., Ratnoff, O. D. and Hanson, R. W. (1994). Gene transfer in vivo: sustained expression and regulation of genes introduced into the liver by receptor-targeted uptake. *Proc. Natl. Acad. Sci. USA* 91, 4086-4090.

Peters, R. A. (1963). *Biochemical Lesions and Lethal Synthesis.* 321. Macmillan: New York.

Piccoli, R., Olson, K. A., Vallee, B. L. and Fett, J. W. (1998). Chimeric anti-angiogenenin antibody cAb 26-2F inhibits the formation of human breast cancer xenografts in athymic mice. *Proc. Natl. Acad. Sci. USA* 95, 4579-4583.

Platt, B. S. (1967). Thiamine deficiency in human beriberi and in Wernicke's encephalopathy. In *Thiamine Deficiency* (ed. Wolstenholme, G. E. W. and O'Connor, M.), pp. 135-143. Little, Brown: Boston.

Pluda, J. M. (1997). Tumor-associated angiogenesis: Mechanisms, clinical implications, and therapeutic strategies, *Semin. Oncol.* 24, 203-218.

Pratt, W. B. and Taylor, P. (1990). *Principles of Drug Action: The Basis of Pharmacology, Third Edition.* Churchill Livingstone: New York.

Presta, L. G., Chen, H., O'Connor, S. J., Chisholm, V., Meng, Y. G., Krummen, L., Winkler, M. and Ferrara, N. (1997). Humanization of an anti-vascular endothelial growth factor monoclonal antibody for the therapy of solid tumors and other disorders. *Cancer Res.* 57, 4593-9.

Puzach, S. S. (1991). [The presence of antihiamine factor—thiaminase—in organs of random-bred albino rats and mice] (In Russian). *Vopr. Med. Khim.* 37, 82-84.

Puzach, S. S. (1995). [Approaches to assessing dynamics of permeability and duratioin of thiaminase I action, administered parenterally to animals] (In Russian). *Vopr. Med. Khim.* 41, 43-44.

Puzach, S. S. and Ostrovsky, Y. M. (1976). [Antivitamin activity of thiaminase from freshwater bicuspid moluscs after parenteral administration of the enzyme to albino mice] (In Russian). *Vopr. Med. Khim.* 22, 769-773.

Raff, M. C. (1992). Social controls on cell survival and cell death. *Nature* 356, 397-399.

Rasmussen, H. S. and McCann, P. P. (1997). Matrix metalloproteinase inhibition as a novel anticancer strategy: a review with special focus on batimastat and marimastat. *Pharmacol. Ther.* 75, 69-75.

Reddy, K. K., Giri, K. V. and Das, R. (1948). Thiaminase system in fresh water mussel (*Lamellidens marginalis*). *Enzymologia* 12, 238-245.

Reed, J. C. (1994). bcl-2 and the regulation of programmed cell death. *J. Cell Biol.* 124, 1-6.

Reisfeld, R. A. and Cheresh, D. A. (1987). Human tumor antigens. *Adv. Immunol.* 40, 323-377.

Retta, B. M. E., Burke, P. J., Photiou, A., Melton, R. S. and Encamooquaya, E. (1996). Antibody-directed enzyme prodrug therapy (ADAPT)—Evidence for a bystander effect in vitro. *Intern. J. Oncology* 9, 557-570.

Ridder, R., Geisse, S., Kleuser, B., Kawalleck, P. and Gram, H. (1995). A COS-cell-based system for rapid production and quantification of scFv::IgCK antibody fragments. *Gene* 166, 273-276.

Riethmüller, G., Schneider-Gädicke, E., Schlimok, G., Schmiegel, W., Raab, R., Höffken, K., Gruber, R., Pichlmaier, H., Hirche, H., Pichlmyr, R., Buggisch, P., Witte, J. and the German Cancer Aid 17-1A Study Group (1994). Randomized trial of monoclonal antibody for adjuvant therapy of resected Dukes' C colorectal carcinoma. *Lancet* 343, 1177-1183.

Rogers, E. F. (1970). Thiamine antagonists. *Methods Enzymol.* 18A, 245-258.

Rogers, E. F. (1982). General discussion of antithiamin compounds and thiamin antagonists. *Ann. N.Y. Acad. Sci.* 378, 157-160.

Ron, E., Turek, T., Mathiowitz, E., Chasin, M., Hageman, M. and Langer, R. (1993). Controlled release of polypeptides from polyanhydrides. *Proc. Natl. Acad. Sci. USA* 90, 4176-4180.

Rubin, B. Y., Smith, L. J., Hellermann, G. R., Lunn, R. M., Richardson, N. K. and Anderson, S. L. (1988). Correlation between the anticellular and DNA fragmenting activities of tumor necrosis factor. *Cancer Res.* 48, 6006-6010.

Saltzman, D. A., Katsanis, E., Heise, C. P., Hasz, D. E., Vigdorovich, V., Kelly, S. M., Curtiss, R.r., Leonard, A. S. and Anderson, P. M. (1997). Antitumor mechanisms of attenuated *Salmonella typhimurium* containing the gene for human interleukin-2; a novel antitumor agent? *J. Pediatr. Surg.* 32, 301-306.

Sambrook, J., Fritsch, E. F. and Maniatis, T. (1989). *Molecular Cloning: A Laboratory Manual, 2nd edition.* Cold Spring Harbor Laboratory Press: Cold Spring Harbor, N.Y.

Santos, O., McDermott, C. D., Daniels, R. G. and Appelt, K. (1997). Rodent pharmacokinetic and anti-tumor efficacy studies with a series of synthetic inhibitors of matrix metalloproteinases. *Clin Exp. Metastasis* 15, 449-508.

Scherf, U., Benhar, I., Webber, K. O., Pastan, I. and Brinkmann, U. (1996). Cytotoxic and antitumor activity of a recombinant tumor necrosis factor-B1(Fv) fusion protein on Le$^Y$ antigen-expressing human cancer cells. *Clin. Cancer Res.* 2, 1523-1531.

Schrier, D. M., Stemmer, S. M., Johnson, T., Kasliwal, R., Lear, J., Matthes, S., Taffs, S., Dufton, C., Glenn, S. D., Butchko, G., Ceriani, R. L., Rovira, D., Bunn, P., Shpall, E. J., Bearman, S. I., Purdy, M., Cognoni, P. and Jones, R. B. (1995). High-dose $^{90}$Y Mx-diethylenetriaminepentaacetic acid (DTPA)-BrE-3 and autologous hematopoietic stem cell support (AHSCS) for the treatment of advanced breast cancer: A phase I trial. *Cancer Res.* 55, 5921 s-5924s.

Schwartz, R. H. (1993). Immunological tolerance. In *Fundamental Immunology, Third Edition* (ed. Paul, W. E.), pp. 677-731. Raven Press: New York.

Sealock, R. R., Livermore, A. H. and Evans, C. A. (1943). Thiamine inactivation by the fresh-fish or Chastek-paralysis factor. *J. Am. Chem. Soc.* 65, 935-940.

Sears, H. F., Herlyn, D., Steplewski, Z. and Koprowski, H. (1985). Phase II clinical trial of a murine monoclonal antibody cytotoxic for gastrointestinal adenocarcinoma. *Cancer Res.* 45, 5910-5913.

Seear, M., Lockitch, G., Jacobson, B., Quigley, G. and MacNab, A. (1992). Thiamine, riboflavin, and pyridoxine deficiencies in a population of critically ill children. *J. Pediatr.* 121, 533-538.

Sentman, C. L., Shutter, J. R., Hockenbery, D., Kanagawa, 0. and Korsmeyer, S. J. (1991). bcl-2 inhibits multiple forms of apoptosis but not negative selection in thymocytes. *Cell* 67, 879-888.

Sharkey, R. M., Juweid, M., Shevitz, J., Behr, T., Dunn, R., Swayne, L. C., Wong, G. Y., Blumenthal, R. D., Griffiths, G. L., Siegel, J. A. and et al. (1995). Evaluation of a complementarity-determining region-grafted (humanized) anti-carcinoembryonic antigen monoclonal antibody in preclinical and clinical studies. *Cancer Res.* 55, 5935s-5945s.

Sherris, J. C. (1984). Normal microbial flora. In *Medical Microbiology. An Introduction to Infectious Diseases* (ed. Sherris, J. C.), pp. 50-58. Elsevier: New York.

Sim, B. K., O'Reilly, M. S., Liang, H., Fortier, A. H., He, W., Madsen, J. W., Lapcevich, R. and Nacy, C. A. (1997). A recombinant human angiostatin protein inhibits experimental primary and metastatic cancer. *Cancer Res.* 57, 1329-1334.

Sinicrope, F. A., Roddey, G., McDonnel, T. J., Shen, Y., Cleary, K. R. and Stephens, L. C. (1996). Increased apoptosis accompanies neoplastic development in the human colorectum. *Clin. Cancer Res.* 2, 1999-2006.

Sivolapenko, G. B., Douli, V., Pectasides, D., Skarlos, D., Sirmalis, G., Hussain, R., Cook, J., Courtenay Luck, N. S., Merkouri, E., Konstantinides, K. and et al. (1995). Breast cancer imaging with radiolabelled peptide from complementarity-determining region of antitumour antibody. *Lancet* 346, 1662-1666.

Skobe, M., Rockwell, P., Goldstein, N., Vosseler, S. and Fusenig, N. E. (1997). Halting angiogenesis suppresses carcinoma cell invasion. *Nature Med.* 3, 1222-1227.

Smith, D. C. and Proutt, L. M. (1944). Development of thiamine deficiency in the cat on a diet of raw fish. *Proc. Soc. Exp. Biol. Med* 56, 1-3.

Smith, G. P. and Scott, J. K. (1993). Libraries of peptides and proteins displayed on filamentous phage. *Methods Enzymol.* 217, 228-257.

Smith, M. M., Shi, L. and Narve, M. (1995). Rapid identification of highly active and selective substrates for stromelysin and matrilysin using bacteriophage peptide display libraries. *J. Biol. Chem.* 270, 6440-6449.

Spitzer, E. H., Coombes, A. I., Elvehjem, C. A. and Wisnicky, W. (1941). Inactivation of vitamin $B_1$ by raw fish. *Proc. Soc. Exp. Biol. Med.* 48, 376-381.

Steller, H. (1995). Mechanisms and genes of cellular suicide. *Science* 267, 1445-1449.

Steyn-Parvé (1967). The mode of action of some thiamine analogues with antivitamin activity. In *Thiamine Deficiency* (ed. Wolstenholme, G. E. W. and O'Connor, M.), pp. 26-42. Little, Brown: Boston.

Thomas, B. and Walker, H. F. (1949). Inactivation of thiamine by bracken (*Pteris aquilina*). *J. Soc. Chem. Ind. (Lond.)* 68, 6-9.

Thompson, C. B. (1995). Apoptosis in the pathogenesis and treatment of disease. *Science* 267, 1456-1462.

Thorpe, P. E. and Burrows, F. J. (1995). Antibody-directed targeting of the vasculature of solid tumors. *Breast Cancer Res. Treat.* 36, 237-251.

Trebukhina, R. V. (1983). [Transketolase activity and the TDP effect in tissues of animals with experimental tumors] (In Russian). *Vopr Med Khim* 29, 85-90.

Trebukhina, R. V., Kravchuk, R. I., Mikhal'tsevich, G. N., Petushok, V. G. and Nikitin, V. S. (1987). [Effect of thiamine and its antimetabolite oxythiamine on the proliferative activity of carcinosarcoma Walker 256 cells] (In Russian). *Eksp. Onkol.* 9, 60-63.

Trebukhina, R. V., Ostrovsky, Y. M., Shapot, V. S., Petushok, V. G., Velichko, M. G., Tumanov, V. N. and Mikhaltsevich, G. N. (1982). Thiamine metabolism in the liver of mice with Ehrlich ascites carcinoma. *Neoplasma* 29, 257-268.

Trebukhina, R. V., Petushok, V. G., Tumanov, V. N. and Mikhas'tsevich, G. N. (1986). [Level of thiamine diphosphate in the liver of tumor-bearing animals kept on a diet including an excessive amount of vitamin B1] (In Russian). *Vopr. Pitan.* 1986, 63-65.

Uray, G., Kriessmann, I. and Zoltewicz, J. A. (1993). Dual mechanisms of nucleophilic substitution of thiamin analogs: Estimating the special kinetic effect of sulfite ion. *Bioorg. Chem.* 21, 294-308.

Vaux, D. L., Aquila, H. L. and Weissman, I. L. (1992). Bcl-2 prevents death of factor-deprived cells by fails to prevent apoptosis in targets of cell-mediated killing. *Int. Immunol.* 4, 821-824.

Vedder, E. B. (1939). The pathology of beriberi. In The Vitamins (ed. Association, A. M.), pp. 179-191. American Medical Association: Chicago.

Vieweg, J., Boczkowski, D., Roberson, K. M., Edwards, D. W., Philip, M., Philip, R., Rudoll, T., Smith, C., Robertson, C. and Gilboa, E. (1995). Efficient gene transfer with adeno-associated virus-based plasmids complexed to cationic liposomes for gene therapy of human prostate cancer. *Cancer Res.* 55, 2366-2372.

Vimokesant, S. L., Nakornchi, S., Dhanamitta, S. and Hilker, D. M. (1974). Effect of tea consumption on thiamine status in man. *Nutr. Rep. Int.* 9, 371-374.

Vitetta, E. S., Thorpe, P. E. and Uhr, J. W. (1993). Immunotoxins: magic bullets or misguided missiles? *Trends Pharmacol. Sci.* 14, 148-154.

von Muralt, A. (1947). Thiamine and peripheral neurophysiology. *Vitamins and Hormones* 5, 93-118.

Waldmann, T. A. (1991). Monoclonal antibodies in diagnosis and therapy. *Science* 252, 1657-1662.

Wamil, B. D., Thurman, G. B., Sundell, H. W., DeVore, R. F., Wakefield, G., Johnson, D. H., Wang, Y. F. and Hellerqvist, C. G. (1997). Soluble E-selectin in cancer patients as a marker of the therapeutic efficacy of CM101, a tumor-inhibiting anti-neovascularization agent, evaluated in phase I clinical trial. *J. Cancer Res. Clin. Oncol.* 123, 173-9.

Waring, P. (1990). DNA fragmentation induced in macrophages by gliotoxin does not require protein synthesis and is preceded by raised inositol triphosphate levels. *J. Biol. Chem.* 265, 14476-14480.

Watanabe, H., Nanjo, H., Matsui, K., Chatani, J. and Minoguchi, T. (1955). Studies on the nutritional value of the fern, IV. The effect of the ingestion of bracken on man. *Kokumin Eisei* 21, 137.

Watson, J. D., Gilman, M., Witkowski, J. and Zoller, M. (1992). *Recombinant DNA, 2nd edition*. Scientific American Books: New York.

Watt, K. W. K., Lee, P.-J., M'Timkulu, T., Chan, W.-P. and Loor, R. (1986). Human prostate-specific antigen: Structural and functional similarity with serine proteases. *Proc. Natl. Acad. Sci. USA* 83, 3166-3170.

Weiner, H. L., Friedman, A., Miller, A., Khoury, S. J., Al-Sabbagh, A., Santos, L., Sayegh, M., Nussenblatt, R. B., Trentham, D. E. and Hafler, D. A. (1994). Oral tolerance: Immunologic mechanisms and treatment of animal and human organ-specific autoimmune diseases by oral administration of autoantigens. *Annu. Rev. Immunol.* 12, 809-837.

Wenckebach, K. F. (1928). St. Cyres lecture on heart and circulation in tropical avitaminosis (beri-beri). *Lancet* 2, 265-268.

Wentworth, P., Datta, A., Blakey, D., Boyle, T., Partridge, L. J. and Blackburn, G. M. (1996). Toward antibody-directed "abzyme" prodrug therapy, ADAPT: Carbamate prodrug activation by a catalytic antibody and its in vitro application to human tumor cell killing. *Proc. Natl. Acad. Sci. USA* 93, 799-803.

Werthle, M., Bochelen, D., Adamczyk, M., Kupferberg, A., Poulet, P., Chambron, J., Lutz, P., Privat, A. and Mercel, M.

(1994). Local administration of 7β-hydroxycholesteryl-3-oleate inhibits growth of experimental rat C6 glioblastoma. *Cancer Res.* 54, 998-1003.

Weswig, P. H., Freed, A. M. and Haag, J. R. (1946). Antithiamine activity of plant materials. *J. Biol. Chem.* 165, 737-738.

White, E. (1993). Death-defying acts: a meeting review on apoptosis. *Genes Dev.* 7, 2277-2284.

Williams, R. R. (1961). *Toward the Conquest of Beriberi.* Harvard University Press: Cambridge.

Williams, R. R. and Spies, T. D. (1938). *Vitamin B1 (Thiamine) and Its Use in Medicine.* Macmillan: New York.

Williams, R. R., Waterman, R. E., Keresztesy, J. C. and Buchman, E. R. (1935). Studies on crystalline vitamin $B_1$. III. Cleavage of vitamin with sulfite. *J. Am. Chem. Soc.* 57, 536-537.

Wilson, C. and Szostak, J. W. (1995). In vitro evolution of a self-alkylating ribozyme. *Nature* 374, 777-782.

Winter, G., Griffiths, A. D., Hawkins, R. E. and Hoogenboom, H. R. (1994). Making antibodies by phage display technology. *Annu. Rev. Immunol.* 12, 433-455.

Winter, G. and Harris, W. J. (1993). Humanized antibodies. *Trends Pharm. Sci.* 14, 139-143.

Wittliff, J. L. and Airth, R. L. (1968). The extracellular thiaminase I of *Bacillus thiaminolyticus*. I. Purification and physicochemical properties. *Biochem.* 7, 736-744.

Wittliff, J. L. and Airth, R. L. (1970a). Thiaminase I. *Methods Enzymol.* 18, 229-234.

Wittliff, J. L. and Airth, R. L. (1970b). Thiaminase II. *Methods Enzymol.* 18, 234-238.

Woolley, D. W. (1941). Destruction of thiamin by a substance in certain fish. *J. Biol. Chem.* 141, 997-998.

Woolley, D. W. (1951 a). An enzymatic study of the mode of action of pyrithiamine (neopyrithiamine). *J. Biol. Chem.* 191, 43-54.

Woolley, D. W. (1951 b). Enzymatic synthesis of folic acid by the action of carp thiaminase. *J. Am. Chem. Soc.* 73, 1898.

Woolley, D. W. (1953). Biosynthesis and energy transport by enzymatic reduction of onium salts. *Nature* 171, 323-328.

Woolley, D. W. and Merrifield, R. B. (1954). Demonstration by the aid of pyrithiamine of a new action of thiamine. *Bull. soc. chim. biol.* 36, 1207-1212.

Woolley, D. W. and White, A. G. C. (1943). Production of thiamine deficiency disease by the feeding of a pyridine analogue of thiamine. *J. Biol. Chem.* 149, 285-289.

Wyatt, D. T., Lee, M. and Hillman, R. E. (1989). Factors affecting a cyanogen bromide-based assay of thiamin. *Clin. Chem.* 35, 2173-2178.

Wyllie, A. H. (1985). The biology of cell death in tumours. *Anticancer Res.* 5, 131-136.

Wyllie, A. H., Kerr, J. F. R. and Currie, A. R. (1980). Cell death: The significance of apoptosis. *Intern. Rev. Cytol.* 68, 251-306.

Xu, M., Kumar, D., Stass, S. A. and Mixson, A. J. (1998). Gene therapy with P53 and a fragment of thrombospondin I inhibits human breast cancer in vivo. *Mol. Genet. Metab.* 63, 103-109.

Yoneda, J., Kuniyasu, H., Crispens, M. A., Price, J. E., Bucana, C. D. and Fidler, I. J. (1998). Expression of angiogenesis-related genes and progression of human ovarian carcinomas in nude mice. *J. Natl. Cancer Inst.* 90, 447-54.

Yu, H., Giai, M., Diamandis, E. P., Katsaros, D., Sutherland, D. J. A., Levesque, M. A., Roagna, R., Ponzone, R. and Sismondi, P. (1995). Prostate-specific antigen is a new favorable prognostic indicator for women with breast cancer. *Cancer Res.* 55, 2104-2110.

Yudkin, W. H. (1949). Thiaminase, the Chastek-paralysis factor. *Physiol. Rev.* 29, 389-402.

Zhang, S. X., Weilerbacher, G. S., Henderson, S. W., Corso, T., OLney, J. W., and Langlais, P. J. (1995): Excitotoxic cytopthology, progression and reversibility of thiamine deficiency-induced diencephalic lesions. *J. Neuropathol. Exp. Neurol.* 54:255-267.

Zhuang, S.-M., Shvarts, A., van Ormondt, H., Jochemsen, A. G., van der Eg, A. J. and Noteborn, M. H. M. (1995). Apoptin, a protein derived from chicken anemia virus, induces p53-independent apoptosis in human osteosarcoma cells. *Cancer Res.* 55, 486-489.

Ziche, M., Donnini, S., Morbidelli, Parenti, A., Gasparini, G. and Ledda, F. (1998). Linomide blocks angiogenesis by breast carcinoma vascular endothelial growth factor transfectants. *Br. J. Cancer* 77, 1123-1129.

Zimatkina, T., Yurkshtovich, T., Zimatkin, S. and Kaputsky, F. (1996).

Antitumor activity of hydroxythiamine and methotrexate immobilized on monocarboxycellulose. *Pol. J. Pharmacol.* 48, 163-169.

Zimatkina, T. I., Zimatkin, S. M., Oparin, D. A., Velichko, M. G. and Ostrovsky, Y. M. (1986). [Comparative evaluation of the action of oxythiamine and its derivatives on animals with Erhlich's ascitic cancer] (In Russian). *Eksp. Onkol.* 8, 68-70.

What we claim is:

1. A method of inducing apoptosis of a selected group of vertebrate cells in vivo, comprising reducing the level of thiamin in said cells,
    wherein said reducing comprises administering to an organism having said selected group of vertebrate cells at least one thiamin-depleting agent,
    wherein said thiamin-depleting agent is targeted to said selected group of vertebrate cells,
    wherein said thiamin-depleting agent is selected from the group consisting of a thiamin antimetabolite, a thiamin-cleaving compound, and a recombinant gene that encodes a polypeptide that acts as a thiamin-depleting agent, and
    wherein said thiamin antimetabolite is selected from the group consisting of a pyrithiamin, a thiamin substituted at the C-4 position of the thiamin pyrimidine, oxythiamin, an amprolium, and derivatives thereof.

2. The method of claim 1, wherein said thiamin-depleting agent is selected from the group consisting of a thiamin-cleaving compound, and a recombinant gene that encodes a polypeptide that acts as a thiamin-depleting agent.

3. The method of claim 2, wherein said thiamin-depleting agent is a thiamin-cleaving compound,
    wherein said thiamin-cleaving compound is a thiaminase.

4. The method of claim 2, wherein said thiamin-depleting agent is expressed from a recombinant gene in said vertebrate organism.

5. The method of claim 2, wherein said targeting is selected from the group consisting of localized administration of a thiamin-depleting agent, localized activation of a thiamin-depleting agent, localized expression of a nucleic acid sequence encoding a thiamin-depleting agent, localized binding of a thiamin-depleting agent, and localized binding of a targeting molecule associated with a thiamin-depleting agent.

6. The method of claim 2, wherein said thiamin-depleting agent comprises a plurality of said thiamin-depleting agents.

7. The method of claim 6, wherein said thiamin-depleting agent is a thiamin-cleaving compound.

8. The method of claim 2, wherein said selected group of vertebrate cells is a tumor.

9. The method of claim 1, wherein said wherein said thiamin-depleting agent is a thiamin antimetabolite selected from the group consisting of a pyrithiamin, a thiamin substituted at the C-4 position of the thiamin pyrimidine, oxythiamin, an amprolium, and derivatives thereof.

10. The method of claim 9, wherein said thiamin antimetabolite is selected from the group consisting of a pyrithiamin, a thiamin substituted at the C-4 position of the thiamin pyrimidine, oxythiamin, and an amprolium.

11. The method of claim 9, wherein said thiamin antimetabolite is a pyrithiamin.

12. The method of claim 9, wherein said thiamin antimetabolite is a thiamin substituted at the C-4 position of the thiamin pyrimidine.

13. The method of claim 9, wherein said thiamin antimetabolite is oxythiamin.

14. The method of claim 9, wherein said thiamin antimetabolite is an amprolium.

15. The method of claim 3, wherein said thiaminase is a naturally occurring thiaminase from *Bacillus thiaminolyticus*, a *Naegleria* species, a fern or other pteridophyte, or a fish from the Cyrprinidae family.

16. The method of claim 15, wherein said thiaminase is expressed from a recombinant gene in said organism.

17. The method of claim 3, wherein said thiaminase is a naturally occurring thiaminase from *Bacillus thiaminolyticus*.

18. The method of claim 17, wherein said thiaminase is expressed from a recombinant gene in said organism.

19. The method of claim 3, wherein said thiaminase is a modified thiaminase or a thiaminase derivative based on a naturally occurring thiaminase from *Bacillus thiaminolyticus*, a *Naegleria* species, a fern or other pteridophyte, or a fish from the Cyrprinidae family.

20. The method of claim 19, wherein said thiaminase is expressed from a recombinant gene in said organism.

21. The method of claim 3, wherein said thiaminase is a modified thiaminase or a thiaminase derivative based on a naturally occurring thiaminase from *Bacillus thiaminolyticus*.

22. The method of claim 21, wherein said thiaminase is expressed from a recombinant gene in said organism.

* * * * *